UnitedStatesPatent [12]
Nakano et al.

(10) Patent No.: US 7,919,086 B2
(45) Date of Patent: Apr. 5, 2011

(54) ANTI-GLYPICAN 3 ANTIBODY

(75) Inventors: Kiyotaka Nakano, Ibaraki (JP); Takeshi Yoshino, Ibaraki (JP); Jun-Ichi Nezu, Ibaraki (JP); Hiroyuki Tsunoda, Ibaraki (JP); Tomoyuki Igawa, Shizuoka (JP); Hiroko Konishi, Shizuoka (JP); Megumi Tanaka, Shizuoka (JO); Izumi Sugo, Shizuoka (JP); Shigeto Kawai, Kanagawa (JP); Takahiro Ishiguro, Kanagawa (JP); Yasuko Kinoshita, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 235 days.

(21) Appl. No.: 10/583,795

(22) PCT Filed: Jul. 8, 2005

(86) PCT No.: PCT/JP2005/013103
§ 371 (c)(1),
(2), (4) Date: Jun. 21, 2006

(87) PCT Pub. No.: WO2006/006693
PCT Pub. Date: Jan. 19, 2006

(65) Prior Publication Data
US 2007/0190599 A1 Aug. 16, 2007

(30) Foreign Application Priority Data
Jul. 9, 2004 (JP) ................................. 2004-203637

(51) Int. Cl.
C07K 16/28 (2006.01)
C07H 21/04 (2006.01)
C12N 5/06 (2006.01)
C12P 21/06 (2006.01)
(52) U.S. Cl. .............. 424/133.1; 530/388.22; 536/23.53
(58) Field of Classification Search ............... 424/133.1; 530/388.22; 536/23.53
See application file for complete search history.

(56) References Cited

U.S. PATENT DOCUMENTS

| 5,530,101 | A * | 6/1996 | Queen et al. ............... 530/387.3 |
| 6,165,745 | A | 12/2000 | Ward et al. |
| 6,210,670 | B1 * | 4/2001 | Berg ........................ 424/153.1 |
| 6,737,056 | B1 | 5/2004 | Presta |
| 7,297,775 | B2 | 11/2007 | Idusogie et al. |
| 7,361,336 | B1 | 4/2008 | Bergstein |
| 7,427,400 | B2 | 9/2008 | Bergstein |
| 2004/0024320 | A1 | 2/2004 | Karasawa et al. |
| 2004/0236080 | A1 | 11/2004 | Aburatani et al. |
| 2005/0171339 | A1 | 8/2005 | Sugo et al. |
| 2005/0233392 | A1 | 10/2005 | Filmus et al. |
| 2006/0024298 | A1 | 2/2006 | Lazar et al. |
| 2006/0040325 | A1 | 2/2006 | Wu et al. |
| 2006/0167232 | A1 | 7/2006 | Aburatani et al. |
| 2006/0188510 | A1 * | 8/2006 | Aburatani et al. ......... 424/155.1 |
| 2006/0287508 | A1 | 12/2006 | Sugo et al. |
| 2007/0087005 | A1 | 4/2007 | Lazar et al. |
| 2007/0172488 | A1 | 7/2007 | Aburtani et al. |
| 2007/0269444 | A1 | 11/2007 | Kinoshita et al. |
| 2008/0008710 | A1 | 1/2008 | Aburatani et al. |
| 2008/0051563 | A1 | 2/2008 | Lazar et al. |
| 2008/0124330 | A1 | 5/2008 | Nakano et al. |
| 2008/0154025 | A1 | 6/2008 | Lazar et al. |
| 2008/0161541 | A1 | 7/2008 | Lazar et al. |
| 2008/0181890 | A1 | 7/2008 | Lazar et al. |
| 2008/0267979 | A1 | 10/2008 | Lazar et al. |
| 2010/0248359 | A1 | 9/2010 | Nakano et al. |

FOREIGN PATENT DOCUMENTS

| EP | 1 176 195 | 1/2002 |
| EP | 1 331 266 | 7/2003 |
| EP | 1 411 118 | 4/2004 |
| EP | 1 462 799 | 9/2004 |
| EP | 1 464 702 | 10/2004 |
| EP | 1 498 491 | 1/2005 |
| EP | 1 548 442 | 6/2005 |
| EP | 1541680 | * 6/2005 |
| EP | 1 561 686 | 8/2005 |
| EP | 1 671 645 | 6/2006 |
| EP | 1 674 111 | 6/2006 |
| EP | 1 800 693 | 6/2007 |
| EP | 1 816 140 | 8/2007 |
| JP | 2-42355 | 2/1990 |
| JP | 4-336051 | 11/1992 |
| JP | 11-118775 | 4/1999 |
| JP | 2001-108661 | 4/2001 |
| JP | 2002-48867 | 2/2002 |
| JP | 2003-149213 | 5/2003 |
| JP | 2004-053360 | 2/2004 |
| WO | 9322332 | 11/1993 |
| WO | 9823289 | 6/1998 |
| WO | WO 99/54342 | 10/1999 |
| WO | WO 00/61739 | 10/2000 |

(Continued)

OTHER PUBLICATIONS

Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
MacCallum et al. (J. Mol. Biol. (1996) 262:732-745).*
Pascalis et al. (Journal of Immunology (2002) 169, 3076-3084).*
Casset et al. ((2003) BBRC 307, 198-205).*
Vajdos et al. ((2002) J. Mol. Biol. 320, 415-428).*
Holm et al ((2007) Mol. Immunol. 44: 1075-1084).*
Chen et al. (J. Mol. Bio. (1999) 293, 865-881).*
Wu et al. J. Mol. Biol. ((1999) 294, 151-162).*

(Continued)

*Primary Examiner* — Lynn Bristol
(74) *Attorney, Agent, or Firm* — Fish & Richardson P.C.

(57) ABSTRACT

An antibody capable of binding to a specific region of glypican 3, as well as a humanized antibody created based on that antibody are disclosed. The anti-GPC3 antibody of the invention has a higher ADCC activity and CDC activity compared with those of a conventional antibody. The antibody of the present invention is useful as a cell growth inhibitor, an anti-cancer agent and an agent for diagnosis of cancers.

56 Claims, 20 Drawing Sheets

FOREIGN PATENT DOCUMENTS

| WO | WO 02/22739 | 3/2002 |
|---|---|---|
| WO | WO 02/31140 | 4/2002 |
| WO | WO 02/079255 | 10/2002 |
| WO | WO 03/000883 | 1/2003 |
| WO | WO 03/042686 | 5/2003 |
| WO | WO 03/057881 | 7/2003 |
| WO | WO 03/074679 | 9/2003 |
| WO | WO 03/085119 | 10/2003 |
| WO | WO 03/100429 | 12/2003 |
| WO | WO 2004/018667 | 3/2004 |
| WO | WO 2004/022597 | 3/2004 |
| WO | WO 2004/022739 | 3/2004 |
| WO | WO 2004/022754 | 3/2004 |
| WO | WO 2004/023145 | 3/2004 |
| WO | WO 2004/038420 | 5/2004 |
| WO | WO 2004/099249 | 11/2004 |
| WO | WO 2005/023301 | 3/2005 |
| WO | WO 2006/006693 | 1/2006 |
| WO | WO 2006/022407 | 3/2006 |
| WO | WO 2006/046751 | 5/2006 |
| WO | WO 2007/047291 | 4/2007 |

OTHER PUBLICATIONS

Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Voskoglou-Nomikos (Clin. Can. Res. 9:4227-4239 (2003)).*
Dennis (Nature 442:739-741 (2006)).*
Seaver (1994; Genetic Engineering vol. 14(14):pp. 10 and 21).*
Dufner (Trends Biotechnol. 24(11):523-29 (2006)).*
Bost et al. (Immunol. Invest. (1988) 17:577-586).*
Bendayan (J. Histochem. Cytochem. (1995) 43:881-886).*
Wichert et al. (Oncogene Jan. 29, 2004;23(4):945-55).*
Steplewski et al. (Proc. Natl. Acad. Sci. USA, 1988 85: 4852-4856).*
Capurro et al. "Glypican-3: A novel serum and histochemical marker for hepatocellular carcinoma". Gastroenterology 125(1):89-97, Jul. 2003.
Capurro et al. "Overexpression of Glypican-3 in Human Hepatocellular Carcinomas Determined by immunohistochemistry using a monoclonal antibody". Proceedings, American Association for Cancer Research, 93$^{rd}$ Annual Meeting, Apr. 6-10, 2002, vol. 43, Abstract #1097, Mar. 2002.
Filmus. "Glypicans in Growth Control and Cancer". Glycobiology, 11(3):19R-23R, 2001.
Gonzalez et al. "OCI-5/GPC3, A Glypican Encoded by a Gene That is Mutated in the Simpson-Golabi-Behmel Overgrowth Syndrome, Induces Apoptosis in a Cell Line-Specific Manner". The Journal of Cell Biology, 141(6):1407-1414, 1998.
Huber. "Structure and Function of the Human Glypican 3 Gene". Washington University, Division of Biology and Biomedical Sciences Program in Molecular Genetics, St. Louis, Missouri, Dec. 1998.
Lage et al. "Cloning and Characterization of Human cDNAs Encoding a Protein with High Homology to Rat Intestinal Development Protein OCI-5". Gene 188:151-156, 1997.
Lage et al. "Expression of a Glypican-Related 62-kDa Antigen is Decreased in Hepatocellular Carcinoma in Correspondence to the Grade of Tumor Differentiation". Virchows Arch, 438:567-573, 2001.
Midorikawa et al. "Glypican-3, Overexpressed in Hepatocellular Carcinoma, Modulates FGF2 and BMP-7 Signaling." Int. J. Cancer 103:445-465, 2003.
Pilia et al. "Mutations in GPC3, A Glypican Gene, Cause the Simpson-Golabi-Behmel Overgrowth Syndrome". Nature Genetics, 12:241-247, 1996.
Sung et al. "Glypican-3 is overexpressed in human hepatocellular carcinoma". Cancer Science 94(3):259-262, Mar. 2003.
USPTO Restriction Requirement in U.S. Appl. No. 10/526,741, dated Mar. 27, 2006, 5 pages.
Davidson, Davidson & Kappel, LLC, Response to Restriction Requirement dated Mar. 27, 2006 in U.S. Appl. No. 10/526,741, filed Apr. 25, 2006, 6 pages.
USPTO Office Action in U.S. Appl. No. 10/526,741, dated Jun. 14, 2006, 40 pages.
Davidson, Davidson & Kappel, LLC, Amendment in Reply to Office Action dated Jun. 14, 2006 in U.S. Appl. No. 10/526,741, filed Dec. 12, 2006, 18 pages.
USPTO Final Office Action in U.S. Appl. No. 10/526,741, dated Mar. 9, 2007, 17 pages.
Davidson, Davidson & Kappel, LLC, Amendment in Reply to Office Action dated Mar. 9, 2007 in U.S. Appl. No. 10/526,741, filed Jul. 9, 2007, 9 pages.
USPTO Advisory Action in U.S. Appl. No. 10/526,741, dated Aug. 14, 2007, 3 pages.
Davidson, Davidson & Kappel, LLC, Amendment in Reply to Action dated Aug. 14, 2007 in U.S. Appl. No. 10/526,741, filed Sep. 6, 2007, 9 pages.
USPTO Office Action in U.S. Appl. No. 10/526,741, dated Nov. 21, 2007, 17 pages.
Davidson, Davidson & Kappel, LLC, Amendment in Reply to Action dated Nov. 21, 2007 in U.S. Appl. No. 10/526,741, filed Mar. 20, 2008, 10 pages.
USPTO Final Office Action in U.S. Appl. No. 10/526,741, dated Jul. 9, 2008, 11 pages.
Davidson, Davidson & Kappel, LLC, Amendment in Reply to Office Action dated Jul. 9, 2008 in U.S. Appl. No. 10/526,741, filed Jan. 5, 2009, 113 pages.
USPTO Advisory Action in U.S. Appl. No. 10/526,741, dated Jan. 21, 2009, 4 pages.
USPTO Office Action in U.S. Appl. No. 10/526,741, dated Sep. 1, 2009, 15 pages.
USPTO Final Office Action in U.S. Appl. No. 11/577,944, dated Jan. 20, 2010, 47 pages.
Rudikoff et al., "Single amino acid substitution altering antigen-binding specificity," Proc. Natl. Acad. Sci. USA, 79:1979-1983 (1982).
Abe et al., "Matrixeye™ portable 3D ultrasonic inspection system," Toshiba Rev., 60:48-51 (2005).
Carter, "Improving the efficacy of antibody-based cancer therapies," Nat. Rev. Cancer, 1:118-129 (2001).
Gura, "Systems for identifying new drugs are often faulty," Science, 278:1041-42 (1997).
Hippo et al., "Identification of soluble $NH_2$-terminal fragment of glypican-3 as a serological marker for early-stage hepatocellular carcinoma," Cancer Res., 64:2418-23 (2004).
Jiang et al., "Recurrence or metastasis of HCC: predictors, early detection and experimental antiangiogenic therapy," World J. Gastroenterol., 6:61-65 (2000).
Lund et al., "Multiple interactions of IgG with its core oligosaccharide can modulate recognition by complement and human Fcγ receptor I and influence the synthesis of its oligosaccharide chains," J. Immunol., 157:4963-69 (1996).
Man et al., "Upregulation of glypican-3 expression in hepatocellular carcinoma but downregulation in cholangiocarcinoma indicates its differential diagnosis value in primary liver cancers," Liver Int., 25:962-966 (2005).
MSNBC News Service, "Mixed results on new cancer drug," 4 pages (2000).
Nakatsura et al., "Glypican-3, overexpressed specifically in human hepatocellular carcinoma, is a novel tumor marker," Biochem. Biophys. Res. Commun., 306:16-25 (2003).
Niwa et al., "Defucosylated chimeric anti-CC chemokine receptor 4 IgG1 with enhanced antibody-dependent cellular cytotoxicity shows potent therapeutic activity to T-cell leukemia and lymphoma," Cancer Res., 64:2127-33 (2004).
Presta, "Engineering antibodies for therapy," Curr. Pharm. Biotechnol., 3:237-256 (2002).
Roskams et al., "Heparan sulphate proteoglycan expression in human primary liver tumours," J. Pathol., 185:290-297 (1998).
Sabit et al., "Enhanced expression of basement-membrane-type heparan sulfate proteoglycan in tumor fibro-myxoid stroma of intrahepatic cholangiocarcinoma," Pathol. Int., 51:248-256 (2001).

Shields et al., "Lack of fucose on human IgG1 N-linked oligosaccharide improves binding to human Fcgamma RIII and antibody-dependent cellular cytotoxicity," *J Biol. Chem.*, 277:26733-40 (2002).
Shinkawa et al., "The absence of fucose but not the presence of galactose or bisecting N-acetylglucosamine of human IgG1 complex-type oligosaccharides shows the critical role of enhancing antibody-dependent cellular cytotoxicity," *J. Biol. Chem.*, 278:3466-73 (2003).
Yamaguchi et al., "Current status and future perspective of biotherapy for cancer," *Biotherapy*, 13:747-753 (1999) (English summary included).
Yamane-Ohnuki et al., "Establishment of *FUT8* knockout Chinese hamster ovary cells: an ideal host cell line for producing completely defucosylated antibodies with enhanced antibody-dependent cellular cytotoxicity," *Biotechnol. Bioeng.*, 87:614-622 (2004).
USPTO Restriction Requirement in U.S. Appl. No. 11/251,561, dated Dec. 13, 2007, 9 pages.
Fish & Richardson P.C., Response to Restriction Requirement dated Dec. 13, 2007 in U.S. Appl. No. 11/251,561, filed Feb. 12, 2008, 1 page.
USPTO Office Action in U.S. Appl. No. 11/251,561, dated May 14, 2008, 12 pages.
Fish & Richardson P.C., Amendment in Reply to Action dated May 14, 2008 in U.S. Appl. No. 11/251,561, filed Nov. 13, 2008, 8 pages.
USPTO Final Office Action in U.S. Appl. No. 11/251,561, dated Feb. 25, 2009, 13 pages.
International Search Report and Written Opinion for App. Ser. No. PCT/US2006/039682 dated Apr. 13, 2007, 13 pages.
USPTO Restriction Requirement in U.S. Appl. No. 10/570,647, dated Apr. 4, 2008, 6 pages.
Japanese Patent Office, International Search Report for App. Ser. No. PCT/JP2004/013183, mailed Nov. 30, 2004, 4 pages.
Japanese Patent Office, International Preliminary Report on Patentability for App. Ser. No. PCT/JP2004/013183, dated Sep. 1, 2005, 17 pages.
European Search Report for App. Ser. No. EP 04 77 2 922, dated Jun. 14, 2007, 2 pages.
USPTO Restriction Requirement in U.S. Appl. No. 11/574,091, dated Dec. 17, 2008, 8 pages.
Fish & Richardson P.C., Response to Restriction Requirement dated Dec. 17, 2008 in U.S. App. Ser. No. 11/574,091, filed Jun. 16, 2009, 1 page.
USPTO Office Action in U.S. Appl. No. 11/574,091, dated Sep. 2, 2009, 18 pages.
Japanese Patent Office, International Search Report for App. Ser. No. PCT/JP2005/015607, mailed Oct. 24, 2005, 3 pages.
European Search Report for App. Ser. No. EP 05 78 0979, dated Nov. 10, 2008, 5 pages.
USPTO Office Action in U.S. Appl. No. 11/577,944, dated Apr. 28, 2009, 14 pages.
Fish & Richardson P.C., Amendment in Reply to Office Action dated Apr. 28, 2009 in U.S. Appl. No. 11/577,944, filed Oct. 27, 2009, 15 pages.
Japanese Patent Office, International Search Report for App. Ser. No. PCT/JP2005/020057, mailed Jan. 24, 2006, 2 pages.
European Search Report for App. Ser. No. EP 05 80 0031, dated Jul. 31, 2009, 9 pages.
International Search Report and Written Opinion for App. Ser. No. SG 200703074-5, mailed Jul. 21, 2008, 9 pages.
Japanese Patent Office, International Search Report for App. Ser. No. PCT/JP2005/013103, mailed Oct. 25, 2005, 1 page.
Japanese Patent Office, International Preliminary Report on Patentability for App. Ser. No. PCT/JP2005/013103, dated Jan. 7, 2009, 4 pages.
European Search Report for App. Ser. No. EP 05 76 0156, dated Oct. 1, 2007, 15 pages.
Arii et al., "Characteristics of recurrent hepatocellular carcinoma in Japan and our surgical experience," *J. Hepatobiliary Pancrea. Surg.*, 8:397-403 (2001).
Budhu et al., "The Molecular Signature of Metastases of Human Hepatocellular Carcinoma," *Oncology*, 69 (suppl 1):23-27 (2005).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *J. Cell Biol.*, 111:2129-38 (1990).
Ghetie et al., "Multiple Roles for the Major Histocompatibility Complex Class I-Related Receptor FcRn," *Annu. Rev. Immunol.*, 18:739-766 (2000).
Hinton et al,. "Engineered Human IgG Antibodies with Longer Serum Half-lives in Primates," *J. Biol. Chem.*, 279:6213-16 (2004).
Kim et al., "Mapping the site on human IgG for binding of the MHC class I-related receptor, FcRn," *Eur. J. Immunol.*, 29:2819-25 (1999)
.
Lazar et al., "Transforming Growth Factor alpha: Mutation of Aspartic Acid 47 and Leucine 48 Results in Different Biological Activities," *Mol. Cell. Biol.*, 8:1247-52 (1988).
Martin et al., "Crystal Structure at 2.8 A of an FcRn/Heterodimeric Fc Complex: Mechanism of pH-Dependent Binding," *Molecular Cell*, 7:867-877 (2001).
Medesan et al., "Delineation of the Amino Acid Residues Involved in Transcytosis and Catabolism of Mouse IgG1," *J. Immunol.*, 158:2211-17 (1997).
Raghavan et al., "Fc Receptors and their Interactions with Immunoglobulins," *Annu. Rev. Cell Dev. Biol.*, 12:181-220 (1996).
Tang et al., "Metastatic human hepatocellular carcinoma models in nude mice and cell line with metastatic potential," *World J. Gastroenterol.*, 7:597-601 (2001).
Fish & Richardson P.C., Reply to Action dated Feb. 25, 2009 in U.S. Appl. No. 11/251,561, filed Mar. 24, 2010, 4 pages.
Fish & Richardson P.C., Supplemental Amendment in Reply to Action dated Feb. 25, 2009 in U.S. Appl. No. 11/251,561, filed Mar. 26, 2010, 16 pages.
Fish & Richardson P.C., Amendment in Reply to Action dated Sep. 2, 2009 in U.S. Appl. No. 11/574,091, filed Mar. 2, 2010, 7 pages.
U.S. Examiner Anne Gussow, USPTO Final Office Action in U.S. Appl. No. 11/574,091, dated May 11, 2010, 16 pages.
Fish & Richardson P.C., Amendment in Reply to Office Action dated Jan. 20, 2010 in U.S. Appl. No. 11/577,944, filed Apr. 29, 2010, 6 pages.
U.S. Examiner Anne Gussow, USPTO Interview Summary in U.S. Appl. No. 11/577,944, dated May 3, 2010, 3 pages.
U.S. Examiner Anne Gussow, USPTO Non-Final Office Action in U.S. Appl. No. 11/577,944, dated May 21, 2010, 16 pages.
Davidson, Davidson & Kappel, LLC, Amendment in Reply to Office Action dated Sep. 1, 2009 in U.S. Appl. No. 10/526,741, filed Feb. 24, 2010, 10 pages.
U.S. Examiner Audrey S. Pham, USPTO Office Action in U.S. Appl. No. 10/481,524, dated Apr. 3, 2006, 23 pages.
Davidson, Davidson & Kappel, LLC, Amendment in Reply to Office Action dated Apr. 3, 2006 in U.S. Appl. No. 10/481,524, filed Aug. 31, 2006, 9 pages.
U.S. Examiner Catherine Joyce, USPTO Interview Summary in U.S. Appl. No. 10/481,524, dated Sep. 6, 2006, 3 pages.
U.S. Examiner Catherine Joyce, USPTO Restriction Requirement in U.S. Appl. No. 10/481,524, dated Jan. 5, 2007, 4 pages.
U.S. Examiner Catherine Joyce, USPTO Office Communication in U.S. Appl. No. 10/481,524, dated Jan. 23, 2007, 2 pages.
U.S. Examiner Catherine Joyce, USPTO Restriction Requirement in U.S. Appl. No. 11/702,780, dated Jul. 24, 2007, 5 pages.
Davidson, Davidson & Kappel, LLC, Response to Restriction Requirement dated Jul. 24, 2007 in U.S. Appl. No. 11/702,780, filed Aug. 22, 2007, 4 pages.
U.S. Examiner Alana M. Harris, USPTO Office Action in U.S. Appl. No. 11/702,780, dated Nov. 16, 2007, 9 pages.
U.S. Examiner Alana M. Harris, USPTO Interview Summary in U.S. Appl. No. 11/702,780, dated Dec. 14, 2007, 4 pages.
Davidson, Davidson & Kappel, LLC, Amendment in Reply to Office Action dated Nov. 16, 2007 in U.S. Appl. No. 11/702,780, filed May 16, 2008, 11 pages.
U.S. Examiner Alana M. Harris, USPTO Office Action in U.S. Appl. No. 11/702,780, dated Sep. 3, 2008, 9 pages.
Davidson, Davidson & Kappel, LLC, Amendment in Reply to Office Action dated Sep. 3, 2008 in U.S. Appl. No. 11/702,780, filed Dec. 29, 2008, 6 pages.

U.S. Examiner Alana M. Harris, USPTO Advisory Action in U.S. Appl. No. 11/702,780, dated Jan. 13, 2009, 4 pages.

U.S. Examiner Alana M. Harris, USPTO Office Action in U.S. Appl. No. 11/702,780, dated Apr. 2, 2009.

Davidson, Davidson & Kappel, LLC, Amendment in Reply to Office Action dated Apr. 2, 2009 in U.S. Appl. No. 11/702,780, filed Sep. 30, 2009, 215 pages.

U.S. Examiner Alana M. Harris, USPTO Notice of Allowance in U.S. Appl. No. 11/702,780, dated Jan. 26, 2010, 5 pages.

Nakano et al., "Anti-glypican 3 antibodies cause ADCC against human hepatocellular carcinoma cells," Biochem. Biophys. Res. Comm., 378:279-284 (2008).

European Examiner Zoran Cilensek, Partial European Search Report in EP 10003424.8, Jun. 30, 2010.

Ohno et al., "Antigen-binding specificities of antibodies are primarily determined by seven residues of VH," Proc. Natl. Acad. Sci. U.S.A., 82:2945-49 (1985).

Roitt et al., "Immunology," Moscow, 102, 106-107 (2000).

U.S. Examiner Chun Wu Dahle, USPTO Restriction Requirement in U.S. Appl. No. 12/089,957, dated Sep. 1, 2010, 7 pages.

Fish & Richardson P.C., Amendment in Reply to Action dated May 11, 2010 in U.S. Appl. No. 11/574,091, filed Aug. 11, 2010, 6 pages.

U.S. Examiner Anne Gussow, USPTO Notice of Allowance in U.S. Appl. No. 11/574,091, dated Aug. 31, 2010, 6 pages.

Fish & Richardson P.C., Amendment in Reply to Office Action dated May 21, 2010 in U.S. Appl. No. 11/577,944, filed Jun. 9, 2010, 5 pages.

U.S. Examiner Anne Gussow, USPTO Notice of Allowance in U.S. Appl. No. 11/577,944, dated Aug. 26, 2010, 6 pages.

\* cited by examiner

| Mab | Inhibition of the binding of indicated biotin-Mab to sGPC3 core (%) | | | | | | | | Topographical epitope |
|---|---|---|---|---|---|---|---|---|---|
| | M3C11 | M1E7 | M11F1 | M6B1 | M18D4 | M5B9 | M10D2 | L9G11 | |
| M3C11 | 96.8 | 96.2 | 12.0 | 11.2 | 10.3 | 9.1 | 39.9 | 33.1 | a |
| M13B3 | 71.3 | 95.7 | 15.6 | 9.3 | 2.7 | -1.8 | 22.3 | 24.9 | |
| M1E7 | 26.0 | 83.9 | 14.3 | 7.7 | 9.0 | 6.4 | 14.8 | 38.0 | |
| M3B8 | 1.8 | 28.4 | 97.4 | 15.2 | 12.6 | 3.6 | 29.0 | 36.0 | b |
| M11F1 | 2.0 | 3.9 | 81.8 | 5.6 | -1.5 | 5.4 | 24.6 | 20.9 | |
| M19B11 | -4.1 | -9.4 | 3.1 | 87.6 | 44.1 | 31.0 | 14.2 | -9.8 | c |
| M6B1 | -5.7 | -2.7 | 13.9 | 85.6 | 51.9 | 44.4 | 6.7 | 1.1 | |
| M18D4 | 0.2 | 0.5 | -0.3 | 38.6 | 89.0 | 89.4 | 19.1 | 6.7 | |
| M5B9 | 0.1 | 2.7 | 5.3 | 23.2 | 77.3 | 77.3 | 13.4 | 10.3 | |
| M10D2 | -7.7 | 0.6 | 7.8 | -5.9 | -21.6 | -10.3 | 79.2 | 7.2 | d |
| L9G11 | 2.1 | -4.8 | 6.0 | 10.1 | 15.7 | 6.4 | 1.2 | 92.2 | e |

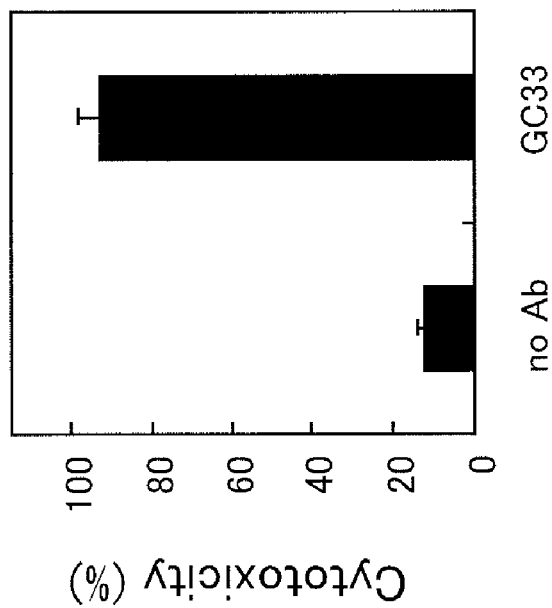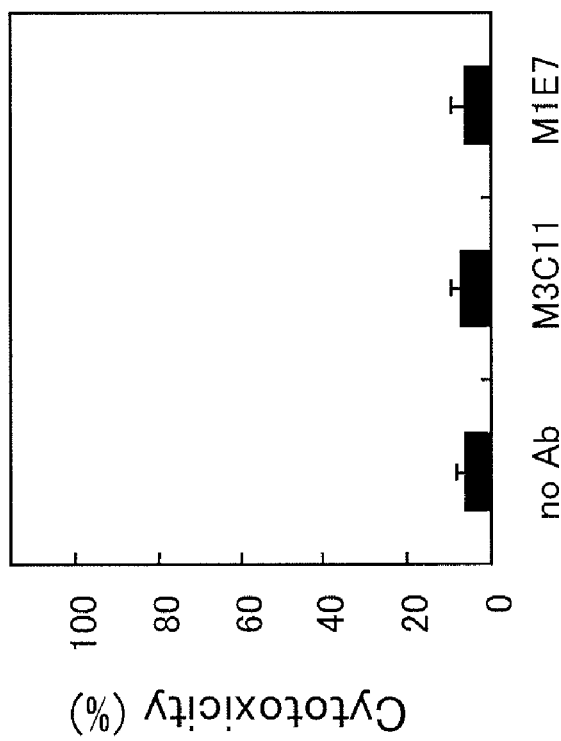
FIG.11

| | | GC33 WB |
|---|---|---|
| GC-4 | G N S Q Q A T P K D N E I S T F H N L G N V H S P L K | ○ |
| GC-5 | S T F H N L G N V H S P L K | × |
| GC-6 | G N S Q Q A T P K D N E I S | × |
| GC-7 | G N S Q Q A T P | × |
| GC-8 | Q Q A T P K D N | × |
| GC-9 | T P K D N E I S | × |
| GC-11 | A T P K D N E I S T | ○ |
| GC-12 | P K D N E I S T F H | ○ |
| GC-13 | D N E I S T F H N L | ○ |
| GC-14 | E I S T F H N L G N | × |

FIG.13

| Clone ID | Isotype | ELISA EC50 (nM) | BIACORE ka (1/Ms /10^5) | BIACORE kd (1/s x10^5) | BIACORE KD (nM) | EPITOPE Competitive ELISA | EPITOPE western blotting | FACS CHO/ human GPC3 | FACS HepG2 | FACS HuH-7 | FACS CHO | Immuno-precipitation |
|---|---|---|---|---|---|---|---|---|---|---|---|---|
| M3C11 | IgG1 | 0.12 | 2.5 | 6.5 | 0.3 | a | GC-2 | 83 | 59 | 9 | - | △ |
| M13B3 | IgG1 | 0.25 | N.D. | N.D. | N.D. | | | N.D. | N.D. | N.D. | - | N.D. |
| M1E7 | IgG1 | 0.96 | 1.5 | 42.7 | 2.8 | b | GC-4 | 28 | 16 | 5 | - | × |
| M3B8 | IgG1 | 0.56 | 2.7 | 467.0 | 17.6 | | | 12 | 6 | 3 | - | × |
| M11F1 | IgG2b | 2.17 | 1.4 | 3.5 | 0.2 | | | 9 | 4 | 2 | - | × |
| L9G11 | IgG1 | 0.62 | 1.3 | 140.0 | 10.7 | e | N | 29 | 26 | 4 | - | ○ |
| M19B11 | IgG1 | 0.18 | 1.5 | 17.1 | 1.1 | | | 39 | 44 | 3 | - | ○ |
| M6B1 | IgG1 | 5.51 | N.D. | N.D. | N.D. | c | | 37 | 34 | 3 | - | ○ |
| M18D4 | IgG1 | 0.85 | 0.8 | 49.6 | 6.2 | | | 22 | 20 | 2 | - | ○ |
| M5B9 | IgG1 | 1.13 | 0.6 | 139.0 | 23.5 | | | 25 | 23 | 2 | - | ○ |
| M10D2 | IgG1 | 1.04 | 1.1 | 49.6 | 4.7 | d | | 20 | 29 | 3 | - | ○ |

FIG.16

| Clone ID | ELISA EC50 (nM) | EPITOPE | | FACS | | | |
|---|---|---|---|---|---|---|---|
| | | Competitive ELISA | Western blotting | CHO/ human GPC3 | HepG2 | HuH-7 | CHO |
| GC199 | 0.10 | b | GC-4 | 15.5 | 12.2 | 2.4 | - |
| GC202 | 0.10 | | | 6.0 | 0.9 | 1.4 | - |
| GC33 | 0.24 | | | 82.7 | 52.0 | 8.4 | - |
| GC179 | 5.61 | f | GC-3 | 7.1 | 6.5 | 3.8 | - |
| GC194 | 3.83 | | | 5.0 | 7.9 | 1.5 | - |

FIG.17

SEQUENCE LISTING

<160> NUMBER OF SEQ ID NOS: 207

<210> SEQ ID NO 1
<211> LENGTH: 31
<212> TYPE: DNA
<213> ORGANISM: Artificial Sequence
<220> FEATURE:
<223> OTHER INFORMATION: PCR primer

<400> SEQUENCE: 1
gatatcatgg ccgggaccgt gcgcaccgcg t                              31

<210> SEQ ID NO 2
<211> LENGTH: 31
<212> TYPE: DNA
<213> ORGANISM: Artificial Sequence
<220> FEATURE:
<223> OTHER INFORMATION: PCR primer

<400> SEQUENCE: 2
gctagctcag tgcaccagga agaagaagca c                              31

<210> SEQ ID NO 3
<211> LENGTH: 1743
<212> TYPE: DNA
<213> ORGANISM: Homo sapiens

<400> SEQUENCE: 3
atggccggga ccgtgcgcac cgcgtgcttg gtggtggcga tgctgctcag cttggacttc     60
ccgggacagg cgcagccccc gccgccgccg ccggacgcca cctgtcacca agtccgctcc    120
ttcttccaga gactgcagcc cggactcaag tgggtgccag aaactcccgt gccaggatca    180
gatttgcaag tatgtctccc taagggccca acatgctgct caagaaagat ggaagaaaaa    240
taccaactaa cagcacgatt gaacatggaa cagctgcttc agtctgcaag tatggagctc    300
aagttcttaa ttattcagaa tgctgcggtt ttccaagagg cctttgaaat tgttgttcgc    360
catgccaaga actacaccaa tgccatgttc aagaacaact acccaagcct gactccacaa    420
gcttttgagt ttgtgggtga attttttcaca gatgtgtctc tctacatctt gggttctgac    480
atcaatgtag atgacatggt caatgaattg tttgacagcc tgtttccagt catctatacc    540
cagctaatga acccaggcct gcctgattca gccttggaca tcaatgagtg cctccgagga    600
gcaagacgtg acctgaaagt atttgggaat tccccaagc ttattatgac ccaggttttcc    660 aagtcactgc aagtcactag gatcttcctt caggctctga tcttggaat tgaagtgatc    720 aacacaactg atcacctgaa gttcagtaag gactgtggcc gaatgctcac cagaatgtgg    780
tactgctctt actgccaggg actgatgatg gttaaaccct gtggcggtta ctgcaatgtg    840
gtcatgcaag gctgtatggc aggtgtggtg gagattgaca gtactggag agaatacatt    900 ctgtcccttg aagaacttgt gaatggcatg tacagaatct atgacatgga gaacgtactg    960
cttggtctct ttcaacaat ccatgattct atccagtatg tccagaagaa tgcaggaaag   1020
ctgaccacca ctattggcaa gttatgtgcc cattctcaac aacgccaata tagatctgct   1080
tattatcctg aagatctctt tattgacaag aaagtattaa agttgctca tgtagaacat   1140 gaagaaacct atccagccg aagaagggaa ctaattcaga agttgaagtc tttcatcagc   1200
ttctatagtg ctttgcctgg ctacatctgc agccatagcc ctgtggcgga aaacgacacc   1260 cttttgctgga atggacaaga actcgtggag agatacagcc aaaaggcagc aaggaatgga   1320

-continued

```
atgaaaaacc agttcaatct ccatgagctg aaaatgaagg gccctgagcc agtggtcagt    1380
caaattattg acaaactgaa gcacattaac cagctcctga gaaccatgtc tatgcccaaa    1440
ggtagagttc tggataaaaa cctggatgag gaagggtttg aaagtggaga ctgcggtgat    1500
gatgaagatg agtgcattgg aggctctggt gatggaatga taaaagtgaa gaatcagctc    1560
cgcttccttg cagaactggc ctatgatctg gatgtggatg atgcgcctgg aaacagtcag    1620
caggcaactc cgaaggacaa cgagataagc acctttcaca acctcgggaa cgttcattcc    1680
ccgctgaagc ttctcaccag catggccatc tcggtggtgt gcttcttctt cctggtgcac    1740
tga                                                                  1743
```

<210> SEQ ID NO 4
<211> LENGTH: 580
<212> TYPE: PRT
<213> ORGANISM: Homo sapiens

<400> SEQUENCE: 4

```
Met Ala Gly Thr Val Arg Thr Ala Cys Leu Val Ala Met Leu Leu
1               5                   10                  15

Ser Leu Asp Phe Pro Gly Gln Ala Gln Pro Pro Pro Pro Pro Asp
            20                  25                  30

Ala Thr Cys His Gln Val Arg Ser Phe Phe Gln Arg Leu Gln Pro Gly
        35                  40                  45

Leu Lys Trp Val Pro Glu Thr Pro Val Pro Gly Ser Asp Leu Gln Val
    50                  55                  60

Cys Leu Pro Lys Gly Pro Thr Cys Cys Ser Arg Lys Met Glu Glu Lys
65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
            100                 105                 110

Glu Ala Phe Glu Ile Val Val Arg His Ala Lys Asn Tyr Thr Asn Ala
        115                 120                 125

Met Phe Lys Asn Asn Tyr Pro Ser Leu Thr Pro Gln Ala Phe Glu Phe
    130                 135                 140

Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
                165                 170                 175

Val Ile Tyr Thr Gln Leu Met Asn Pro Gly Leu Pro Asp Ser Ala Leu
            180                 185                 190

Asp Ile Asn Glu Cys Leu Arg Gly Ala Arg Arg Asp Leu Lys Val Phe
        195                 200                 205

Gly Asn Phe Pro Lys Leu Ile Met Thr Gln Val Ser Lys Ser Leu Gln
    210                 215                 220

Val Thr Arg Ile Phe Leu Gln Ala Leu Asn Leu Gly Ile Glu Val Ile
225                 230                 235                 240

Asn Thr Thr Asp His Leu Lys Phe Ser Lys Asp Cys Gly Arg Met Leu
                245                 250                 255

Thr Arg Met Trp Tyr Cys Ser Tyr Cys Gln Gly Leu Met Met Val Lys
            260                 265                 270

Pro Cys Gly Gly Tyr Cys Asn Val Val Met Gln Gly Cys Met Ala Gly
        275                 280                 285

Val Val Glu Ile Asp Lys Tyr Trp Arg Glu Tyr Ile Leu Ser Leu Glu
    290                 295                 300
```

```
Glu Leu Val Asn Gly Met Tyr Arg Ile Tyr Asp Met Glu Asn Val Leu
305                 310                 315                 320

Leu Gly Leu Phe Ser Thr Ile His Asp Ser Ile Gln Tyr Val Gln Lys
                325                 330                 335

Asn Ala Gly Lys Leu Thr Thr Ile Gly Lys Leu Cys Ala His Ser
            340                 345                 350

Gln Gln Arg Gln Tyr Arg Ser Ala Tyr Tyr Pro Glu Asp Leu Phe Ile
        355                 360                 365

Asp Lys Lys Val Leu Lys Val Ala His Val Glu His Glu Glu Thr Leu
    370                 375                 380

Ser Ser Arg Arg Arg Glu Leu Ile Gln Lys Leu Lys Ser Phe Ile Ser
385                 390                 395                 400

Phe Tyr Ser Ala Leu Pro Gly Tyr Ile Cys Ser His Ser Pro Val Ala
                405                 410                 415

Glu Asn Asp Thr Leu Cys Trp Asn Gly Gln Glu Leu Val Glu Arg Tyr
            420                 425                 430

Ser Gln Lys Ala Ala Arg Asn Gly Met Lys Asn Gln Phe Asn Leu His
        435                 440                 445

Glu Leu Lys Met Lys Gly Pro Glu Pro Val Val Ser Gln Ile Ile Asp
    450                 455                 460

Lys Leu Lys His Ile Asn Gln Leu Leu Arg Thr Met Ser Met Pro Lys
465                 470                 475                 480

Gly Arg Val Leu Asp Lys Asn Leu Asp Glu Glu Gly Phe Glu Ser Gly
                485                 490                 495

Asp Cys Gly Asp Asp Glu Asp Glu Cys Ile Gly Gly Ser Gly Asp Gly
            500                 505                 510

Met Ile Lys Val Lys Asn Gln Leu Arg Phe Leu Ala Glu Leu Ala Tyr
        515                 520                 525

Asp Leu Asp Val Asp Asp Ala Pro Gly Asn Ser Gln Gln Ala Thr Pro
    530                 535                 540

Lys Asp Asn Glu Ile Ser Thr Phe His Asn Leu Gly Asn Val His Ser
545                 550                 555                 560

Pro Leu Lys Leu Leu Thr Ser Met Ala Ile Ser Val Val Cys Phe Phe
                565                 570                 575

Phe Leu Val His
            580

<210> SEQ ID NO 5
<211> LENGTH: 31
<212> TYPE: DNA
<213> ORGANISM: Artificial Sequence
<220> FEATURE:
<223> OTHER INFORMATION: PCR primer

<400> SEQUENCE: 5
atagaattcc accatggccg ggaccgtgcg c                              31

<210> SEQ ID NO 6
<211> LENGTH: 31
<212> TYPE: DNA
<213> ORGANISM: Artificial Sequence
<220> FEATURE:
<223> OTHER INFORMATION: PCR primer

<400> SEQUENCE: 6
ataggatccc ttcagcgggg aatgaacgtt c                              31
```

```
<210> SEQ ID NO 7
<211> LENGTH: 21
<212> TYPE: DNA
<213> ORGANISM: Artificial Sequence
<220> FEATURE:
<223> OTHER INFORMATION: PCR primer

<400> SEQUENCE: 7
gggccagtgg atagacagat g                                              21

<210> SEQ ID NO 8
<211> LENGTH: 24
<212> TYPE: DNA
<213> ORGANISM: Artificial Sequence
<220> FEATURE:
<223> OTHER INFORMATION: PCR primer

<400> SEQUENCE: 8
caggggccag tggatagacc gatg                                           24

<210> SEQ ID NO 9
<211> LENGTH: 24
<212> TYPE: DNA
<213> ORGANISM: Artificial Sequence
<220> FEATURE:
<223> OTHER INFORMATION: PCR primer

<400> SEQUENCE: 9
caggggccag tggatagact gatg                                           24

<210> SEQ ID NO 10
<211> LENGTH: 23
<212> TYPE: DNA
<213> ORGANISM: Artificial Sequence
<220> FEATURE:
<223> OTHER INFORMATION: PCR primer

<400> SEQUENCE: 10
gctcactgga tggtgggaag atg                                            23

<210> SEQ ID NO 11
<211> LENGTH: 1392
<212> TYPE: DNA
<213> ORGANISM: Mus musculus

<400> SEQUENCE: 11
atgaacttcg ggctcacctt gattttcctt gtccttactt taaaaggtgt ccagtgtgag    60
gtgcaactgg tggagtctgg gggaggctta gtgaagcctg gaggatccct gaaactctcc   120
tgtgcagcct ctggattcac tttcagtcgc tatgccatgt cttgggttcg ccagattcca   180
gagaagatac tggagtgggt cgcagccatt gatagtagtg gtggtgacac ctactattta   240
gacactgtga aggaccgatt caccatctcc agagacaatg ccaataatac cctgcacctg   300
caaatgcgca gtctgaggtc tgaggacaca gccttgtatt actgtgtaag acagggggg   360 gcttactggg gccaagggac tctggtcact gtctctgcag ctagcaccaa gggcccatcg   420
gtcttccccc tggcaccctc ctccaagagc acctctgggg gcacagcggc cctgggctgc   480
ctggtcaagg actacttccc cgaaccggtg acggtgtcgt ggaactcagg cgccctgacc   540
agcggcgtgc acaccttccc ggctgtccta cagtcctcag gactctactc cctcagcagc   600
gtggtgaccg tgccctccag cagcttgggc acccagacct acatctgcaa cgtgaatcac   660
aagcccagca acaccaaggt ggacaagaaa gttgagccca atcttgtgac aaaaactcac   720
acatgcccac cgtgcccagc acctgaactc ctggggggac cgtcagtctt cctcttcccc   780
```

```
ccaaaaccca aggacaccct catgatctcc cggacccctg aggtcacatg cgtggtggtg      840
gacgtgagcc acgaagaccc tgaggtcaag ttcaactggt acgtggacgg cgtggaggtg      900
cataatgcca agacaaagcc gcgggaggag cagtacaaca gcacgtaccg tgtggtcagc      960
gtcctcaccg tcctgcacca ggactggctg aatggcaagg agtacaagtg caaggtctcc     1020
aacaaagccc tcccagcccc catcgagaaa accatctcca aagccaaagg cagccccga      1080 gaaccacagg tgtacaccct gcccccatcc cgggatgagc tgaccaagaa ccaggtcagc     1140
ctgacctgcc tggtcaaagg cttctatccc agcgacatcg ccgtggagtg ggagagcaat     1200
gggcagccgg agaacaacta caagaccacg cctcccgtgc tggactccga cggctccttc     1260
ttcctctaca gcaagctcac cgtggacaag agcaggtggc agcaggggaa cgtcttctca     1320
tgctccgtga tgcatgaggc tctgcacaac cactacacgc agaagagcct ctccctgtct     1380
ccgggtaaat ga                                                         1392

<210> SEQ ID NO 12
<211> LENGTH: 342
<212> TYPE: DNA
<213> ORGANISM: Mus musculus

<400> SEQUENCE: 12
gaggtgcacc tggtggagtc tgggggaggc ttagtgaagc ctggagggtc cctgaaactc       60
tcctgtgcag cctctggatt cactttcagt aactatgcca tgtcttgggt tcgccagact      120
ccagagaaga gctggagtg gtcgcagcc attaataata atggtgatga cacctactat       180
ttagacactg tgaaggaccg attcaccatc tccagagaca tgccaagaa caccctgtac      240 ctgcaaatga gcagtctgag gtctgaggac acagccctgt attactgtgt aagacaaggg     300
ggggcttact ggggccaagg gactctggtc actgtctctg ca                         342

<210> SEQ ID NO 13
<211> LENGTH: 1413
<212> TYPE: DNA
<213> ORGANISM: Mus musculus

<400> SEQUENCE: 13
atgggatgga actggatctt tattttaatc ctgtcagtaa ctacaggtgt ccactctgag       60
gtccagctgc agcagtctgg acctgagctg gtgaagcctg ggcttcagt gaagatatcc      120 tgcaaggctt ctggttactc attcactggc tactacatgc actgggtgaa gcaaagtcct      180
gaaaagagcc ttgagtggat tggagagatt aatcctagca ctggtggtac tacctacaac      240
cagaagttca aggccaaggc cacattgact gtagacaaat cctccagcac agcctacatg      300
cagctcaaga gcctgacatc tgaggactct gcagtctatt actgtgcaag gaggggcgga      360
ttaactggga cgagcttctt tgcttactgg ggccaaggga ctctggtcac tgtctctgca      420
gctagcacca agggcccatc ggtcttcccc ctggcaccct cctccaagag cacctctggg      480
ggcacagcgg ccctgggctg cctggtcaag gactacttcc ccgaaccggt gacggtgtcg      540
tggaactcag gcgccctgac cagcggcgtg cacaccttcc cggctgtcct acagtcctca      600
ggactctact ccctcagcag cgtggtgacc gtgccctcca gcagcttggg cacccagacc      660
tacatctgca acgtgaatca caagcccagc aacaccaagg tggacaagaa agttgagccc      720
aaatcttgtg acaaaactca cacatgccca ccgtgcccag cacctgaact cctggggga       780 ccgtcagtct tcctcttccc cccaaaaccc aaggacaccc tcatgatctc ccggacccct      840
gaggtcacat gcgtggtggt ggacgtgagc cacgaagacc ctgaggtcaa gttcaactgg      900
```

```
tacgtggacg cgtggaggt gcataatgcc aagacaaagc cgcggggagga gcagtacaac    960 agcacgtacc gtgtggtcag cgtcctcacc gtcctgcacc aggactggct gaatggcaag   1020
gagtacaagt gcaaggtctc caacaaagcc ctcccagccc ccatcgagaa aaccatctcc   1080
aaagccaaag ggcagccccg agaaccacag gtgtacaccc tgcccccatc ccgggatgag   1140
ctgaccaaga accaggtcag cctgacctgc ctggtcaaag gcttctatcc cagcgacatc   1200
gccgtggagt gggagagcaa tgggcagccg gagaacaact acaagaccac gcctcccgtg   1260
ctggactccg acggctcctt cttcctctac agcaagctca ccgtggacaa gagcaggtgg   1320
cagcagggga acgtcttctc atgctccgtg atgcatgagg ctctgcacaa ccactacacg   1380
cagaagagcc tctccctgtc tccgggtaaa tga                               1413

<210> SEQ ID NO 14
<211> LENGTH: 354
<212> TYPE: DNA
<213> ORGANISM: Mus musculus

<400> SEQUENCE: 14
caggtcactc tgaaagagtc tggccctggg atattgcagc cctcccagac cctcagtctg     60
acttgttctt tctctgggtt ttcactgagc acttatggta tgggtgtagg ttggattcgt    120
cagccttcag ggatgggtct ggagtggctg gccaacattt ggtggtatga tgctaagtac    180
tataactctg acctgaagag ccggctcaca atctccaagg atacctccaa caaccaggtg    240
ttcctcaaga tctccagtgt ggacacttca gatactgcca catactactg tgctcaaatg    300
ggactggcct ggtttgctta ctggggccaa gggactctgg tcactgtctc tgca          354

<210> SEQ ID NO 15
<211> LENGTH: 354
<212> TYPE: DNA
<213> ORGANISM: Mus musculus

<400> SEQUENCE: 15
caggtcactc tgaaagagtc tggccctggg atattgcagc cctcccagac cctcagtctg     60
acttgttctt tctctggggtt ttcactgagc atttatggta tgggtgtagg ttggattcgt    120
cagccttcag ggaagggtct ggagtggctg gccaacattt ggtggaatga tgataagtac    180
tataactcag ccctgaagag ccggctcaca atctccaagg atacctccaa caaccaggta    240
ttcctcaaga tctccagtgt ggacactgca gatactgcca catactactg tgctcaaata    300
ggttacttct actttgacta ctggggccaa ggcaccactc tcacagtctc ctca          354

<210> SEQ ID NO 16
<211> LENGTH: 1416
<212> TYPE: DNA
<213> ORGANISM: Mus musculus

<400> SEQUENCE: 16
atgaacttcg ggctcacctt gattttcctc gtccttactt taaaaggtgt ccagtgtgag     60
gtgcagctgg tggagtctgg gggagactta gtgaagcctg agggacccct gaaactctcc    120
tgtgcagcct ctggatccac tttcagtaac tatgccatgt cttgggttcg ccagactcca    180
gagaagaggc tggagtgggt cgcagccatt gatagtaatg gaggtaccac ctactatcca    240
gacactatga aggaccgatt caccatttcc agagacaatg ccaagaacac cctgtacctg    300
caaatgaaca gtctgaggtc tgaagacaca gccttttatc actgtacaag acataatgga    360
gggtatgaaa actacggctg gtttgcttac tggggccaag ggactctggt cactgtctct    420
```

```
gcagctagca ccaagggccc atcggtcttc ccctggcac cctcctccaa gagcacctct   480
gggggcacag cggccctggg ctgcctggtc aaggactact tccccgaacc ggtgacggtg   540
tcgtggaact caggcgccct gaccagcggc gtgcacacct tcccggctgt cctacagtcc   600
tcaggactct actccctcag cagcgtggtg accgtgccct ccagcagctt gggcacccag   660
acctacatct gcaacgtgaa tcacaagccc agcaacacca aggtggacaa gaaagttgag   720
cccaaatctt gtgacaaaac tcacacatgc ccaccgtgcc cagcacctga actcctgggg   780
ggaccgtcag tcttcctctt cccccaaaa cccaaggaca cctcatgat ctcccggacc   840 cctgaggtca catgcgtggt ggtggacgtg agccacgaag accctgaggt caagttcaac   900
tggtacgtgg acggcgtgga ggtgcataat gccaagacaa agccgcggga ggagcagtac   960
aacagcacgt accgtgtggt cagcgtcctc accgtcctgc accaggactg gctgaatggc  1020
aaggagtaca gtgcaaggt ctccaacaaa gccctcccag cccccatcga aaaaccatc   1080 tccaaagcca agggcagcc ccgagaacca caggtgtaca ccctgccccc atcccgggat  1140
gagctgacca gaaccaggt cagcctgacc tgcctggtca aaggcttcta tcccagcgac  1200
atcgccgtgg agtgggagag caatgggcag ccggagaaca actacaagac cacgcctccc  1260
gtgctggact ccgacggctc cttcttcctc tacagcaagc tcaccgtgga caagagcagg  1320
tggcagcagg ggaacgtctt ctcatgctcc gtgatgcatg aggctctgca caaccactac  1380
acgcagaaga gcctctccct gtctccgggt aaatga                          1416

<210> SEQ ID NO 17
<211> LENGTH: 366
<212> TYPE: DNA
<213> ORGANISM: Mus musculus

<400> SEQUENCE: 17
gaggtgcagc tggtggagtc tgggggagac ttagtgaagc ctggagggtc cctgaaactc    60
tcctgtgcag cctctggatt cactttcagt agctatgcca tgtcttgggt tcgccagact   120
ccagagaaga ggctggagtg ggtcgcagcc attaatagta atggaggtac cacctactat   180
ccagacacta tgaaggaccg attcaccatc tccagagaca atgccaagaa caccctgtac   240
ctgcaaatga gcagtctgag gtctgaagac tcagccttgt attactgtac aagacataat   300
ggagggtatg aaaactacgg ctggtttgct tactggggcc aagggactct ggtcactgtc   360
tctgca                                                              366

<210> SEQ ID NO 18
<211> LENGTH: 1413
<212> TYPE: DNA
<213> ORGANISM: Mus musculus

<400> SEQUENCE: 18
atggaatcta actggatact tcctttatt ctgtcggtag cttcaggggt ctactcagag    60
gttcagctcc agcagtctgg gactgtgctg gcaaggcctg ggcttcagt gaagatgtcc   120 tgcaaggctt ctggctacac ctttactggc tactggatgc gctgggtaaa acagaggcct   180
ggacagggtc tggaatggat tggcgctatt tatcctggaa atagtgatac aacatacaac   240
cagaagttca agggcaaggc caaactgact gcagtcacat ctgtcagcac tgcctacatg   300
gaactcagca gcctgacaaa tgaggactct gcggtctatt actgttcaag atcggggggac   360 ctaactgggg ggtttgctta ctggggccaa gggactctgg tcactgtctc tacagccaaa   420
gctagcacca agggcccatc ggtcttcccc ctggcaccct cctccaagag cacctctggg   480
```

```
ggcacagcgg ccctgggctg cctggtcaag gactacttcc ccgaaccggt gacggtgtcg      540
tggaactcag gcgccctgac cagcggcgtg cacaccttcc cggctgtcct acagtcctca      600
ggactctact ccctcagcag cgtggtgacc gtgccctcca gcagcttggg cacccagacc      660
tacatctgca acgtgaatca caagcccagc aacaccaagg tggacaagaa agttgagccc      720
aaatcttgtg acaaaactca cacatgccca ccgtgcccag cacctgaact cctgggggga      780
ccgtcagtct tcctcttccc cccaaaaccc aaggacaccc tcatgatctc ccggacccct      840
gaggtcacat gcgtggtggt ggacgtgagc cacgaagacc ctgaggtcaa gttcaactgg      900
tacgtggacg gcgtggaggt gcataatgcc aagacaaagc cgcgggagga gcagtacaac      960
agcacgtacc gtgtggtcag cgtcctcacc gtcctgcacc aggactggct gaatggcaag     1020
gagtacaagt gcaaggtctc caacaaagcc ctcccagccc ccatcgagaa aaccatctcc     1080
aaagccaaag ggcagccccg agaaccacag gtgtacaccc tgcccccatc ccgggatgag     1140
ctgaccaaga accaggtcag cctgacctgc ctggtcaaag gcttctatcc cagcgacatc     1200
gccgtggagt gggagagcaa tgggcagccg gagaacaact acaagaccac gcctcccgtg     1260
ctggactccg acggctcctt cttcctctac agcaagctca ccgtggacaa gagcaggtgg     1320
cagcagggga acgtcttctc atgctccgtg atgcatgagg ctctgcacaa ccactacacg     1380
cagaagagcc tctccctgtc tccgggtaaa tga                                  1413

<210> SEQ ID NO 19
<211> LENGTH: 357
<212> TYPE: DNA
<213> ORGANISM: Mus musculus

<400> SEQUENCE: 19
gaggttcagc tccagcagtc tgggactgtg ctggcaaggc ctggggcttc agtgaagatg       60
tcctgcaagg cttctggcta cacctttacc ggctactgga tgcactgggt aaaacagagg      120
cctggacagg gtctggaatg gattggcgct atttatcctg gaaatagtga tactaactac      180
aaccagaagt tcaagggcaa ggccaaactg actgcagtca catctgccag cactgcctac      240
atggagctca gcagcctgac aaatgaggac gctgcggtct atcactgtac aagatcgggg      300
gacctaactg gggggcttgc ttactggggc caagggactc tggtcactgt ctctgca        357

<210> SEQ ID NO 20
<211> LENGTH: 372
<212> TYPE: DNA
<213> ORGANISM: Mus musculus

<400> SEQUENCE: 20
caggtccagc tgcagcagcc tggggctgaa ctggtgaagc ctggggcttc agtgaaactg       60
tcctgcaagg cttctggata caccttcact agctactgga tgcattgggt gaagcagagg      120
cctggacaag gccttgagtg gatcggagag attgatcctt ctgatagtta tacttactac      180
aatcaaaagt tcagggggcaa ggccacattg actgtagaca atcctccaa cacagcctac      240 atgcaactca gcagcctgac atctgaggac tctgcggtct attactgttc aagatcaaat      300
ctgggtgatg gtcactaccg gtttcctgcg tttccttact ggggccaagg gactctggtc      360
actgtctctg ca                                                          372

<210> SEQ ID NO 21
<211> LENGTH: 372
<212> TYPE: DNA
<213> ORGANISM: Mus musculus
```

<400> SEQUENCE: 21

```
caggtccaac tgcagcagcc tggggctgaa ctggtgaaac tggggcttc agtgaagctg      60
tcctgcaagg cttctggcta caccttcacc agctactgga tgcactgggt gaaacagagg    120
cctggacaag gccttgaatg gattggataca attgaccctt ctgatagtga aactcactac   180
aatctacagt tcaaggacac ggccacattg actgtagaca atcctccag cacagcctac     240
atgcagctca gcagcctgac atctgaggac tctgcggtct attattgtat aagaggcgcc    300
ttctatagtt cctatagtta ctgggcctgg tttgcttact ggggccaagg gactctggtc    360
actgtctctg ca                                                        372
```

<210> SEQ ID NO 22
<211> LENGTH: 463
<212> TYPE: PRT
<213> ORGANISM: Mus musculus

<400> SEQUENCE: 22

```
Met Asn Phe Gly Leu Thr Leu Ile Phe Leu Val Leu Thr Leu Lys Gly
1               5                   10                  15

Val Gln Cys Glu Val Gln Leu Val Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Arg Tyr Ala Met Ser Trp Val Arg Gln Ile Pro Glu Lys Ile Leu
    50                  55                  60

Glu Trp Val Ala Ala Ile Asp Ser Ser Gly Gly Asp Thr Tyr Tyr Leu
65                  70                  75                  80

Asp Thr Val Lys Asp Arg Phe Thr Ile Ser Arg Asp Asn Ala Asn Asn
                85                  90                  95

Thr Leu His Leu Gln Met Arg Ser Leu Arg Ser Glu Asp Thr Ala Leu
            100                 105                 110

Tyr Tyr Cys Val Arg Gln Gly Gly Ala Tyr Trp Gly Gln Gly Thr Leu
        115                 120                 125

Val Thr Val Ser Ala Ala Ser Thr Lys Gly Pro Ser Val Phe Pro Leu
    130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Gln Thr Tyr Ile Cys Asn Val Asn His Lys Pro Ser Asn
    210                 215                 220

Thr Lys Val Asp Lys Lys Val Glu Pro Lys Ser Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
```

```
                     290                 295                 300
Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
                340                 345                 350

Ser Lys Ala Lys Gly Gln Pro Arg Glu Pro Gln Val Tyr Thr Leu Pro
                355                 360                 365

Pro Ser Arg Asp Glu Leu Thr Lys Asn Gln Val Ser Leu Thr Cys Leu
                370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
                420                 425                 430

Trp Gln Gln Gly Asn Val Phe Ser Cys Ser Val Met His Glu Ala Leu
                435                 440                 445

His Asn His Tyr Thr Gln Lys Ser Leu Ser Leu Ser Pro Gly Lys
                450                 455                 460

<210> SEQ ID NO 23
<211> LENGTH: 114
<212> TYPE: PRT
<213> ORGANISM: Mus musculus

<400> SEQUENCE: 23

Glu Val His Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
                20                  25                  30

Ala Met Ser Trp Val Arg Gln Thr Pro Glu Lys Arg Leu Glu Trp Val
                35                  40                  45

Ala Ala Ile Asn Asn Asn Gly Asp Asp Thr Tyr Tyr Leu Asp Thr Val
                50                  55                  60

Lys Asp Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Val Arg Gln Gly Gly Ala Tyr Trp Gly Gln Gly Thr Leu Val Thr Val
                100                 105                 110

Ser Ala

<210> SEQ ID NO 24
<211> LENGTH: 470
<212> TYPE: PRT
<213> ORGANISM: Mus musculus

<400> SEQUENCE: 24

Met Gly Trp Asn Trp Ile Phe Ile Leu Ile Leu Ser Val Thr Thr Gly
1               5                   10                  15

Val His Ser Glu Val Gln Leu Gln Gln Ser Gly Pro Glu Leu Val Lys
                20                  25                  30

Pro Gly Ala Ser Val Lys Ile Ser Cys Lys Ala Ser Gly Tyr Ser Phe
                35                  40                  45
```

-continued

Thr Gly Tyr Tyr Met His Trp Val Lys Gln Ser Pro Glu Lys Ser Leu
    50                  55                  60

Glu Trp Ile Gly Glu Ile Asn Pro Ser Thr Gly Thr Thr Tyr Asn
65                  70                  75                  80

Gln Lys Phe Lys Ala Lys Ala Thr Leu Thr Val Asp Lys Ser Ser
                85                  90                  95

Thr Ala Tyr Met Gln Leu Lys Ser Leu Thr Ser Glu Asp Ser Ala Val
            100                 105                 110

Tyr Tyr Cys Ala Arg Arg Gly Gly Leu Thr Gly Thr Ser Phe Phe Ala
        115                 120                 125

Tyr Trp Gly Gln Gly Thr Leu Val Thr Val Ser Ala Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

-continued

<210> SEQ ID NO 25
<211> LENGTH: 118
<212> TYPE: PRT
<213> ORGANISM: Mus musculus

<400> SEQUENCE: 25

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Gly Trp Ile Arg Gln Pro Ser Gly Met Gly Leu Glu
        35                  40                  45

Trp Leu Ala Asn Ile Trp Trp Tyr Asp Ala Lys Tyr Tyr Asn Ser Asp
    50                  55                  60

Leu Lys Ser Arg Leu Thr Ile Ser Lys Asp Thr Ser Asn Asn Gln Val
65                  70                  75                  80

Phe Leu Lys Ile Ser Ser Val Asp Thr Ser Asp Thr Ala Thr Tyr Tyr
                85                  90                  95

Cys Ala Gln Met Gly Leu Ala Trp Phe Ala Tyr Trp Gly Gln Gly Thr
            100                 105                 110

Leu Val Thr Val Ser Ala
        115

<210> SEQ ID NO 26
<211> LENGTH: 118
<212> TYPE: PRT
<213> ORGANISM: Mus musculus

<400> SEQUENCE: 26

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Ile Tyr
            20                  25                  30

Gly Met Gly Val Gly Trp Ile Arg Gln Pro Ser Gly Lys Gly Leu Glu
        35                  40                  45

Trp Leu Ala Asn Ile Trp Trp Asn Asp Lys Tyr Tyr Asn Ser Ala
    50                  55                  60

Leu Lys Ser Arg Leu Thr Ile Ser Lys Asp Thr Ser Asn Asn Gln Val
65                  70                  75                  80

Phe Leu Lys Ile Ser Ser Val Asp Thr Ala Asp Thr Ala Thr Tyr Tyr
                85                  90                  95

Cys Ala Gln Ile Gly Tyr Phe Tyr Phe Asp Tyr Trp Gly Gln Gly Thr
            100                 105                 110

Thr Leu Thr Val Ser Ser
        115

<210> SEQ ID NO 27
<211> LENGTH: 471
<212> TYPE: PRT
<213> ORGANISM: Mus musculus

<400> SEQUENCE: 27

Met Asn Phe Gly Leu Thr Leu Ile Phe Leu Val Leu Thr Leu Lys Gly
1               5                   10                  15

Val Gln Cys Glu Val Gln Leu Val Glu Ser Gly Gly Asp Leu Val Lys
            20                  25                  30

Pro Gly Gly Thr Leu Lys Leu Ser Cys Ala Ala Ser Gly Ser Thr Phe

-continued

```
            35                  40                  45
Ser Asn Tyr Ala Met Ser Trp Val Arg Gln Thr Pro Glu Lys Arg Leu
 50                  55                  60

Glu Trp Val Ala Ala Ile Asp Ser Asn Gly Gly Thr Thr Tyr Tyr Pro
 65                  70                  75                  80

Asp Thr Met Lys Asp Arg Phe Thr Ile Ser Arg Asp Asn Ala Lys Asn
                     85                  90                  95

Thr Leu Tyr Leu Gln Met Asn Ser Leu Arg Ser Glu Asp Thr Ala Phe
                100                 105                 110

Tyr His Cys Thr Arg His Asn Gly Gly Tyr Glu Asn Tyr Gly Trp Phe
            115                 120                 125

Ala Tyr Trp Gly Gln Gly Thr Leu Val Thr Val Ser Ala Ala Ser Thr
130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
            195                 200                 205

Val Val Thr Val Pro Ser Ser Ser Leu Gly Thr Gln Thr Tyr Ile Cys
210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
                340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Asp Glu Leu Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
450                 455                 460
```

```
Leu Ser Leu Ser Pro Gly Lys
465                 470

<210> SEQ ID NO 28
<211> LENGTH: 122
<212> TYPE: PRT
<213> ORGANISM: Mus musculus

<400> SEQUENCE: 28

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ala Ile Asn Ser Asn Gly Gly Thr Thr Tyr Tyr Pro Asp Thr Met
    50                  55                  60

Lys Asp Arg Phe Thr Ile Ser Arg Asp Asn Ala Lys Asn Thr Leu Tyr
65                  70                  75                  80

Leu Gln Met Ser Ser Leu Arg Ser Glu Asp Ser Ala Leu Tyr Tyr Cys
                85                  90                  95

Thr Arg His Asn Gly Gly Tyr Glu Asn Tyr Gly Trp Phe Ala Tyr Trp
            100                 105                 110

Gly Gln Gly Thr Leu Val Thr Val Ser Ala
        115                 120

<210> SEQ ID NO 29
<211> LENGTH: 470
<212> TYPE: PRT
<213> ORGANISM: Mus musculus

<400> SEQUENCE: 29

Met Glu Ser Asn Trp Ile Leu Pro Phe Ile Leu Ser Val Ala Ser Gly
1               5                   10                  15

Val Tyr Ser Glu Val Gln Leu Gln Gln Ser Gly Thr Val Leu Ala Arg
            20                  25                  30

Pro Gly Ala Ser Val Lys Met Ser Cys Lys Ala Ser Gly Tyr Thr Phe
        35                  40                  45

Thr Gly Tyr Trp Met Arg Trp Val Lys Gln Arg Pro Gly Gln Gly Leu
    50                  55                  60

Glu Trp Ile Gly Ala Ile Tyr Pro Gly Asn Ser Asp Thr Thr Tyr Asn
65                  70                  75                  80

Gln Lys Phe Lys Gly Lys Ala Lys Leu Thr Ala Val Thr Ser Val Ser
                85                  90                  95

Thr Ala Tyr Met Glu Leu Ser Ser Leu Thr Asn Glu Asp Ser Ala Val
            100                 105                 110

Tyr Tyr Cys Ser Arg Ser Gly Asp Leu Thr Gly Gly Phe Ala Tyr Trp
        115                 120                 125

Gly Gln Gly Thr Leu Val Thr Val Ser Thr Ala Lys Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
```

```
              195                 200                 205
Val Thr Val Pro Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Asp
            275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 30
<211> LENGTH: 119
<212> TYPE: PRT
<213> ORGANISM: Mus musculus

<400> SEQUENCE: 30

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Gly Tyr
            20                  25                  30

Trp Met His Trp Val Lys Gln Arg Pro Gly Gln Gly Leu Glu Trp Ile
        35                  40                  45

Gly Ala Ile Tyr Pro Gly Asn Ser Asp Thr Asn Tyr Asn Gln Lys Phe
    50                  55                  60

Lys Gly Lys Ala Lys Leu Thr Ala Val Thr Ser Ala Ser Thr Ala Tyr
65                  70                  75                  80

Met Glu Leu Ser Ser Leu Thr Asn Glu Asp Ala Ala Val Tyr His Cys
                85                  90                  95

Thr Arg Ser Gly Asp Leu Thr Gly Gly Leu Ala Tyr Trp Gly Gln Gly
```

Thr Leu Val Thr Val Ser Ala
        115

<210> SEQ ID NO 31
<211> LENGTH: 124
<212> TYPE: PRT
<213> ORGANISM: Mus musculus

<400> SEQUENCE: 31

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asp Pro Ser Asp Ser Tyr Thr Tyr Tyr Asn Gln Lys Phe
    50                  55                  60

Arg Gly Lys Ala Thr Leu Thr Val Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ser Arg Ser Asn Leu Gly Asp Gly His Tyr Arg Phe Pro Ala Phe Pro
            100                 105                 110

Tyr Trp Gly Gln Gly Thr Leu Val Thr Val Ser Ala
        115                 120

<210> SEQ ID NO 32
<211> LENGTH: 124
<212> TYPE: PRT
<213> ORGANISM: Mus musculus

<400> SEQUENCE: 32

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Thr Ile Asp Pro Ser Asp Ser Glu Thr His Tyr Asn Leu Gln Phe
    50                  55                  60

Lys Asp Thr Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ile Arg Gly Ala Phe Tyr Ser Ser Tyr Ser Tyr Trp Ala Trp Phe Ala
            100                 105                 110

Tyr Trp Gly Gln Gly Thr Leu Val Thr Val Ser Ala
        115                 120

<210> SEQ ID NO 33
<211> LENGTH: 717
<212> TYPE: DNA
<213> ORGANISM: Mus musculus

<400> SEQUENCE: 33
atgagtcctg cccagttcct gtttctgtta gtgctctgga ttcgggaaac caacggtgat      60
gttgtgatga cccagactcc actcactttg tcggttacca ttggacaacc agcctccatc     120

```
tcttgcaagt caagtcagag cctcttagat agtgatggaa agacatattt gaattggttg      180
ttacagaggc caggccagtc tccaaagcgc ctaatctatc tggtgtctaa attggactct      240
ggagcccctg acaggttcac tggcagtgga tcagggacag atttcacact gaaaatcagt      300
agagtggagg ctgaggattt gggaatttat tattgctggc aaggtacaca ttttccgctc      360
acgttcggtg ctgggaccaa gctggagctg aaacgtacgg tggctgcacc atctgtcttc      420
atcttcccgc catctgatga gcagttgaaa tctggaactg cctctgttgt gtgcctgctg      480
aataacttct atcccagaga ggccaaagta cagtggaagg tggataacgc cctccaatcg      540
ggtaactccc aggagagtgt cacagagcag gacagcaagg acagcaccta cagcctcagc      600
agcaccctga cgctgagcaa agcagactac gagaaacaca agtctacgc ctgcgaagtc       660 acccatcagg gcctgagctc gcccgtcaca aagagcttca caggggaga gtgttga          717
```

```
<210> SEQ ID NO 34
<211> LENGTH: 336
<212> TYPE: DNA
<213> ORGANISM: Mus musculus

<400> SEQUENCE: 34
gatgttgtga tgacccagtc tccactcact ttgtcgatta ccattggaca accagcctcc      60
atctcttgca gtcaagtca gagcctctta gatagtgatg aaagacata tttgaattgg       120 ttgttacaga ggccaggcca gtctccaaag cgcctaatct atctggtgtc taaactggac      180
tctggagtcc ctgacaggtt cactggcagt ggatcaggga cagatttctc actgaaaatc      240
agcagagtgg aggctgagga tttgggaatt tattattgct ggcaaggtac acattttccg      300
ctcacgttcg gtgctgggac caagctggag ctgaaa                                336
```

```
<210> SEQ ID NO 35
<211> LENGTH: 717
<212> TYPE: DNA
<213> ORGANISM: Mus musculus

<400> SEQUENCE: 35
atgagtcctg tccagttcct gtttctgtta atgctctgga ttcaggaaac caacggtgat      60
gttgtgatga cccagactcc actgtctttg tcggttacca ttggacaacc agcctctatc      120
tcttgcaagt caagtcagag cctcttatat agtaatggaa agacatattt gaattggtta      180
caacagaggc tggccaggc tccaaagcac ctaatgtatc aggtgtccaa actggaccct       240
ggcatccctg acaggttcag tggcagtgga tcagaaacag attttacact aaaaatcagc      300
agagtggagg ctgaagattt gggagtttat tactgcttgc aaagtacata ttatccgctc      360
acgttcggtg ctgggaccaa gctggagctg aaacgtacgg tggctgcacc atctgtcttc      420
atcttcccgc catctgatga gcagttgaaa tctggaactg cctctgttgt gtgcctgctg      480
aataacttct atcccagaga ggccaaagta cagtggaagg tggataacgc cctccaatcg      540
ggtaactccc aggagagtgt cacagagcag gacagcaagg acagcaccta cagcctcagc      600
agcaccctga cgctgagcaa agcagactac gagaaacaca agtctacgc ctgcgaagtc       660 acccatcagg gcctgagctc gcccgtcaca aagagcttca caggggaga gtgttga          717
```

```
<210> SEQ ID NO 36
<211> LENGTH: 324
<212> TYPE: DNA
<213> ORGANISM: Mus musculus

<400> SEQUENCE: 36
```

```
gacatcaaga tgacccagtc tccatcttcc atgtatgcat ctctaggaga gagagtcact    60
atcacttgca aggcgagtca ggacattaat aactatttaa gctggttcca gcagaaacca   120
gggaaatctc ctaagaccct gatctatcgt gcaaacagat tggtagatgg ggtcccatca   180
aggttcagtg gcagtggatc tgggcaagat tattctctca ccatcagcag cctggagtat   240
gaagatatgg gaattaatta ttgtctacag tgtgatgagt ttcctccgtg gacgttcggt   300
ggaggcacca agctggaaat caaa                                          324
```

`<210>` SEQ ID NO 37
`<211>` LENGTH: 336
`<212>` TYPE: DNA
`<213>` ORGANISM: Mus musculus

`<400>` SEQUENCE: 37

```
gatgttgtga tgacccaaac tccactctcc ctgcctgtca gtcttggaga tcaagcctcc    60
atctcttgca gatctagtca gagccttgta cacagtaatg gaaacaccta tttacattgg   120
tacctgcaga agccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tatttctgct ctcaaagtac acatgttccg   300
tggacgttcg gtggaggcac caagctggaa atcaaa                             336
```

`<210>` SEQ ID NO 38
`<211>` LENGTH: 705
`<212>` TYPE: DNA
`<213>` ORGANISM: Mus musculus

`<400>` SEQUENCE: 38

```
atgagaccct ccattcagtt cctggggctc ttgttgttct ggcttcatgg tgttcagtgt    60
gacatccaga tgacacagtc tccatcctca ctgtctgcat ctctgggagg caaagtcacc   120
atcacttgca aggcaagtca ggacattaac aagaatatag tttggtacca acacaagcct   180
ggaaaaggtc ctaggctgct catatggtac acatctacat tacagccagg catcccatca   240
aggttcagtg gaagtgggtc tgggagagat tattccttca gcatcagcaa cctggagcct   300
gaagatattg caacttatta ctgtctacag tatgataatc ttccacggac gttcggtgga   360
ggcaccaaac tggaaatcaa acgtacggtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgccc tccaatcggg taactcccag   540
gagagtgtca cagagcagga cagcaaggac agcacctaca gcctcagcag caccctgacg   600
ctgagcaaag cagactacga gaaacacaaa gtctacgcct gcgaagtcac ccatcagggc   660
ctgagctcgc ccgtcacaaa gagcttcaac aggggagagt gttga                   705
```

`<210>` SEQ ID NO 39
`<211>` LENGTH: 321
`<212>` TYPE: DNA
`<213>` ORGANISM: Mus musculus

`<400>` SEQUENCE: 39

```
gacatccaga tgacacagtc tccatcctca ctgtctgcat ctctgggagg caaagtcacc    60
atcacttgca aggcaagtca ggacattaac aagaatataa tttggtacca acacaagcct   120
ggaaaaggtc ctaggctgct catatggtac acatctacat tacagccagg catcccatca   180
aggttcagtg gaagtgggtc tgggagagat tattccttca gcatcagcaa cctggagcct   240
```

```
gaagatattg caacttatta ctgtctacag tatgataatc ttccacggac gttcggtgga    300
ggcaccaagc tggaaatcaa a                                              321
```

<210> SEQ ID NO 40
<211> LENGTH: 720
<212> TYPE: DNA
<213> ORGANISM: Mus musculus

<400> SEQUENCE: 40

```
atgaggttct ctgctcagct tctggggctg cttgtgctct ggatccctgg atccactgca     60
gatattgtga tgacgcaggc tgcattctcc aatccagtca ctcttggaac atcaacttcc    120
atctcctgca ggtctagtaa gagtctccta catagtaatg gcatcactta tttgtattgg    180
tatctgcaga agccaggcca gtctcctcag ctcctgattt atcagatgtc caaccttgcc    240
tcaggagtcc cagacaggtt cagtagcagt gggtcaggaa ctgatttcac actgagaatc    300
agcagagtgg aggctgagga tgtgggtgtt tattactgtg ctcaaaatct agaacttccg    360
tatacgttcg gatcggggac caagctggaa ataaaacgta cggtggctgc accatctgtc    420
ttcatcttcc cgccatctga tgagcagttg aaatctggaa ctgcctctgt tgtgtgcctg    480
ctgaataact tctatcccag agaggccaaa gtacagtgga aggtggataa cgccctccaa    540
tcgggtaact cccaggagag tgtcacagag caggacagca aggacagcac ctacagcctc    600
agcagcaccc tgacgctgag caaagcagac tacgagaaac acaaagtcta cgcctgcgaa    660
gtcacccatc agggcctgag ctcgcccgtc acaaagagct caacaggggg agagtgttga    720
```

<210> SEQ ID NO 41
<211> LENGTH: 336
<212> TYPE: DNA
<213> ORGANISM: Mus musculus

<400> SEQUENCE: 41

```
gatattgtga tgacgcaggc tgcattctcc aatccagtca ctcttggaac atcagcttcc     60
atctcctgca ggtctagtaa gagtctccta catagtaatg gcatcactta tttgtattgg    120
tttctgcaga agccaggcca gtctcctcag ctcctgattt atcagatgtc caaccttgcc    180
tcaggagtcc cagacaggtt cagtagcagt gggtcaggaa ctgatttcac actgagaatc    240
agcagagtgg aggctgagga tgtgggtgtt tattactgtg ctcaaaatct agaacttccg    300
tatacgttcg gatcggggac caagctggaa ataaaa                              336
```

<210> SEQ ID NO 42
<211> LENGTH: 321
<212> TYPE: DNA
<213> ORGANISM: Mus musculus

<400> SEQUENCE: 42

```
gatattgtgc taactcagtc tccagccacc ctgtctgtga ctccaggaga cagagtcagt     60
ctttcctgca gggccagcca tagtattagc aacttcctac actggtatcc acaaaaatca    120
catgagtctc caaggcttct catcaagtat gcttcccagt ccatctctgg gatcccctcc    180
aggttcagtg gcaatggatc aggacagat ttcactctca gtatcaacag tgtggagact    240
gaagattttg gaatgtattt ctgtcaacag agtaacatct ggtcgctcac gttcggtgct    300
gggaccaagc tggagctgaa a                                              321
```

<210> SEQ ID NO 43
<211> LENGTH: 333

```
<212> TYPE: DNA
<213> ORGANISM: Mus musculus

<400> SEQUENCE: 43
gacattgtgc tcacccaatc tccaacttct ttggctgtgt ctctagggca gagtgtcacc      60
atctcctgca gagccagtga agtgttgaa  tattatggca ctagtttaat gcagtggtac     120
caacagaaac caggacagcc acccaaactc ctcatctatg gtgcatccaa cgtagaatct     180
ggggtccctg ccaggtttag tggcagtggg tctgggacag acttcagcct caacatccat     240
cctgtggagg aggatgatat tgcaatgtat ttctgtcagc aaagtaggaa ggttccgtat     300
acgttcggat cggggaccaa gctggaaata aaa                                   333

<210> SEQ ID NO 44
<211> LENGTH: 238
<212> TYPE: PRT
<213> ORGANISM: Mus musculus

<400> SEQUENCE: 44

Met Ser Pro Ala Gln Phe Leu Phe Leu Leu Val Leu Trp Ile Arg Glu
1               5                   10                  15

Thr Asn Gly Asp Val Val Met Thr Gln Thr Pro Leu Thr Leu Ser Val
            20                  25                  30

Thr Ile Gly Gln Pro Ala Ser Ile Ser Cys Lys Ser Ser Gln Ser Leu
        35                  40                  45

Leu Asp Ser Asp Gly Lys Thr Tyr Leu Asn Trp Leu Leu Gln Arg Pro
    50                  55                  60

Gly Gln Ser Pro Lys Arg Leu Ile Tyr Leu Val Ser Lys Leu Asp Ser
65                  70                  75                  80

Gly Ala Pro Asp Arg Phe Thr Gly Ser Gly Ser Gly Thr Asp Phe Thr
                85                  90                  95

Leu Lys Ile Ser Arg Val Glu Ala Glu Asp Leu Gly Ile Tyr Tyr Cys
            100                 105                 110

Trp Gln Gly Thr His Phe Pro Leu Thr Phe Gly Ala Gly Thr Lys Leu
        115                 120                 125

Glu Leu Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 45
<211> LENGTH: 112
<212> TYPE: PRT
<213> ORGANISM: Mus musculus

<400> SEQUENCE: 45

Asp Val Val Met Thr Gln Ser Pro Leu Thr Leu Ser Ile Thr Ile Gly
1               5                   10                  15
```

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Ser Leu Lys Ile
65                  70                  75                  80

Ser Arg Val Glu Ala Glu Asp Leu Gly Ile Tyr Tyr Cys Trp Gln Gly
                85                  90                  95

Thr His Phe Pro Leu Thr Phe Gly Ala Gly Thr Lys Leu Glu Leu Lys
            100                 105                 110

<210> SEQ ID NO 46
<211> LENGTH: 238
<212> TYPE: PRT
<213> ORGANISM: Mus musculus

<400> SEQUENCE: 46

Met Ser Pro Val Gln Phe Leu Phe Leu Leu Met Leu Trp Ile Gln Glu
1               5                   10                  15

Thr Asn Gly Asp Val Val Met Thr Gln Thr Pro Leu Ser Leu Ser Val
            20                  25                  30

Thr Ile Gly Gln Pro Ala Ser Ile Ser Cys Lys Ser Ser Gln Ser Leu
        35                  40                  45

Leu Tyr Ser Asn Gly Lys Thr Tyr Leu Asn Trp Leu Gln Gln Arg Pro
    50                  55                  60

Gly Gln Ala Pro Lys His Leu Met Tyr Gln Val Ser Lys Leu Asp Pro
65                  70                  75                  80

Gly Ile Pro Asp Arg Phe Ser Gly Ser Gly Ser Glu Thr Asp Phe Thr
                85                  90                  95

Leu Lys Ile Ser Arg Val Glu Ala Glu Asp Leu Gly Val Tyr Tyr Cys
            100                 105                 110

Leu Gln Ser Thr Tyr Tyr Pro Leu Thr Phe Gly Ala Gly Thr Lys Leu
        115                 120                 125

Glu Leu Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 47
<211> LENGTH: 108
<212> TYPE: PRT
<213> ORGANISM: Mus musculus

<400> SEQUENCE: 47

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Asn Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
50                  55                  60

Ser Gly Ser Gly Gln Asp Tyr Ser Leu Thr Ile Ser Ser Leu Glu Tyr
65                  70                  75                  80

Glu Asp Met Gly Ile Asn Tyr Cys Leu Gln Cys Asp Glu Phe Pro Pro
                85                  90                  95

Trp Thr Phe Gly Gly Gly Thr Lys Leu Glu Ile Lys
            100                 105

<210> SEQ ID NO 48
<211> LENGTH: 112
<212> TYPE: PRT
<213> ORGANISM: Mus musculus

<400> SEQUENCE: 48

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 49
<211> LENGTH: 234
<212> TYPE: PRT
<213> ORGANISM: Mus musculus

<400> SEQUENCE: 49

Met Arg Pro Ser Ile Gln Phe Leu Gly Leu Leu Leu Phe Trp Leu His
1               5                   10                  15

Gly Val Gln Cys Asp Ile Gln Met Thr Gln Ser Pro Ser Ser Leu Ser
            20                  25                  30

Ala Ser Leu Gly Gly Lys Val Thr Ile Thr Cys Lys Ala Ser Gln Asp
        35                  40                  45

Ile Asn Lys Asn Ile Val Trp Tyr Gln His Lys Pro Gly Lys Gly Pro
50                  55                  60

Arg Leu Leu Ile Trp Tyr Thr Ser Thr Leu Gln Pro Gly Ile Pro Ser
65                  70                  75                  80

Arg Phe Ser Gly Ser Gly Ser Gly Arg Asp Tyr Ser Phe Ser Ile Ser
                85                  90                  95

Asn Leu Glu Pro Glu Asp Ile Ala Thr Tyr Tyr Cys Leu Gln Tyr Asp
            100                 105                 110

Asn Leu Pro Arg Thr Phe Gly Gly Gly Thr Lys Leu Glu Ile Lys Arg

```
            115                 120                 125
Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 50
<211> LENGTH: 107
<212> TYPE: PRT
<213> ORGANISM: Mus musculus

<400> SEQUENCE: 50

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Asn
            20                  25                  30

Ile Ile Trp Tyr Gln His Lys Pro Gly Lys Gly Pro Arg Leu Leu Ile
        35                  40                  45

Trp Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Pro Arg
                85                  90                  95

Thr Phe Gly Gly Gly Thr Lys Leu Glu Ile Lys
            100                 105

<210> SEQ ID NO 51
<211> LENGTH: 239
<212> TYPE: PRT
<213> ORGANISM: Mus musculus

<400> SEQUENCE: 51

Met Arg Phe Ser Ala Gln Leu Leu Gly Leu Leu Val Leu Trp Ile Pro
1               5                   10                  15

Gly Ser Thr Ala Asp Ile Val Met Thr Gln Ala Ala Phe Ser Asn Pro
            20                  25                  30

Val Thr Leu Gly Thr Ser Thr Ser Ile Ser Cys Arg Ser Ser Lys Ser
        35                  40                  45

Leu Leu His Ser Asn Gly Ile Thr Tyr Leu Tyr Trp Tyr Leu Gln Lys
    50                  55                  60

Pro Gly Gln Ser Pro Gln Leu Leu Ile Tyr Gln Met Ser Asn Leu Ala
65                  70                  75                  80

Ser Gly Val Pro Asp Arg Phe Ser Ser Ser Gly Ser Gly Thr Asp Phe
                85                  90                  95

Thr Leu Arg Ile Ser Arg Val Glu Ala Glu Asp Val Gly Val Tyr Tyr
            100                 105                 110
```

Cys Ala Gln Asn Leu Glu Leu Pro Tyr Thr Phe Gly Ser Gly Thr Lys
            115                 120                 125

Leu Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
            165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
            195                 200                 205

Ala Asp Tyr Glu Lys His Lys Val Tyr Ala Cys Glu Val Thr His Gln
            210                 215                 220

Gly Leu Ser Ser Pro Val Thr Lys Ser Phe Asn Arg Gly Glu Cys
225                 230                 235

<210> SEQ ID NO 52
<211> LENGTH: 112
<212> TYPE: PRT
<213> ORGANISM: Mus musculus

<400> SEQUENCE: 52

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Phe Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Ser Gly Thr Lys Leu Glu Ile Lys
            100                 105                 110

<210> SEQ ID NO 53
<211> LENGTH: 107
<212> TYPE: PRT
<213> ORGANISM: Mus musculus

<400> SEQUENCE: 53

Asp Ile Val Leu Thr Gln Ser Pro Ala Thr Leu Ser Val Thr Pro Gly
1               5                   10                  15

Asp Arg Val Ser Leu Ser Cys Arg Ala Ser His Ser Ile Ser Asn Phe
            20                  25                  30

Leu His Trp Tyr Pro Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Asn Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ile Trp Ser Leu
                85                  90                  95

Thr Phe Gly Ala Gly Thr Lys Leu Glu Leu Lys
            100                 105

<210> SEQ ID NO 54
<211> LENGTH: 111
<212> TYPE: PRT
<213> ORGANISM: Mus musculus

<400> SEQUENCE: 54

Asp Ile Val Leu Thr Gln Ser Pro Thr Ser Leu Ala Val Ser Leu Gly
1               5                   10                  15

Gln Ser Val Thr Ile Ser Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Gly Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Arg
                85                  90                  95

Lys Val Pro Tyr Thr Phe Gly Ser Gly Thr Lys Leu Glu Ile Lys
            100                 105                 110

<210> SEQ ID NO 55
<211> LENGTH: 333
<212> TYPE: DNA
<213> ORGANISM: Mus musculus

<400> SEQUENCE: 55
cagatccagt tggagcagtc tggacctgag ctgaagaagc tggagagaca agtcaagatc      60
tcctgcaagg cttctggtta tatttttcaga gactattcaa tgcactgggt gaagcaggct    120
ccaggaaagg gtttaaagtg gatgggctgg ataaacactg agacgggtga gccaacatat    180
gcagatgact tcaagggacg gtttgccttc tctttggaaa cctctgccag cactgcctat    240
ttgcagatca caaacctcaa aaatgaggac acggctacat atttctgtac tagcctttac    300
tggggccaag ggactctggt cactgtctct gca                                  333

<210> SEQ ID NO 56
<211> LENGTH: 372
<212> TYPE: DNA
<213> ORGANISM: Mus musculus

<400> SEQUENCE: 56
caggtcactc tgaaagagtc tggccctggg atattgcagc cctcccagac cctcagtctg      60
acttgttctt tctctgggtt ttcactgagc acttatggta tgggtgtagg ttggattcgt    120
cagccttcag ggaagggtct ggagtggctg gccaacattt ggtggcatga tgataagtac    180
tataactcag ccctgaagag ccggctcaca atctccaagg atatctccaa caaccaggta    240
ttcctcaaga tctccagtgt ggacactgca gatactgcca catactactg tgctcaaata    300 gccccctcgat ataataagta cgaaggcttt tttgctttct ggggccaagg gactctggtc    360
actgtctctg ca                                                         372

<210> SEQ ID NO 57
<211> LENGTH: 345
<212> TYPE: DNA
<213> ORGANISM: Mus musculus

```
<400> SEQUENCE: 57
caggttcaac tgcagcagtc tggggctgag ctggtgaggc ctggggcttc agtgaagctg      60
tcctgcaagg cttcgggcta cacatttact gactatgaaa tgcactgggt gaagcagaca     120
cctgtgcatg gcctaaaatg gattggagct cttgatccta aaactggtga tactgcctac     180
agtcagaagt tcaagggcaa ggccacactg actgcagaca atcctccag cacagcctac      240 atggagctcc gcagcctgac atctgaggac tctgccgtct attactgtac aagattctac     300
tcctatactt actggggcca aggactctg gtcactgtct ctgca                      345

<210> SEQ ID NO 58
<211> LENGTH: 357
<212> TYPE: DNA
<213> ORGANISM: Mus musculus

<400> SEQUENCE: 58
gaggtgcagc ttgttgagac tggtggagga ctggtgcagc ctgaagggtc attgaaactc      60
tcatgtgcag cttctggatt cagcttcaat atcaatgcca tgaactgggt ccgccaggct     120
ccaggaaagg gtttgaatg ggttgctcgc ataagaagtg aaagtaataa ttatgcaaca      180
tattatggcg attcagtgaa agacaggttc accatctcca gagatgattc acaaaacatg     240
ctctatctac aaatgaacaa cttgaaaact gaggacacag ccatatatta ctgtgtgaga     300
gaggtaacta catcgtttgc ttattgggc aagggactc tggtcactgt ctctgca          357

<210> SEQ ID NO 59
<211> LENGTH: 369
<212> TYPE: DNA
<213> ORGANISM: Mus musculus

<400> SEQUENCE: 59
gaggtgcagc ttgttgagac tggtggagga ttggtgcagc ctaaagggtc attgaaactc      60
tcatgtgcag cctctggatt caccttcaat gccagtgcca tgaactgggt ccgccaggct     120
ccaggaaagg gtttgaatg ggttgctcgc ataagaagta aaagtaataa ttatgcaata      180
tattatgccg attcagtgaa agacaggttc accatctcca gagatgattc acaaagcatg     240
ctctatctgc aaatgaacaa cttgaaaact gaggacacag ccatgtatta ctgtgtgaga     300
gatccgggct actatggtaa ccccctggttt gcttactggg ccaagggac tctggtcact    360 gtctctgca                                                             369

<210> SEQ ID NO 60
<211> LENGTH: 111
<212> TYPE: PRT
<213> ORGANISM: Mus musculus

<400> SEQUENCE: 60
```

Gln Ile Gln Leu Glu Gln Ser Gly Pro Glu Leu Lys Lys Pro Gly Glu
1               5                   10                  15

Thr Val Lys Ile Ser Cys Lys Ala Ser Gly Tyr Ile Phe Arg Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys

```
                         85                  90                  95

Thr Ser Leu Tyr Trp Gly Gln Gly Thr Leu Val Thr Val Ser Ala
            100                 105                 110

<210> SEQ ID NO 61
<211> LENGTH: 124
<212> TYPE: PRT
<213> ORGANISM: Mus musculus

<400> SEQUENCE: 61

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Gly Trp Ile Arg Gln Pro Ser Gly Lys Gly Leu Glu
        35                  40                  45

Trp Leu Ala Asn Ile Trp Trp His Asp Asp Lys Tyr Tyr Asn Ser Ala
    50                  55                  60

Leu Lys Ser Arg Leu Thr Ile Ser Lys Asp Ile Ser Asn Asn Gln Val
65                  70                  75                  80

Phe Leu Lys Ile Ser Ser Val Asp Thr Ala Asp Thr Ala Thr Tyr Tyr
                85                  90                  95

Cys Ala Gln Ile Ala Pro Arg Tyr Asn Lys Tyr Glu Gly Phe Phe Ala
            100                 105                 110

Phe Trp Gly Gln Gly Thr Leu Val Thr Val Ser Ala
        115                 120

<210> SEQ ID NO 62
<211> LENGTH: 115
<212> TYPE: PRT
<213> ORGANISM: Mus musculus

<400> SEQUENCE: 62

Gln Val Gln Leu Gln Gln Ser Gly Ala Glu Leu Val Arg Pro Gly Ala
1               5                   10                  15

Ser Val Lys Leu Ser Cys Lys Ala Ser Gly Tyr Thr Phe Thr Asp Tyr
            20                  25                  30

Glu Met His Trp Val Lys Gln Thr Pro Val His Gly Leu Lys Trp Ile
        35                  40                  45

Gly Ala Leu Asp Pro Lys Thr Gly Asp Thr Ala Tyr Ser Gln Lys Phe
    50                  55                  60

Lys Gly Lys Ala Thr Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ala
        115

<210> SEQ ID NO 63
<211> LENGTH: 119
<212> TYPE: PRT
<213> ORGANISM: Mus musculus

<400> SEQUENCE: 63

Glu Val Gln Leu Val Glu Thr Gly Gly Gly Leu Val Gln Pro Glu Gly
1               5                   10                  15
```

Ser Leu Lys Leu Ser Cys Ala Ala Ser Gly Phe Ser Phe Asn Ile Asn
            20                  25                  30

Ala Met Asn Trp Val Arg Gln Ala Pro Gly Lys Gly Leu Glu Trp Val
        35                  40                  45

Ala Arg Ile Arg Ser Glu Ser Asn Asn Tyr Ala Thr Tyr Tyr Gly Asp
    50                  55                  60

Ser Val Lys Asp Arg Phe Thr Ile Ser Arg Asp Asp Ser Gln Asn Met
65                  70                  75                  80

Leu Tyr Leu Gln Met Asn Asn Leu Lys Thr Glu Asp Thr Ala Ile Tyr
                85                  90                  95

Tyr Cys Val Arg Glu Val Thr Thr Ser Phe Ala Tyr Trp Gly Gln Gly
            100                 105                 110

Thr Leu Val Thr Val Ser Ala
        115

<210> SEQ ID NO 64
<211> LENGTH: 123
<212> TYPE: PRT
<213> ORGANISM: Mus musculus

<400> SEQUENCE: 64

Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Asn Ala Ser
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Ile Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Asp Pro Gly Tyr Tyr Gly Asn Pro Trp Phe Ala Tyr
            100                 105                 110

Trp Gly Gln Gly Thr Leu Val Thr Val Ser Ala
        115                 120

<210> SEQ ID NO 65
<211> LENGTH: 336
<212> TYPE: DNA
<213> ORGANISM: Mus musculus

<400> SEQUENCE: 65
gatgttgtga tgacccagac tccactcact tgtcggttac cccttggaca accagcctcc      60
atctcttgca agtcaagtca gagcctctta catagtgatg aaagacatt tttgaattgg      120 ttattacaga ggccaggcca gtctccaaag cgcctaatct atctggtgtc tagactggac      180
tctggagtcc ctgacaggtt cactggcagt ggatcaggga cagatttcac actgaaaatc      240
agcagagtgg aggctgagga tttgggagtt tattattgct gccaaggtac acattttcct      300
cggacgttcg gtggaggcac caggctggaa atcaaa                                336

<210> SEQ ID NO 66
<211> LENGTH: 336
<212> TYPE: DNA
<213> ORGANISM: Mus musculus

<400> SEQUENCE: 66

```
gatgttttga tgacccaaac tccactctcc ctgcctgtca gtcttggaga tcaagcctcc      60
atctcttgca gatctagtca gagcattgta catagtaatg gaaacaccta tttagaatgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttccg     300
tggacgttcg gtggaggcac caagctggaa atcaaa                               336
```

<210> SEQ ID NO 67
<211> LENGTH: 336
<212> TYPE: DNA
<213> ORGANISM: Mus musculus

<400> SEQUENCE: 67

```
gatgttgtga tgacccaaac tccactctcc ctgcctgtca gtcttggaga tcaagcctcc      60
atctcttgca gatctagtca gagccttgta cacagtaatg gaaacaccta tttacattgg     120
tacctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaaatac acatgttcct     300
cctacgttcg gatcggggac caagctggaa ataaaa                               336
```

<210> SEQ ID NO 68
<211> LENGTH: 336
<212> TYPE: DNA
<213> ORGANISM: Mus musculus

<400> SEQUENCE: 68

```
gatattgtga tgactcagtc tgcaccctct gtacctgtca ctcctggaga gtcagtatcc      60
atctcctgca agtctagtaa gagtctcctg catagtaatg gcaacactta cttgaattgg     120
ttcctgcaga ggccaggcca gtctcctcaa ctcctgattt attggatgtc caaccttgcc     180
tcaggagtcc cagacaggtt cagtggcagt gggtcaggaa ctgctttcac actgagaatc     240
agtagagtgg aggctgagga tgtgggtgtt tattactgta tgcaacatat agaatacccct    300 ttcacgttcg gcacggggac aaaattggaa ataaaa                               336
```

<210> SEQ ID NO 69
<211> LENGTH: 336
<212> TYPE: DNA
<213> ORGANISM: Mus musculus

<400> SEQUENCE: 69

```
gatattgtga tgacgcaggc tgcattctcc aatccagtca ctcttggaac atcagcttcc      60
atctcctgca ggtctagtaa gagtctccta catagttatg acatcactta tttgtattgg     120
tatctgcaga agccaggcca gtctcctcag ctcctgattt atcagatgtc caaccttgcc     180
tcaggagtcc cagacaggtt cagtagcagt gggtcaggaa ctgatttcac actgagaatc     240
agcagagtgg aggctgagga tgtgggtgtt tattactgtg ctcaaaatct agaacttcct     300
ccgacgttcg gtggaggcac caagctggaa atcaaa                               336
```

<210> SEQ ID NO 70
<211> LENGTH: 318
<212> TYPE: DNA
<213> ORGANISM: Mus musculus

<400> SEQUENCE: 70

```
caaattgttc tcacccagtc tccagcaatc atgtctgcat ttccagggga gaaggtcacc      60
atgacctgca gtgccagctc aagtgttagt tacatgtact ggtaccagca gaagtcagga     120
tcctccccca gactcctgat ttatgacaca tccaacctgg cttctggagt ccctgttcgc     180
ttcagtggca gtgggtctgg gacctcttac tctctcacaa tcagccgaat ggaggctgaa     240
gatgctgcca cttattactg ccagcagtgg agtagttacc cgctcacgtt cggtggtggg     300
accgagctgg agctgaaa                                                   318
```

<210> SEQ ID NO 71
<211> LENGTH: 112
<212> TYPE: PRT
<213> ORGANISM: Mus musculus

<400> SEQUENCE: 71

Asp Val Val Met Thr Gln Thr Pro Leu Thr Leu Ser Val Thr Leu Gly
1               5                   10                  15

Gln Pro Ala Ser Ile Ser Cys Lys Ser Ser Gln Ser Leu Leu His Ser
            20                  25                  30

Asp Gly Lys Thr Phe Leu Asn Trp Leu Leu Gln Arg Pro Gly Gln Ser
        35                  40                  45

Pro Lys Arg Leu Ile Tyr Leu Val Ser Arg Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Cys Gln Gly
                85                  90                  95

Thr His Phe Pro Arg Thr Phe Gly Gly Gly Thr Arg Leu Glu Ile Lys
            100                 105                 110

<210> SEQ ID NO 72
<211> LENGTH: 112
<212> TYPE: PRT
<213> ORGANISM: Mus musculus

<400> SEQUENCE: 72

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 73
<211> LENGTH: 112
<212> TYPE: PRT
<213> ORGANISM: Mus musculus

<400> SEQUENCE: 73

Asp Val Val Met Thr Gln Thr Pro Leu Ser Leu Pro Val Ser Leu Gly

```
                1               5                   10                  15
Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr His Val Pro Pro Thr Phe Gly Ser Gly Thr Lys Leu Glu Ile Lys
            100                 105                 110

<210> SEQ ID NO 74
<211> LENGTH: 112
<212> TYPE: PRT
<213> ORGANISM: Mus musculus

<400> SEQUENCE: 74

Asp Ile Val Met Thr Gln Ser Ala Pro Ser Val Pro Val Thr Pro Gly
1               5                   10                  15

Glu Ser Val Ser Ile Ser Cys Lys Ser Ser Lys Ser Leu Leu His Ser
                20                  25                  30

Asn Gly Asn Thr Tyr Leu Asn Trp Phe Leu Gln Arg Pro Gly Gln Ser
            35                  40                  45

Pro Gln Leu Leu Ile Tyr Trp Met Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Ile Glu Tyr Pro Phe Thr Phe Gly Thr Gly Thr Lys Leu Glu Ile Lys
            100                 105                 110

<210> SEQ ID NO 75
<211> LENGTH: 112
<212> TYPE: PRT
<213> ORGANISM: Mus musculus

<400> SEQUENCE: 75

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
                20                  25                  30

Tyr Asp Ile Thr Tyr Leu Tyr Trp Tyr Leu Gln Lys Pro Gly Gln Ser
            35                  40                  45

Pro Gln Leu Leu Ile Tyr Gln Met Ser Asn Leu Ala Ser Gly Val Pro
        50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Pro Thr Phe Gly Gly Gly Thr Lys Leu Glu Ile Lys
            100                 105                 110

<210> SEQ ID NO 76
```

<211> LENGTH: 106
<212> TYPE: PRT
<213> ORGANISM: Mus musculus

<400> SEQUENCE: 76

```
Gln Ile Val Leu Thr Gln Ser Pro Ala Ile Met Ser Ala Phe Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Ser Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Leu Thr
                85                  90                  95

Phe Gly Gly Gly Thr Glu Leu Glu Leu Lys
            100                 105
```

<210> SEQ ID NO 77
<211> LENGTH: 345
<212> TYPE: DNA
<213> ORGANISM: Artificial Sequence
<220> FEATURE:
<223> OTHER INFORMATION: Mouse-human chimeric antibody H chain

<400> SEQUENCE: 77

| | |
|---|---|
| caggtgcagc tggtggagtc tggagctgag gtgaagaagc ctggggcctc agtgaaggtc | 60 |
| tcctgcaagg cttctggata caccttcacc gactatgaaa tgcactgggt gcgacaggcc | 120 |
| cctggacaag ggcttgagtg gatgggagct cttgatccta aaactggtga tactgcctac | 180 |
| agtcagaagt tcaagggcag agtcacgatt accgcggacg aatccacgag cacagcctac | 240 |
| atggagctga gcagcctgag atctgaggac acggccgtgt attactgtgc gagattctac | 300 |
| tcctatactt actggggcca gggaaccctg gtcaccgtct cctca | 345 |

<210> SEQ ID NO 78
<211> LENGTH: 345
<212> TYPE: DNA
<213> ORGANISM: Artificial Sequence
<220> FEATURE:
<223> OTHER INFORMATION: Mouse-human chimeric antibody H chain

<400> SEQUENCE: 78

| | |
|---|---|
| caggtgcagc tggtggagtc tggagctgag gtgaagaagc ctggggcctc agtgaaggtc | 60 |
| tcctgcaagg cttctggata caccttcacc gactatgaaa tgcactgggt gcgacaggcc | 120 |
| cctggacaag ggcttgagtg gatgggagct cttgatccta aaactggtga tactgcctac | 180 |
| agtcagaagt tcaagggcag agtcacgctg accgcggacg aatccacgag cacagcctac | 240 |
| atggagctga gcagcctgag atctgaggac acggccgtgt attactgtac aagattctac | 300 |
| tcctatactt actggggcca gggaaccctg gtcaccgtct cctca | 345 |

<210> SEQ ID NO 79
<211> LENGTH: 345
<212> TYPE: DNA
<213> ORGANISM: Artificial Sequence
<220> FEATURE:
<223> OTHER INFORMATION: Mouse-human chimeric antibody H chain

<400> SEQUENCE: 79

```
caggtgcagc tggtggagtc tggagctgag gtgaagaagc ctggggcctc agtgaaggtc    60
tcctgcaagg cttctggata caccttcacc gactatgaaa tgcactgggt gcgacaggcc   120
cctggacaag ggcttgagtg gatgggagct cttgatccta aaactggtga tactgcctac   180
agtcagaagt tcaagggcag agtcacgctg accgcggaca atccacgag cacagcctac    240 atggagctga gcagcctgag atctgaggac acggccgtgt attactgtac aagattctac   300
tcctatactt actggggcca gggaaccctg gtcaccgtct cctca                   345
```

<210> SEQ ID NO 80
<211> LENGTH: 345
<212> TYPE: DNA
<213> ORGANISM: Artificial Sequence
<220> FEATURE:
<223> OTHER INFORMATION: Mouse-human chimeric antibody H chain

<400> SEQUENCE: 80

```
caggtgcagc tggtggagtc tggagctgag gtgaagaagc ctggggcctc agtgaaggtc    60
tcctgcaagg cttctggata caccttcacc gactatgaaa tgcactgggt gcgacaggcc   120
cctggacaag ggcttgagtg gatgggagct cttgatccta aaactggtga tactgcctac   180
agtcagaagt tcaagggcag agtcacgctg accgcggaca atccacgag cacagcctac    240 atggagctga gcagcctgac atctgaggac acggccgtgt attactgtac aagattctac   300
tcctatactt actggggcca gggaaccctg gtcaccgtct cctca                   345
```

<210> SEQ ID NO 81
<211> LENGTH: 345
<212> TYPE: DNA
<213> ORGANISM: Artificial Sequence
<220> FEATURE:
<223> OTHER INFORMATION: Mouse-human chimeric antibody H chain

<400> SEQUENCE: 81

```
caggtgcagc tggtgcagtc tggagctgag gtgaagaagc ctggggcctc agtgaaggtc    60
tcctgcaagg cttctggata caccttcacc gactatgaaa tgcactgggt gcgacaggcc   120
cctggacaag ggcttgagtg gatgggagct cttgatccta aaactggtga tactgcctac   180
agtcagaagt tcaagggcag agtcacgctg accgcggacg aatccacgag cacagcctac   240
atggagctga gcagcctgag atctgaggac acggccgtgt attactgtac aagattctac   300
tcctatactt actggggcca gggaaccctg gtcaccgtct cctca                   345
```

<210> SEQ ID NO 82
<211> LENGTH: 345
<212> TYPE: DNA
<213> ORGANISM: Artificial Sequence
<220> FEATURE:
<223> OTHER INFORMATION: Mouse-human chimeric antibody H chain

<400> SEQUENCE: 82

```
caggtgcagc tggtgcagtc tggagctgag gtgaagaagc ctggggcctc agtgaaggtc    60
tcctgcaagg cttctggata caccttcacc gactatgaaa tgcactgggt gcgacaggcc   120
cctggacaag ggcttgagtg gatgggagct cttgatccta aaactggtga tactgcctac   180
agtcagaagt tcaagggcag agtcacgctg accgcggaca atccacgag cacagcctac    240 atggagctga gcagcctgag atctgaggac acggccgtgt attactgtac aagattctac   300
tcctatactt actggggcca gggaaccctg gtcaccgtct cctca                   345
```

<210> SEQ ID NO 83
<211> LENGTH: 345
<212> TYPE: DNA
<213> ORGANISM: Artificial Sequence
<220> FEATURE:
<223> OTHER INFORMATION: Mouse-human chimeric antibody H chain

<400> SEQUENCE: 83

```
caggtgcagc tggtgcagtc tggagctgag gtgaagaagc ctggggcctc agtgaaggtc      60
tcctgcaagg cttctggata caccttcacc gactatgaaa tgcactgggt gcgacaggcc     120
cctggacaag ggcttgagtg gatgggagct cttgatccta aaactggtga tactgcctac     180
agtcagaagt tcaagggcag agtcacgctg accgcgaca aatccacgag cacagcctac     240
atggagctga gcagcctgac atctgaggac acggccgtgt attactgtac aagattctac     300
tcctatactt actggggcca gggaaccctg gtcaccgtct cctca                    345
```

<210> SEQ ID NO 84
<211> LENGTH: 115
<212> TYPE: PRT
<213> ORGANISM: Artificial Sequence
<220> FEATURE:
<223> OTHER INFORMATION: Mouse-human chimeric antibody H chain

<400> SEQUENCE: 84

```
Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Tyr Ser Tyr Thr Tyr Trp Gly Gln Gly Thr Leu Val Thr
            100                 105                 110

Val Ser Ser
        115
```

<210> SEQ ID NO 85
<211> LENGTH: 115
<212> TYPE: PRT
<213> ORGANISM: Artificial Sequence
<220> FEATURE:
<223> OTHER INFORMATION: Mouse-human chimeric antibody H chain

<400> SEQUENCE: 85

```
Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
            85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 86
<211> LENGTH: 115
<212> TYPE: PRT
<213> ORGANISM: Artificial Sequence
<220> FEATURE:
<223> OTHER INFORMATION: Mouse-human chimeric antibody H chain

<400> SEQUENCE: 86

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 87
<211> LENGTH: 115
<212> TYPE: PRT
<213> ORGANISM: Artificial Sequence
<220> FEATURE:
<223> OTHER INFORMATION: Mouse-human chimeric antibody H chain

<400> SEQUENCE: 87

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
            85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 88
<211> LENGTH: 115
```

```
<212> TYPE: PRT
<213> ORGANISM: Artificial Sequence
<220> FEATURE:
<223> OTHER INFORMATION: Mouse-human chimeric antibody H chain

<400> SEQUENCE: 88

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 89
<211> LENGTH: 115
<212> TYPE: PRT
<213> ORGANISM: Artificial Sequence
<220> FEATURE:
<223> OTHER INFORMATION: Mouse-human chimeric antibody H chain

<400> SEQUENCE: 89

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 90
<211> LENGTH: 115
<212> TYPE: PRT
<213> ORGANISM: Artificial Sequence
<220> FEATURE:
<223> OTHER INFORMATION: Mouse-human chimeric antibody H chain

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30
```

```
Glu Met His Trp Val Arg Gln Ala Pro Gly Gln Gly Leu Glu Trp Met
         35                  40                  45

Gly Ala Leu Asp Pro Lys Thr Gly Asp Thr Ala Tyr Ser Gln Lys Phe
 50                  55                  60

Lys Gly Arg Val Thr Leu Thr Ala Asp Lys Ser Thr Ser Thr Ala Tyr
 65                  70                  75                  80

Met Glu Leu Ser Ser Leu Thr Ser Glu Asp Thr Ala Val Tyr Tyr Cys
                 85                  90                  95

Thr Arg Phe Tyr Ser Tyr Thr Tyr Trp Gly Gln Gly Thr Leu Val Thr
                100                 105                 110

Val Ser Ser
        115

<210> SEQ ID NO 91
<211> LENGTH: 336
<212> TYPE: DNA
<213> ORGANISM: Artificial Sequence
<220> FEATURE:
<223> OTHER INFORMATION: Mouse-human chimeric antibody L chain

<400> SEQUENCE: 91
gatgttgtga tgactcagtc tccactctcc ctgcccgtca cccctggaga gccggcctcc      60
atctcctgca gatctagtca gagccttgta cacagtaatg aaacaccta tttacattgg     120 tacctgcaga agccagggca gtctccacag ctcctgatct ataaagtttc caaccgattt     180
tctggggtcc ctgacaggtt cagtggcagt ggatcaggca cagattttac actgaaaatc     240
agcagagtgg aggctgagga tgttggggtt tattactgct ctcaaaatac acatgttcct     300
cctacgtttg gccaggggac caagctggag atcaaa                               336

<210> SEQ ID NO 92
<211> LENGTH: 112
<212> TYPE: PRT
<213> ORGANISM: Artificial Sequence
<220> FEATURE:
<223> OTHER INFORMATION: Mouse-human chimeric antibody L chain

<400> SEQUENCE: 92

Asp Val Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Val His Ser
                 20                  25                  30

Asn Gly Asn Thr Tyr Leu His Trp Tyr Leu Gln Lys Pro Gly Gln Ser
         35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                 85                  90                  95

Thr His Val Pro Pro Thr Phe Gly Gln Gly Thr Lys Leu Glu Ile Lys
                100                 105                 110

<210> SEQ ID NO 93
<211> LENGTH: 14
<212> TYPE: PRT
<213> ORGANISM: Homo sapiens

<400> SEQUENCE: 93
```

```
Gly Asn Ser Gln Gln Ala Thr Pro Lys Asp Asn Glu Ile Ser
1               5                   10
```

<210> SEQ ID NO 94
<211> LENGTH: 8
<212> TYPE: PRT
<213> ORGANISM: Homo sapiens

<400> SEQUENCE: 94

```
Gly Asn Ser Gln Gln Ala Thr Pro
1               5
```

<210> SEQ ID NO 95
<211> LENGTH: 8
<212> TYPE: PRT
<213> ORGANISM: Homo sapiens

<400> SEQUENCE: 95

```
Gln Gln Ala Thr Pro Lys Asp Asn
1               5
```

<210> SEQ ID NO 96
<211> LENGTH: 8
<212> TYPE: PRT
<213> ORGANISM: Homo sapiens

<400> SEQUENCE: 96

```
Thr Pro Lys Asp Asn Glu Ile Ser
1               5
```

<210> SEQ ID NO 97
<211> LENGTH: 10
<212> TYPE: PRT
<213> ORGANISM: Homo sapiens

<400> SEQUENCE: 97

```
Ala Thr Pro Lys Asp Asn Glu Ile Ser Thr
1               5                   10
```

<210> SEQ ID NO 98
<211> LENGTH: 10
<212> TYPE: PRT
<213> ORGANISM: Homo sapiens

<400> SEQUENCE: 98

```
Pro Lys Asp Asn Glu Ile Ser Thr Phe His
1               5                   10
```

<210> SEQ ID NO 99
<211> LENGTH: 10
<212> TYPE: PRT
<213> ORGANISM: Homo sapiens

<400> SEQUENCE: 99

```
Asp Asn Glu Ile Ser Thr Phe His Asn Leu
1               5                   10
```

<210> SEQ ID NO 100
<211> LENGTH: 10
<212> TYPE: PRT
<213> ORGANISM: Homo sapiens

<400> SEQUENCE: 100

```
Glu Ile Ser Thr Phe His Asn Leu Gly Asn
1               5                   10
```

<210> SEQ ID NO 101
<211> LENGTH: 27
<212> TYPE: PRT
<213> ORGANISM: Homo sapiens

<400> SEQUENCE: 101

Gly Asn Ser Gln Gln Ala Thr Pro Lys Asp Asn Glu Ile Ser Thr Phe
1               5                   10                  15

His Asn Leu Gly Asn Val His Ser Pro Leu Lys
            20                  25

<210> SEQ ID NO 102
<211> LENGTH: 14
<212> TYPE: PRT
<213> ORGANISM: Homo sapiens

<400> SEQUENCE: 102

Ser Thr Phe His Asn Leu Gly Asn Val His Ser Pro Leu Lys
1               5                   10

<210> SEQ ID NO 103
<211> LENGTH: 5
<212> TYPE: PRT
<213> ORGANISM: Mus musculus

<400> SEQUENCE: 103

Asn Tyr Ala Met Ser
1               5

<210> SEQ ID NO 104
<211> LENGTH: 17
<212> TYPE: PRT
<213> ORGANISM: Mus musculus

<400> SEQUENCE: 104

Ala Ile Asn Asn Asn Gly Asp Asp Thr Tyr Tyr Leu Asp Thr Val Lys
1               5                   10                  15

Asp

<210> SEQ ID NO 105
<211> LENGTH: 5
<212> TYPE: PRT
<213> ORGANISM: Mus musculus

<400> SEQUENCE: 105

Gln Gly Gly Ala Tyr
1               5

<210> SEQ ID NO 106
<211> LENGTH: 7
<212> TYPE: PRT
<213> ORGANISM: Mus musculus

<400> SEQUENCE: 106

Thr Tyr Gly Met Gly Val Gly
1               5

<210> SEQ ID NO 107
<211> LENGTH: 16
<212> TYPE: PRT
<213> ORGANISM: Mus musculus

<400> SEQUENCE: 107

Asn Ile Trp Trp Tyr Asp Ala Lys Tyr Tyr Asn Ser Asp Leu Lys Ser

<210> SEQ ID NO 108
<211> LENGTH: 8
<212> TYPE: PRT
<213> ORGANISM: Mus musculus

<400> SEQUENCE: 108

Met Gly Leu Ala Trp Phe Ala Tyr
1               5

<210> SEQ ID NO 109
<211> LENGTH: 7
<212> TYPE: PRT
<213> ORGANISM: Mus musculus

<400> SEQUENCE: 109

Ile Tyr Gly Met Gly Val Gly
1               5

<210> SEQ ID NO 110
<211> LENGTH: 16
<212> TYPE: PRT
<213> ORGANISM: Mus musculus

<400> SEQUENCE: 110

Asn Ile Trp Trp Asn Asp Asp Lys Tyr Tyr Asn Ser Ala Leu Lys Ser
1               5                   10                  15

<210> SEQ ID NO 111
<211> LENGTH: 8
<212> TYPE: PRT
<213> ORGANISM: Mus musculus

<400> SEQUENCE: 111

Ile Gly Tyr Phe Tyr Phe Asp Tyr
1               5

<210> SEQ ID NO 112
<211> LENGTH: 5
<212> TYPE: PRT
<213> ORGANISM: Mus musculus

<400> SEQUENCE: 112

Gly Tyr Trp Met His
1               5

<210> SEQ ID NO 113
<211> LENGTH: 17
<212> TYPE: PRT
<213> ORGANISM: Mus musculus

<400> SEQUENCE: 113

Ala Ile Tyr Pro Gly Asn Ser Asp Thr Asn Tyr Asn Gln Lys Phe Lys
1               5                   10                  15

Gly

<210> SEQ ID NO 114
<211> LENGTH: 10
<212> TYPE: PRT
<213> ORGANISM: Mus musculus

<400> SEQUENCE: 114

Ser Gly Asp Leu Thr Gly Gly Leu Ala Tyr
1               5                   10

<210> SEQ ID NO 115
<211> LENGTH: 5
<212> TYPE: PRT
<213> ORGANISM: Mus musculus

<400> SEQUENCE: 115

Ser Tyr Ala Met Ser
1               5

<210> SEQ ID NO 116
<211> LENGTH: 17
<212> TYPE: PRT
<213> ORGANISM: Mus musculus

<400> SEQUENCE: 116

Ala Ile Asn Ser Asn Gly Gly Thr Thr Tyr Tyr Pro Asp Thr Met Lys
1               5                   10                  15

Asp

<210> SEQ ID NO 117
<211> LENGTH: 13
<212> TYPE: PRT
<213> ORGANISM: Mus musculus

<400> SEQUENCE: 117

His Asn Gly Gly Tyr Glu Asn Tyr Gly Trp Phe Ala Tyr
1               5                   10

<210> SEQ ID NO 118
<211> LENGTH: 5
<212> TYPE: PRT
<213> ORGANISM: Mus musculus

<400> SEQUENCE: 118

Ser Tyr Trp Met His
1               5

<210> SEQ ID NO 119
<211> LENGTH: 17
<212> TYPE: PRT
<213> ORGANISM: Mus musculus

<400> SEQUENCE: 119

Glu Ile Asp Pro Ser Asp Ser Tyr Thr Tyr Tyr Asn Gln Lys Phe Arg
1               5                   10                  15

Gly

<210> SEQ ID NO 120
<211> LENGTH: 15
<212> TYPE: PRT
<213> ORGANISM: Mus musculus

<400> SEQUENCE: 120

Ser Asn Leu Gly Asp Gly His Tyr Arg Phe Pro Ala Phe Pro Tyr
1               5                   10                  15

<210> SEQ ID NO 121
<211> LENGTH: 17
<212> TYPE: PRT
<213> ORGANISM: Mus musculus

<400> SEQUENCE: 121

Thr Ile Asp Pro Ser Asp Ser Glu Thr His Tyr Asn Leu Gln Phe Lys

```
                 1               5                  10                 15

Asp

<210> SEQ ID NO 122
<211> LENGTH: 15
<212> TYPE: PRT
<213> ORGANISM: Mus musculus

<400> SEQUENCE: 122

Gly Ala Phe Tyr Ser Ser Tyr Ser Tyr Trp Ala Trp Phe Ala Tyr
 1               5                  10                 15

<210> SEQ ID NO 123
<211> LENGTH: 5
<212> TYPE: PRT
<213> ORGANISM: Mus musculus

<400> SEQUENCE: 123

Asp Tyr Glu Met His
 1               5

<210> SEQ ID NO 124
<211> LENGTH: 17
<212> TYPE: PRT
<213> ORGANISM: Mus musculus

<400> SEQUENCE: 124

Ala Leu Asp Pro Lys Thr Gly Asp Thr Ala Tyr Ser Gln Lys Phe Lys
 1               5                  10                 15

Gly

<210> SEQ ID NO 125
<211> LENGTH: 6
<212> TYPE: PRT
<213> ORGANISM: Mus musculus

<400> SEQUENCE: 125

Phe Tyr Ser Tyr Thr Tyr
 1               5

<210> SEQ ID NO 126
<211> LENGTH: 5
<212> TYPE: PRT
<213> ORGANISM: Mus musculus

<400> SEQUENCE: 126

Ile Asn Ala Met Asn
 1               5

<210> SEQ ID NO 127
<211> LENGTH: 19
<212> TYPE: PRT
<213> ORGANISM: Mus musculus

<400> SEQUENCE: 127

Arg Ile Arg Ser Glu Ser Asn Asn Tyr Ala Thr Tyr Tyr Gly Asp Ser
 1               5                  10                 15

Val Lys Asp

<210> SEQ ID NO 128
<211> LENGTH: 8
<212> TYPE: PRT
<213> ORGANISM: Mus musculus
```

<400> SEQUENCE: 128

Glu Val Thr Thr Ser Phe Ala Tyr
1               5

<210> SEQ ID NO 129
<211> LENGTH: 5
<212> TYPE: PRT
<213> ORGANISM: Mus musculus

<400> SEQUENCE: 129

Ala Ser Ala Met Asn
1               5

<210> SEQ ID NO 130
<211> LENGTH: 19
<212> TYPE: PRT
<213> ORGANISM: Mus musculus

<400> SEQUENCE: 130

Arg Ile Arg Ser Lys Ser Asn Asn Tyr Ala Ile Tyr Tyr Ala Asp Ser
1               5                   10                  15

Val Lys Asp

<210> SEQ ID NO 131
<211> LENGTH: 12
<212> TYPE: PRT
<213> ORGANISM: Mus musculus

<400> SEQUENCE: 131

Asp Pro Gly Tyr Tyr Gly Asn Pro Trp Phe Ala Tyr
1               5                   10

<210> SEQ ID NO 132
<211> LENGTH: 5
<212> TYPE: PRT
<213> ORGANISM: Mus musculus

<400> SEQUENCE: 132

Asp Tyr Ser Met His
1               5

<210> SEQ ID NO 133
<211> LENGTH: 17
<212> TYPE: PRT
<213> ORGANISM: Mus musculus

<400> SEQUENCE: 133

Trp Ile Asn Thr Glu Thr Gly Glu Pro Thr Tyr Ala Asp Asp Phe Lys
1               5                   10                  15

Gly

<210> SEQ ID NO 134
<211> LENGTH: 2
<212> TYPE: PRT
<213> ORGANISM: Mus musculus

<400> SEQUENCE: 134

Leu Tyr
1

<210> SEQ ID NO 135
<211> LENGTH: 16
<212> TYPE: PRT
<213> ORGANISM: Mus musculus

<400> SEQUENCE: 135

Asn Ile Trp Trp His Asp Asp Lys Tyr Tyr Asn Ser Ala Leu Lys Ser
1               5                   10                  15

<210> SEQ ID NO 136
<211> LENGTH: 14
<212> TYPE: PRT
<213> ORGANISM: Mus musculus

<400> SEQUENCE: 136

Ile Ala Pro Arg Tyr Asn Lys Tyr Glu Gly Phe Phe Ala Phe
1               5                   10

<210> SEQ ID NO 137
<211> LENGTH: 16
<212> TYPE: PRT
<213> ORGANISM: Mus musculus

<400> SEQUENCE: 137

Lys Ser Ser Gln Ser Leu Leu Asp Ser Asp Gly Lys Thr Tyr Leu Asn
1               5                   10                  15

<210> SEQ ID NO 138
<211> LENGTH: 7
<212> TYPE: PRT
<213> ORGANISM: Mus musculus

<400> SEQUENCE: 138

Leu Val Ser Lys Leu Asp Ser
1               5

<210> SEQ ID NO 139
<211> LENGTH: 9
<212> TYPE: PRT
<213> ORGANISM: Mus musculus

<400> SEQUENCE: 139

Trp Gln Gly Thr His Phe Pro Leu Thr
1               5

<210> SEQ ID NO 140
<211> LENGTH: 11
<212> TYPE: PRT
<213> ORGANISM: Mus musculus

<400> SEQUENCE: 140

Lys Ala Ser Gln Asp Ile Asn Asn Tyr Leu Ser
1               5                   10

<210> SEQ ID NO 141
<211> LENGTH: 7
<212> TYPE: PRT
<213> ORGANISM: Mus musculus

<400> SEQUENCE: 141

Arg Ala Asn Arg Leu Val Asp
1               5

<210> SEQ ID NO 142
<211> LENGTH: 10
<212> TYPE: PRT
<213> ORGANISM: Mus musculus

<400> SEQUENCE: 142

```
Leu Gln Cys Asp Glu Phe Pro Pro Trp Thr
1               5                   10
```

<210> SEQ ID NO 143
<211> LENGTH: 16
<212> TYPE: PRT
<213> ORGANISM: Mus musculus

<400> SEQUENCE: 143

```
Arg Ser Ser Gln Ser Leu Val His Ser Asn Gly Asn Thr Tyr Leu His
1               5                   10                  15
```

<210> SEQ ID NO 144
<211> LENGTH: 7
<212> TYPE: PRT
<213> ORGANISM: Mus musculus

<400> SEQUENCE: 144

```
Lys Val Ser Asn Arg Phe Ser
1               5
```

<210> SEQ ID NO 145
<211> LENGTH: 9
<212> TYPE: PRT
<213> ORGANISM: Mus musculus

<400> SEQUENCE: 145

```
Ser Gln Ser Thr His Val Pro Trp Thr
1               5
```

<210> SEQ ID NO 146
<211> LENGTH: 16
<212> TYPE: PRT
<213> ORGANISM: Mus musculus

<400> SEQUENCE: 146

```
Arg Ser Ser Lys Ser Leu Leu His Ser Asn Gly Ile Thr Tyr Leu Tyr
1               5                   10                  15
```

<210> SEQ ID NO 147
<211> LENGTH: 7
<212> TYPE: PRT
<213> ORGANISM: Mus musculus

<400> SEQUENCE: 147

```
Gln Met Ser Asn Leu Ala Ser
1               5
```

<210> SEQ ID NO 148
<211> LENGTH: 9
<212> TYPE: PRT
<213> ORGANISM: Mus musculus

<400> SEQUENCE: 148

```
Ala Gln Asn Leu Glu Leu Pro Tyr Thr
1               5
```

<210> SEQ ID NO 149
<211> LENGTH: 11
<212> TYPE: PRT
<213> ORGANISM: Mus musculus

<400> SEQUENCE: 149

```
Lys Ala Ser Gln Asp Ile Asn Lys Asn Ile Ile
1               5                   10
```

<210> SEQ ID NO 150
<211> LENGTH: 7
<212> TYPE: PRT
<213> ORGANISM: Mus musculus

<400> SEQUENCE: 150

Tyr Thr Ser Thr Leu Gln Pro
1               5

<210> SEQ ID NO 151
<211> LENGTH: 6
<212> TYPE: PRT
<213> ORGANISM: Mus musculus

<400> SEQUENCE: 151

Leu Gln Tyr Asp Asn Leu
1               5

<210> SEQ ID NO 152
<211> LENGTH: 11
<212> TYPE: PRT
<213> ORGANISM: Mus musculus

<400> SEQUENCE: 152

Arg Ala Ser His Ser Ile Ser Asn Phe Leu His
1               5                   10

<210> SEQ ID NO 153
<211> LENGTH: 7
<212> TYPE: PRT
<213> ORGANISM: Mus musculus

<400> SEQUENCE: 153

Tyr Ala Ser Gln Ser Ile Ser
1               5

<210> SEQ ID NO 154
<211> LENGTH: 9
<212> TYPE: PRT
<213> ORGANISM: Mus musculus

<400> SEQUENCE: 154

Gln Gln Ser Asn Ile Trp Ser Leu Thr
1               5

<210> SEQ ID NO 155
<211> LENGTH: 15
<212> TYPE: PRT
<213> ORGANISM: Mus musculus

<400> SEQUENCE: 155

Arg Ala Ser Glu Ser Val Glu Tyr Tyr Gly Thr Ser Leu Met Gln
1               5                   10                  15

<210> SEQ ID NO 156
<211> LENGTH: 7
<212> TYPE: PRT
<213> ORGANISM: Mus musculus

<400> SEQUENCE: 156

Gly Ala Ser Asn Val Glu Ser
1               5

<210> SEQ ID NO 157
<211> LENGTH: 9

```
<212> TYPE: PRT
<213> ORGANISM: Mus musculus

<400> SEQUENCE: 157

Gln Gln Ser Arg Lys Val Pro Tyr Thr
1               5

<210> SEQ ID NO 158
<211> LENGTH: 9
<212> TYPE: PRT
<213> ORGANISM: Mus musculus

<400> SEQUENCE: 158

Ser Gln Asn Thr His Val Pro Pro Thr
1               5

<210> SEQ ID NO 159
<211> LENGTH: 16
<212> TYPE: PRT
<213> ORGANISM: Mus musculus

<400> SEQUENCE: 159

Lys Ser Ser Lys Ser Leu Leu His Ser Asn Gly Asn Thr Tyr Leu Asn
1               5                   10                  15

<210> SEQ ID NO 160
<211> LENGTH: 7
<212> TYPE: PRT
<213> ORGANISM: Mus musculus

<400> SEQUENCE: 160

Trp Met Ser Asn Leu Ala Ser
1               5

<210> SEQ ID NO 161
<211> LENGTH: 9
<212> TYPE: PRT
<213> ORGANISM: Mus musculus

<400> SEQUENCE: 161

Met Gln His Ile Glu Tyr Pro Phe Thr
1               5

<210> SEQ ID NO 162
<211> LENGTH: 16
<212> TYPE: PRT
<213> ORGANISM: Mus musculus

<400> SEQUENCE: 162

Arg Ser Ser Lys Ser Leu Leu His Ser Tyr Asp Ile Thr Tyr Leu Tyr
1               5                   10                  15

<210> SEQ ID NO 163
<211> LENGTH: 9
<212> TYPE: PRT
<213> ORGANISM: Mus musculus

<400> SEQUENCE: 163

Ala Gln Asn Leu Glu Leu Pro Pro Thr
1               5

<210> SEQ ID NO 164
<211> LENGTH: 10
<212> TYPE: PRT
<213> ORGANISM: Mus musculus
```

-continued

```
<400> SEQUENCE: 164

Ser Ala Ser Ser Val Ser Tyr Met Tyr
1               5                   10

<210> SEQ ID NO 165
<211> LENGTH: 7
<212> TYPE: PRT
<213> ORGANISM: Mus musculus

<400> SEQUENCE: 165

Asp Thr Ser Asn Leu Ala Ser
1               5

<210> SEQ ID NO 166
<211> LENGTH: 9
<212> TYPE: PRT
<213> ORGANISM: Mus musculus

<400> SEQUENCE: 166

Gln Gln Trp Ser Ser Tyr Pro Leu Thr
1               5

<210> SEQ ID NO 167
<211> LENGTH: 16
<212> TYPE: PRT
<213> ORGANISM: Mus musculus

<400> SEQUENCE: 167

Lys Ser Ser Gln Ser Leu Leu His Ser Asp Gly Lys Thr Phe Leu Asn
1               5                   10                  15

<210> SEQ ID NO 168
<211> LENGTH: 7
<212> TYPE: PRT
<213> ORGANISM: Mus musculus

<400> SEQUENCE: 168

Leu Val Ser Arg Leu Asp Ser
1               5

<210> SEQ ID NO 169
<211> LENGTH: 6
<212> TYPE: PRT
<213> ORGANISM: Mus musculus

<400> SEQUENCE: 169

Cys Gln Gly Thr His Phe
1               5

<210> SEQ ID NO 170
<211> LENGTH: 16
<212> TYPE: PRT
<213> ORGANISM: Mus musculus

<400> SEQUENCE: 170

Arg Ser Ser Gln Ser Ile Val His Ser Asn Gly Asn Thr Tyr Leu Glu
1               5                   10                  15

<210> SEQ ID NO 171
<211> LENGTH: 9
<212> TYPE: PRT
<213> ORGANISM: Mus musculus

<400> SEQUENCE: 171

Phe Gln Gly Ser His Val Pro Trp Thr
```

<210> SEQ ID NO 172
<211> LENGTH: 27
<212> TYPE: DNA
<213> ORGANISM: Artificial Sequence
<220> FEATURE:
<223> OTHER INFORMATION: PCR primer

<400> SEQUENCE: 172
cttgtacaca gtgacggaaa cacctat                                          27

<210> SEQ ID NO 173
<211> LENGTH: 27
<212> TYPE: DNA
<213> ORGANISM: Artificial Sequence
<220> FEATURE:
<223> OTHER INFORMATION: PCR primer

<400> SEQUENCE: 173
ataggtgttt ccgtcactgt gtacaag                                          27

<210> SEQ ID NO 174
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 174

Arg Ser Ser Gln Ser Leu Val His Ser Asn Ala Asn Thr Tyr Leu His
1               5                   10                  15

<210> SEQ ID NO 175
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 175

Arg Ser Ser Gln Ser Leu Val His Ser Asn Asp Asn Thr Tyr Leu His
1               5                   10                  15

<210> SEQ ID NO 176
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 176

Arg Ser Ser Gln Ser Leu Val His Ser Asn Glu Asn Thr Tyr Leu His
1               5                   10                  15

<210> SEQ ID NO 177
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 177

Arg Ser Ser Gln Ser Leu Val His Ser Asn Phe Asn Thr Tyr Leu His
1               5                   10                  15

<210> SEQ ID NO 178

```
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 178

Arg Ser Ser Gln Ser Leu Val His Ser Asn His Asn Thr Tyr Leu His
1               5                   10                  15

<210> SEQ ID NO 179
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 179

Arg Ser Ser Gln Ser Leu Val His Ser Asn Asn Asn Thr Tyr Leu His
1               5                   10                  15

<210> SEQ ID NO 180
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 180

Arg Ser Ser Gln Ser Leu Val His Ser Asn Thr Asn Thr Tyr Leu His
1               5                   10                  15

<210> SEQ ID NO 181
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 181

Arg Ser Ser Gln Ser Leu Val His Ser Asn Gln Asn Thr Tyr Leu His
1               5                   10                  15

<210> SEQ ID NO 182
<211> LENGTH: 17
<212> TYPE: PRT
<213> ORGANISM: Artificial Sequence
<220> FEATURE:
<223> OTHER INFORMATION: mutant antibody L chain

<400> SEQUENCE: 182

Arg Ser Ser Gln Ser Leu Val His Ser Asn Gly Ile Asn Thr Tyr Leu
1               5                   10                  15

His

<210> SEQ ID NO 183
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 183

Arg Ser Ser Gln Ser Leu Val His Ser Asn Lys Asn Thr Tyr Leu His
1               5                   10                  15

<210> SEQ ID NO 184
```

```
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 184

Arg Ser Ser Gln Ser Leu Val His Ser Asn Leu Asn Thr Tyr Leu His
1               5                   10                  15

<210> SEQ ID NO 185
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 185

Arg Ser Ser Gln Ser Leu Val His Ser Asn Ser Asn Thr Tyr Leu His
1               5                   10                  15

<210> SEQ ID NO 186
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 186

Arg Ser Ser Gln Ser Leu Val His Ser Asn Trp Asn Thr Tyr Leu His
1               5                   10                  15

<210> SEQ ID NO 187
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 187

Arg Ser Ser Gln Ser Leu Val His Ser Asn Tyr Asn Thr Tyr Leu His
1               5                   10                  15

<210> SEQ ID NO 188
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 188

Arg Ser Ser Gln Ser Leu Val His Ser Asn Arg Asn Thr Tyr Leu His
1               5                   10                  15

<210> SEQ ID NO 189
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 189

Arg Ser Ser Gln Ser Leu Val His Ser Asn Val Asn Thr Tyr Leu His
1               5                   10                  15

<210> SEQ ID NO 190
<211> LENGTH: 16
<212> TYPE: PRT
```

```
<213> ORGANISM: Artificial Sequence
<220> FEATURE:
<223> OTHER INFORMATION: mutant antibody L chain

<400> SEQUENCE: 190

Arg Ser Ser Gln Ser Leu Val His Ser Asn Pro Asn Thr Tyr Leu His
1               5                   10                  15

<210> SEQ ID NO 191
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 191

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Ala Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 192
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 192

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Asp Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 193
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 193
```

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Glu Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110
```

<210> SEQ ID NO 194
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 194

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Phe Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110
```

<210> SEQ ID NO 195
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 195

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn His Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Ser Gln Asn
                85                  90                  95
```

```
Thr His Val Pro Pro Thr Phe Gly Gln Gly Thr Lys Leu Glu Ile Lys
            100                 105                 110

<210> SEQ ID NO 196
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 196

Asp Val Val Met Thr Gln Ser Pro Leu Ser Leu Pro Val Thr Pro Gly
1               5                  10                  15

Glu Pro Ala Ser Ile Ser Cys Arg Ser Ser Gln Ser Leu Val His Ser
            20                  25                  30

Asn Asn Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 197
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 197

Asp Val Val Met Thr Gln Ser Pro Leu Ser Leu Pro Val Thr Pro Gly
1               5                  10                  15

Glu Pro Ala Ser Ile Ser Cys Arg Ser Ser Gln Ser Leu Val His Ser
            20                  25                  30

Asn Thr Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 198
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 198

Asp Val Val Met Thr Gln Ser Pro Leu Ser Leu Pro Val Thr Pro Gly
1               5                  10                  15

Glu Pro Ala Ser Ile Ser Cys Arg Ser Ser Gln Ser Leu Val His Ser
```

```
                    20                  25                  30

Asn Gln Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 199
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 199

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Ile Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 200
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 200

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Lys Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110
```

```
<210> SEQ ID NO 201
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 201
```

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Leu Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

```
<210> SEQ ID NO 202
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 202
```

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Ser Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

```
<210> SEQ ID NO 203
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 203
```

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Trp Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
                100                 105                 110

<210> SEQ ID NO 204
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 204

Asp Val Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Val His Ser
                20                  25                  30

Asn Tyr Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
                100                 105                 110

<210> SEQ ID NO 205
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 205

Asp Val Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Val His Ser
                20                  25                  30

Asn Arg Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
                100                 105                 110

<210> SEQ ID NO 206
<211> LENGTH: 112
<212> TYPE: PRT
<213> ORGANISM: Artificial Sequence
<220> FEATURE:

-continued

<223> OTHER INFORMATION: mutant antibody L chain

<400> SEQUENCE: 206

Asp Val Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Val His Ser
            20                  25                  30
Asn Val Asn Thr Tyr Leu His Trp Tyr Leu Gln Lys Pro Gly Gln Ser
        35                  40                  45
Pro Gln Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Ser Gln Asn
                85                  90                  95
Thr His Val Pro Pro Thr Phe Gly Gln Gly Thr Lys Leu Glu Ile Lys
            100                 105                 110

<210> SEQ ID NO 207
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 207

Asp Val Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Val His Ser
            20                  25                  30
Asn Pro Asn Thr Tyr Leu His Trp Tyr Leu Gln Lys Pro Gly Gln Ser
        35                  40                  45
Pro Gln Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Ser Gln Asn
                85                  90                  95
Thr His Val Pro Pro Thr Phe Gly Gln Gly Thr Lys Leu Glu Ile Lys
            100                 105                 110

ANTI-GLYPICAN 3 ANTIBODY

This application is the National Stage of International Application No. PCT/JP2005/013103, filed Jul. 8, 2005, which claims the benefit of Japanese Patent Application Serial No. 2004-203637, filed on Jul. 9, 2004. The contents of these applications are hereby incorporated by reference in their entireties.

BACKGROUND OF THE INVENTION

1. Field of the Invention

The present invention relates to an anti-glypican 3 antibody, a cell growth inhibitor and an anticancer agent containing the antibody as an active ingredient.

2. Description of Related Art

Glypican 3 (GPC3) is one of the glypican family of heparan sulfate proteoglycans that are present on cell surfaces. It is suggested that GPC3 may be involved in cell division in development or cancer cell growth, however, its function has not been well elucidated yet.

It has been found that a certain type of antibody binding to GPC3 has a cell growth-inhibiting activity via an antibody-dependent cell-mediated cytotoxicity (ADCC) activity and a complement-dependent cytotoxicity (CDC) activity (International Patent Application WO 2003/000883). In addition, it has been suggested that GPC3 is cleaved in vivo and secreted into blood as a secreted form of GPC3, and the diagnosis of cancers may be possible by using an antibody capable of detecting the secreted form of GPC3 (International Patent Applications WO 2004/022739, WO 03/100429 and WO 2004/018667).

When developing an anticancer agent based on the cytotoxicity activity of an antibody, it is preferred that the antibody to be used has high ADCC activity or CDC activity. Accordingly, an anti-GPC3 antibody having a high cytotoxicity activity has been desired as an antibody recognizing GPC3.

An object of the present invention is to provide an anti-GPC3 antibody having a higher ADCC activity and CDC activity compared with those of a conventional antibody.

SUMMARY OF THE INVENTION

The present inventors have succeeded in obtaining an antibody having a higher cytotoxicity activity compared with that of a conventional anti-glypican 3 antibody. Furthermore, they analyzed epitopes for such an antibody and succeeded in determining the regions on GPC 3 recognized by the antibody with a high cytotoxicity activity.

In one aspect, the present invention provides an antibody comprising a heavy chain variable region having CDRs 1, 2 and 3 of any one of (1)-(12):
(1) CDR1 comprising the amino acid sequence set forth in SEQ ID NO: 123, CDR2 comprising the amino acid sequence set forth in SEQ ID NO: 124, and CDR3 comprising the amino acid sequence set forth in SEQ ID NO: 125;
(2) CDR1 comprising the amino acid sequence set forth in SEQ ID NO: 109, CDR2 comprising the amino acid sequence set forth in SEQ ID NO: 110, and CDR3 comprising the amino acid sequence set forth in SEQ ID NO: 111;
(3) CDR1 comprising the amino acid sequence set forth in SEQ ID NO: 106, CDR2 comprising the amino acid sequence set forth in SEQ ID NO: 107, and CDR3 comprising the amino acid sequence set forth in SEQ ID NO: 108;
(4) CDR1 comprising the amino acid sequence set forth in SEQ ID NO: 132, CDR2 comprising the amino acid sequence set forth in SEQ ID NO: 133, and CDR3 comprising the amino acid sequence set forth in SEQ ID NO: 134;
(5) CDR1 comprising the amino acid sequence set forth in SEQ ID NO: 106, CDR2 comprising the amino acid sequence set forth in SEQ ID NO: 135, and CDR3 comprising the amino acid sequence set forth in SEQ ID NO: 136;
(6) CDR1 comprising the amino acid sequence set forth in SEQ ID NO: 126, CDR2 comprising the amino acid sequence set forth in SEQ ID NO: 127, and CDR3 comprising the amino acid sequence set forth in SEQ ID NO: 128;
(7) CDR1 comprising the amino acid sequence set forth in SEQ ID NO: 129, CDR2 comprising the amino acid sequence set forth in SEQ ID NO: 130, and CDR3 comprising the amino acid sequence set forth in SEQ ID NO: 131;
(8) CDR1 comprising the amino acid sequence set forth in SEQ ID NO: 103, CDR2 comprising the amino acid sequence set forth in SEQ ID NO: 104, and CDR3 comprising the amino acid sequence set forth in SEQ ID NO: 105;
(9) CDR1 comprising the amino acid sequence set forth in SEQ ID NO: 118, CDR2 comprising the amino acid sequence set forth in SEQ ID NO: 121, and CDR3 comprising the amino acid sequence set forth in SEQ ID NO: 122;
(10) CDR1 comprising the amino acid sequence set forth in SEQ ID NO: 115, CDR2 comprising the amino acid sequence set forth in SEQ ID NO: 116, and CDR3 comprising the amino acid sequence set forth in SEQ ID NO: 117;
(11) CDR1 comprising the amino acid sequence set forth in SEQ ID NO: 112, CDR2 comprising the amino acid sequence set forth in SEQ ID NO: 113, and CDR3 comprising the amino acid sequence set forth in SEQ ID NO: 114; or
(12) CDR1 comprising the amino acid sequence set forth in SEQ ID NO: 118, CDR2 comprising the amino acid sequence set forth in SEQ ID NO: 119, and CDR3 comprising the amino acid sequence set forth in SEQ ID NO: 120.

In another aspect, the invention provides an antibody comprising a light chain variable region having CDRs 1, 2 and 3 of any one of (1)-(13):
(1) CDR1 comprising the amino acid sequence set forth in SEQ ID NO: 143, CDR2 comprising the amino acid sequence set forth in SEQ ID NO: 144, and CDR3 comprising the amino acid sequence set forth in SEQ ID NO: 158;
(2) CDR1 comprising the amino acid sequence set forth in SEQ ID NO: 143, CDR2 comprising the amino acid sequence set forth in SEQ ID NO: 144, and CDR3 comprising the amino acid sequence set forth in SEQ ID NO: 145;
(3) CDR1 comprising the amino acid sequence set forth in SEQ ID NO: 140, CDR2 comprising the amino acid sequence set forth in SEQ ID NO: 141, and CDR3 comprising the amino acid sequence set forth in SEQ ID NO: 142;
(4) CDR1 comprising the amino acid sequence set forth in SEQ ID NO: 167, CDR2 comprising the amino acid sequence set forth in SEQ ID NO: 168, and CDR3 comprising the amino acid sequence set forth in SEQ ID NO: 169;
(5) CDR1 comprising the amino acid sequence set forth in SEQ ID NO: 170, CDR2 comprising the amino acid sequence set forth in SEQ ID NO: 144, and CDR3 comprising the amino acid sequence set forth in SEQ ID NO: 171;
(6) CDR1 comprising the amino acid sequence set forth in SEQ ID NO: 159, CDR2 comprising the amino acid sequence set forth in SEQ ID NO: 160, and CDR3 comprising the amino acid sequence set forth in SEQ ID NO: 161;
(7) CDR1 comprising the amino acid sequence set forth in SEQ ID NO: 162, CDR2 comprising the amino acid sequence set forth in SEQ ID NO: 147, and CDR3 comprising the amino acid sequence set forth in SEQ ID NO: 163;
(8) CDR1 comprising the amino acid sequence set forth in SEQ ID NO: 164, CDR2 comprising the amino acid sequence set forth in SEQ ID NO: 165, and CDR3 comprising the amino acid sequence set forth in SEQ ID NO: 166;
(9) CDR1 comprising the amino acid sequence set forth in SEQ ID NO: 137, CDR2 comprising the amino acid sequence set forth in SEQ ID NO: 138, and CDR3 comprising the amino acid sequence set forth in SEQ ID NO: 139;
(10) CDR1 comprising the amino acid sequence set forth in SEQ ID NO: 155, CDR2 comprising the amino acid sequence set forth in SEQ ID NO: 156, and CDR3 comprising the amino acid sequence set forth in SEQ ID NO: 157;
(11) CDR1 comprising the amino acid sequence set forth in SEQ ID NO: 149, CDR2 comprising the amino acid sequence set forth in SEQ ID NO: 150, and CDR3 comprising the amino acid sequence set forth in SEQ ID NO: 151;
(12) CDR1 comprising the amino acid sequence set forth in SEQ ID NO: 146, CDR2 comprising the amino acid sequence set forth in SEQ ID NO: 147, and CDR3 comprising the amino acid sequence set forth in SEQ ID NO: 148; or
(13) CDR1 comprising the amino acid sequence set forth in SEQ ID NO: 152, CDR2 comprising the amino acid sequence set forth in SEQ ID NO: 153, and CDR3 comprising the amino acid sequence set forth in SEQ ID NO: 154.

Preferably, the antibody of the invention is selected from the group consisting of any one of (1)-(13):
(1) an antibody comprising a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 143, 144 and 158, respectively;
(2) an antibody comprising a heavy chain variable region having CDRs 1, 2 and 3 comprising the amino acid sequence set forth in SEQ ID NO: 109, 110 and 111, respectively, and a light chain variable region having CDRs 1, 2 and 3 comprising the amino acid sequence set forth in SEQ ID NO: 143, 144 and 145, respectively;
(3) an antibody comprising a heavy chain variable region having CDRs 1, 2 and 3 comprising the amino acid sequence set forth in SEQ ID NO: 106, 107 and 108, respectively, and a light chain variable region having CDRs 1, 2 and 3 comprising the amino acid sequence set forth in SEQ ID NO: 140, 141 and 142, respectively;
(4) an antibody comprising a heavy chain variable region having CDRs 1, 2 and 3 comprising the amino acid sequence set forth in SEQ ID NO: 132, 133 and 134, respectively, and a light chain variable region having CDRs 1, 2 and 3 comprising the amino acid sequence set forth in SEQ ID NO: 167, 168 and 169, respectively;
(5) an antibody comprising a heavy chain variable region having CDRs 1, 2 and 3 comprising the amino acid sequence set forth in SEQ ID NO: 106, 135 and 136, respectively, and a light chain variable region having CDRs 1, 2 and 3 comprising the amino acid sequence set forth in SEQ ID NO: 170, 144 and 171, respectively;
(6) an antibody comprising a heavy chain variable region having CDRs 1, 2 and 3 comprising the amino acid sequence set forth in SEQ ID NO: 126, 127 and 128, respectively, and a light chain variable region having CDRs 1, 2 and 3 comprising the amino acid sequence set forth in SEQ ID NO: 159, 160 and 161, respectively;
(7) an antibody comprising a heavy chain variable region having CDRs 1, 2 and 3 comprising the amino acid sequence set forth in SEQ ID NO: 129, 130 and 131, respectively, and a light chain variable region having CDRs 1, 2 and 3 comprising the amino acid sequence set forth in SEQ ID NO: 162, 147 and 163, respectively;
(8) an antibody comprising a heavy chain variable region having CDRs 1, 2 and 3 comprising the amino acid sequence set forth in SEQ ID NO: 129, 130 and 131, respectively, and a light chain variable region having CDRs 1, 2 and 3 comprising the amino acid sequence set forth in SEQ ID NO: 164, 165 and 166, respectively;
(9) an antibody comprising a heavy chain variable region having CDRs 1, 2 and 3 comprising the amino acid sequence set forth in SEQ ID NO: 103, 104 and 105, respectively, and a light chain variable region having CDRs 1, 2 and 3 comprising the amino acid sequence set forth in SEQ ID NO: 137, 138 and 139, respectively;
(10) an antibody comprising a heavy chain variable region having CDRs 1, 2 and 3 comprising the amino acid sequence set forth in SEQ ID NO: 118, 121 and 122, respectively, and a light chain variable region having CDRs 1, 2 and 3 comprising the amino acid sequence set forth in SEQ ID NO: 155, 156 and 157, respectively;
(11) an antibody comprising a heavy chain variable region having CDRs 1, 2 and 3 comprising the amino acid sequence set forth in SEQ ID NO: 115, 116 and 117, respectively, and a light chain variable region having CDRs 1, 2 and 3 comprising the amino acid sequence set forth in SEQ ID NO: 149, 150 and 151, respectively;
(12) an antibody comprising a heavy chain variable region having CDRs 1, 2 and 3 comprising the amino acid sequence set forth in SEQ ID NO: 112, 113 and 114, respectively, and a light chain variable region having CDRs 1, 2 and 3 comprising the amino acid sequence set forth in SEQ ID NO: 146, 147 and 148, respectively; and
(13) an antibody comprising a heavy chain variable region having CDRs 1, 2 and 3 comprising the amino acid sequence set forth in SEQ ID NO: 118, 119 and 120, respectively, and a light chain variable region having CDRs 1, 2 and 3 comprising the amino acid sequence set forth in SEQ ID NO: 152, 153 and 154, respectively.

In another aspect, the invention provides an antibody having a heavy chain variable region of any one of (1)-(7):
(1) a heavy chain variable region comprising the amino acid sequence set forth in SEQ ID NO: 84;
(2) a heavy chain variable region comprising the amino acid sequence set forth in SEQ ID NO: 85;
(3) a heavy chain variable region comprising the amino acid sequence set forth in SEQ ID NO: 86;
(4) a heavy chain variable region comprising the amino acid sequence set forth in SEQ ID NO: 87;
(5) a heavy chain variable region comprising the amino acid sequence set forth in SEQ ID NO: 88;
(6) a heavy chain variable region comprising the amino acid sequence set forth in SEQ ID NO: 89; or
(7) a heavy chain variable region comprising the amino acid sequence set forth in SEQ ID NO: 90.

In another aspect, the invention provides an antibody having a light chain variable region comprising the amino acid sequence set forth in SEQ ID NO: 92.

Preferably, the antibody of the invention is selected from the group consisting of the antibody of any one of (1)-(7):
(1) an antibody comprising a heavy chain variable region comprising the amino acid sequence set forth in SEQ ID NO: 84 and a light chain variable region comprising the amino acid sequence set forth in SEQ ID NO: 92;
(2) an antibody comprising a heavy chain variable region comprising the amino acid sequence set forth in SEQ ID NO: 85 and a light chain variable region comprising the amino acid sequence set forth in SEQ ID NO: 92;
(3) an antibody comprising a heavy chain variable region comprising the amino acid sequence set forth in SEQ ID NO:

86 and a light chain variable region comprising the amino acid sequence set forth in SEQ ID NO: 92;

(4) an antibody comprising a heavy chain variable region comprising the amino acid sequence set forth in SEQ ID NO: 87 and a light chain variable region comprising the amino acid sequence set forth in SEQ ID NO: 92;

(5) an antibody comprising a heavy chain variable region comprising the amino acid sequence set forth in SEQ ID NO: 88 and a light chain variable region comprising the amino acid sequence set forth in SEQ ID NO: 92;

(6) an antibody comprising a heavy chain variable region comprising the amino acid sequence set forth in SEQ ID NO: 89 and a light chain variable region comprising the amino acid sequence set forth in SEQ ID NO: 92; and (7) an antibody comprising a heavy chain variable region comprising the amino acid sequence set forth in SEQ ID NO: 90 and a light chain variable region comprising the amino acid sequence set forth in SEQ ID NO: 92.

In another aspect, the invention provides an antibody comprising a light chain variable region having CDRs 1, 2 and 3 of any one of (1)-(15):

(1) CDR1 comprising the amino acid sequence set forth in SEQ ID NO: 174, CDR2 comprising the amino acid sequence set forth in SEQ ID NO: 144, and CDR3 comprising the amino acid sequence set forth in SEQ ID NO: 158;

(2) CDR1 comprising the amino acid sequence set forth in SEQ ID NO: 175, CDR2 comprising the amino acid sequence set forth in SEQ ID NO: 144, and CDR3 comprising the amino acid sequence set forth in SEQ ID NO: 158;

(3) CDR1 comprising the amino acid sequence set forth in SEQ ID NO: 176, CDR2 comprising the amino acid sequence set forth in SEQ ID NO: 144, and CDR3 comprising the amino acid sequence set forth in SEQ ID NO: 158;

(4) CDR1 comprising the amino acid sequence set forth in SEQ ID NO: 177, CDR2 comprising the amino acid sequence set forth in SEQ ID NO: 144, and CDR3 comprising the amino acid sequence set forth in SEQ ID NO: 158;

(5) CDR1 comprising the amino acid sequence set forth in SEQ ID NO: 178, CDR2 comprising the amino acid sequence set forth in SEQ ID NO: 144, and CDR3 comprising the amino acid sequence set forth in SEQ ID NO: 158;

(6) CDR1 comprising the amino acid sequence set forth in SEQ ID NO: 179, CDR2 comprising the amino acid sequence set forth in SEQ ID NO: 144, and CDR3 comprising the amino acid sequence set forth in SEQ ID NO: 158;

(7) CDR1 comprising the amino acid sequence set forth in SEQ ID NO: 180, CDR2 comprising the amino acid sequence set forth in SEQ ID NO: 144, and CDR3 comprising the amino acid sequence set forth in SEQ ID NO: 158;

(8) CDR1 comprising the amino acid sequence set forth in SEQ ID NO: 181, CDR2 comprising the amino acid sequence set forth in SEQ ID NO: 144, and CDR3 comprising the amino acid sequence set forth in SEQ ID NO: 158;

(9) CDR1 comprising the amino acid sequence set forth in SEQ ID NO: 182, CDR2 comprising the amino acid sequence set forth in SEQ ID NO: 144, and CDR3 comprising the amino acid sequence set forth in SEQ ID NO: 158;

(10) CDR1 comprising the amino acid sequence set forth in SEQ ID NO: 183, CDR2 comprising the amino acid sequence set forth in SEQ ID NO: 144, and CDR3 comprising the amino acid sequence set forth in SEQ ID NO: 158;

(11) CDR1 comprising the amino acid sequence set forth in SEQ ID NO: 184, CDR2 comprising the amino acid sequence set forth in SEQ ID NO: 144, and CDR3 comprising the amino acid sequence set forth in SEQ ID NO: 158;

(12) CDR1 comprising the amino acid sequence set forth in SEQ ID NO: 185, CDR2 comprising the amino acid sequence set forth in SEQ ID NO: 144, and CDR3 comprising the amino acid sequence set forth in SEQ ID NO: 158;

(13) CDR1 comprising the amino acid sequence set forth in SEQ ID NO: 186, CDR2 comprising the amino acid sequence set forth in SEQ ID NO: 144, and CDR3 comprising the amino acid sequence set forth in SEQ ID NO: 158;

(14) CDR1 comprising the amino acid sequence set forth in SEQ ID NO: 187, CDR2 comprising the amino acid sequence set forth in SEQ ID NO: 144, and CDR3 comprising the amino acid sequence set forth in SEQ ID NO: 158; or

(15) CDR1 comprising the amino acid sequence set forth in SEQ ID NO: 188, CDR2 comprising the amino acid sequence set forth in SEQ ID NO: 144, and CDR3 comprising the amino acid sequence set forth in SEQ ID NO: 158.

In another aspect, the invention provides an antibody selected from the group consisting of the antibody of (1)-(15):

(1) an antibody comprising a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 174, 144 and 158, respectively;

(2) an antibody comprising a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 175, 144 and 158, respectively;

(3) an antibody comprising a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 176, 144 and 158, respectively;

(4) an antibody comprising a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 177, 144 and 158, respectively;

(5) an antibody comprising a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 178, 144 and 158, respectively;

(6) an antibody comprising a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 179, 144 and 158, respectively;

(7) an antibody comprising a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 180, 144 and 158, respectively;

(8) an antibody comprising a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 181, 144 and 158, respectively;

(9) an antibody comprising a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 182, 144 and 158, respectively;
(10) an antibody comprising a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 183, 144 and 158, respectively;
(11) an antibody comprising a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 184, 144 and 158, respectively;
(12) an antibody comprising a heavy chain variable region having CDRs 1, 2 and 3 comprising the amino acid sequence set forth in SEQ ID NO: 123, 124, and 125, respectively, and a light chain variable region having CDRs 1, 2 and 3 comprising the amino acid sequence set forth in SEQ ID NO: 185, 144, and 158, respectively;
(13) an antibody comprising a heavy chain variable region having CDRs 1, 2 and 3 comprising the amino acid sequence set forth in SEQ ID NO: 123, 124, and 125, respectively, and a light chain variable region having CDRs 1, 2 and 3 comprising the amino acid sequence set forth in SEQ ID NO: 186, 144 and 158, respectively;
(14) an antibody comprising a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 187, 144 and 158, respectively; and
(15) an antibody comprising a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 188, 144 and 158, respectively.

In further aspect, the invention provides an antibody having a light chain variable region selected from (1)-(15):
(1) a light chain variable region comprising the amino acid sequence set forth in SEQ ID NO: 191;
(2) a light chain variable region comprising the amino acid sequence set forth in SEQ ID NO: 192;
(3) a light chain variable region comprising the amino acid sequence set forth in SEQ ID NO: 193;
(4) a light chain variable region comprising the amino acid sequence set forth in SEQ ID NO: 194;
(5) a light chain variable region comprising the amino acid sequence set forth in SEQ ID NO: 195;
(6) a light chain variable region comprising the amino acid sequence set forth in SEQ ID NO: 196;
(7) a light chain variable region comprising the amino acid sequence set forth in SEQ ID NO: 197;
(8) a light chain variable region comprising the amino acid sequence set forth in SEQ ID NO: 198;
(9) a light chain variable region comprising the amino acid sequence set forth in SEQ ID NO: 199;
(10) a light chain variable region comprising the amino acid sequence set forth in SEQ ID NO: 200;
(11) a light chain variable region comprising the amino acid sequence set forth in SEQ ID NO: 201;
(12) a light chain variable region comprising the amino acid sequence set forth in SEQ ID NO: 202;
(13) a light chain variable region comprising the amino acid sequence set forth in SEQ ID NO: 203;
(14) a light chain variable region comprising the amino acid sequence set forth in SEQ ID NO: 204; and
(15) a light chain variable region comprising the amino acid sequence set forth in SEQ ID NO: 205.

In another aspect, the invention provides an antibody having a light chain variable region selected from the group consisting of (1)-(15):
(1) a light chain variable region comprising the amino acid sequence set forth in SEQ ID NO: 191;
(2) a light chain variable region comprising the amino acid sequence set forth in SEQ ID NO: 192;
(3) a light chain variable region comprising the amino acid sequence set forth in SEQ ID NO: 193;
(4) a light chain variable region comprising the amino acid sequence set forth in SEQ ID NO: 194;
(5) a light chain variable region comprising the amino acid sequence set forth in SEQ ID NO: 195;
(6) a light chain variable region comprising the amino acid sequence set forth in SEQ ID NO: 196;
(7) a light chain variable region comprising the amino acid sequence set forth in SEQ ID NO: 197;
(8) a light chain variable region comprising the amino acid sequence set forth in SEQ ID NO: 198;
(9) a light chain variable region comprising the amino acid sequence set forth in SEQ ID NO: 199;
(10) a light chain variable region comprising the amino acid sequence set forth in SEQ ID NO: 200;
(11) a light chain variable region comprising the amino acid sequence set forth in SEQ ID NO: 201;
(12) a light chain variable region comprising the amino acid sequence set forth in SEQ ID NO: 202;
(13) a light chain variable region comprising the amino acid sequence set forth in SEQ ID NO: 203;
(14) a light chain variable region comprising the amino acid sequence set forth in SEQ ID NO: 204; and
(15) a light chain variable region comprising the amino acid sequence set forth in SEQ ID NO: 205;
and a heavy chain variable region selected from the group consisting of (1)-(7):
(1) a heavy chain variable region comprising the amino acid sequence set forth in SEQ ID NO: 84;
(2) a heavy chain variable region comprising; the amino acid sequence set forth in SEQ ID NO: 85;
(3) a heavy chain variable region comprising the amino acid sequence set forth in SEQ ID NO: 86;
(4) a heavy chain variable region comprising the amino acid sequence set forth in SEQ ID NO: 87;
(5) a heavy chain variable region comprising the amino acid sequence set forth in SEQ ID NO: 88;
(6) a heavy chain variable region comprising the amino acid sequence set forth in SEQ ID NO: 89; and
(7) a heavy chain variable region comprising the amino acid sequence set forth in SEQ ID NO: 90.

The heavy chain variable region, a light chain variable region, and the amino acid sequence of the CDRs 1, 2 and 3, as well as the SEQ ID NOs are summarized in the table below.

| Antibody and variable regions | | SEQ ID NO |
| --- | --- | --- |
| M3C11 | H | 22 |
| M13B3 | H | 23 |
| M1E7 | H | 24 |
| M3B8 | H | 25 |
| M11F1 | H | 26 |
| M19B11 | H | 27 |
| M6B1 | H | 28 |

-continued

| Antibody and variable regions | | SEQ ID NO |
|---|---|---|
| M18D4 | H | 29 |
| M5B9 | H | 30 |
| M10D2 | H | 31 |
| L9G11 | H | 32 |
| M3C11 | L | 44 |
| M13B3 | L | 45 |
| M1E7 | L | 46 |
| M3B8 | L | 47 |
| M11F1 | L | 48 |
| M19B11 | L | 49 |
| M6B1 | L | 50 |
| M18D4 | L | 51 |
| M5B9 | L | 52 |
| M10D2 | L | 53 |
| L9G11 | L | 54 |
| GC199 | H | 60 |
| GC202 | H | 61 |
| GC33 | H | 62 |
| GC179 | H | 63 |
| GC194 | H | 64 |
| GC199 | L | 71 |
| GC202 | L | 72 |
| GC33 | L | 73 |
| GC179 | L | 74 |
| GC194(1) | L | 75 |
| GC194(2) | L | 76 |
| GC33.ver.a | H | 84 |
| GC33.ver.c | H | 85 |
| GC33.ver.f | H | 86 |
| GC33.ver.h | H | 87 |
| GC33.ver.i | H | 88 |
| GC33.ver.j | H | 89 |
| GC33.ver.k | H | 90 |
| GC33.ver.a | L | 92 |
| M13B3(H) | CDR1 | 103 |
| | CDR2 | 104 |
| | CDR3 | 105 |
| M3B8(H) | CDR1 | 106 |
| | CDR2 | 107 |
| | CDR3 | 108 |
| M11F1(H) | CDR1 | 109 |
| | CDR2 | 110 |
| | CDR3 | 111 |
| M5B9(H) | CDR1 | 112 |
| | CDR2 | 113 |
| | CDR3 | 114 |
| M6B1(H) | CDR1 | 115 |
| | CDR2 | 116 |
| | CDR3 | 117 |
| M10D2(H) | CDR1 | 118 |
| | CDR2 | 119 |
| | CDR3 | 120 |
| L9G11(H) | CDR1 | 118 |
| | CDR2 | 121 |
| | CDR3 | 122 |
| GC33(H) | CDR1 | 123 |
| | CDR2 | 124 |
| | CDR3 | 125 |
| GC179(H) | CDR1 | 126 |
| | CDR2 | 127 |
| | CDR3 | 128 |
| GC194(H) | CDR1 | 129 |
| | CDR2 | 130 |
| | CDR3 | 131 |
| GC199(H) | CDR1 | 132 |
| | CDR2 | 133 |
| | CDR3 | 134 |
| GC202(H) | CDR1 | 106 |
| | CDR2 | 135 |
| | CDR3 | 136 |
| M13B3(L) | CDR1 | 137 |
| | CDR2 | 138 |
| | CDR3 | 139 |
| M3B8(L) | CDR1 | 140 |
| | CDR2 | 141 |
| | CDR3 | 142 |
| M11F1(L) | CDR1 | 143 |
| | CDR2 | 144 |
| | CDR3 | 145 |
| M5B9(L) | CDR1 | 146 |
| | CDR2 | 147 |
| | CDR3 | 148 |
| M6B1(L) | CDR1 | 149 |
| | CDR2 | 150 |
| | CDR3 | 151 |
| M10D2(L) | CDR1 | 152 |
| | CDR2 | 153 |
| | CDR3 | 154 |
| L9G11(L) | CDR1 | 155 |
| | CDR2 | 156 |
| | CDR3 | 157 |
| GC33(L) | CDR1 | 143 |
| | CDR2 | 144 |
| | CDR3 | 158 |
| GC179(L) | CDR1 | 159 |
| | CDR2 | 160 |
| | CDR3 | 161 |
| GC194(L)1 | CDR1 | 162 |
| | CDR2 | 147 |
| | CDR3 | 163 |
| GC194(L)2 | CDR1 | 164 |
| | CDR2 | 165 |
| | CDR3 | 166 |
| GC199(L) | CDR1 | 167 |
| | CDR2 | 168 |
| | CDR3 | 169 |
| GC202(L) | CDR1 | 170 |
| | CDR2 | 144 |
| | CDR3 | 171 |
| GC33(L) | G34A | 174 |
| GC33(L) | G34D | 175 |
| GC33(L) | G34E | 176 |
| GC33(L) | G34F | 177 |
| GC33(L) | G34H | 178 |
| GC33(L) | G34N | 179 |
| GC33(L) | G34P | 180 |
| GC33(L) | G34Q | 181 |
| GC33(L) | G34I | 182 |
| GC33(L) | G34K | 183 |
| GC33(L) | G34L | 184 |
| GC33(L) | G34V | 185 |
| GC33(L) | G34W | 186 |
| GC33(L) | G34Y | 187 |
| GC33(L) | G34R | 188 |

Also the invention features an antibody having an activity equivalent to the activity of the antibody described above, wherein one or more amino acid residues are substituted, deleted or added and/or inserted from the amino acid sequences described above.

Preferably, the antibody of the invention is a humanized antibody.

Thus, in another aspect, the invention provides a humanized antibody capable of binding to glypican 3.

In further aspect, the invention provides an antibody capable of binding to a peptide consisting of the sequence of the amino acid residues 524-563 of glypican 3.

Preferably, the antibody of the invention is capable of binding to a peptide consisting of the sequence of the amino acid residues 537-563 of glypican 3. More preferably, the antibody of the invention does not bind to a peptide consisting of the sequence of the amino acid residues 550-563 of glypican 3.

Preferably, the antibody is capable of binding to a peptide consisting of the sequence of the amino acid residues 544-553 of glypican 3 or a peptide consisting of the sequence of the amino acid residues 546-551 of glypican 3.

In still another aspect, the invention provides an antibody capable of binding to an epitope to which a second antibody is capable of binding, wherein said second antibody comprises a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 143, 144 and 158, respectively. Namely, the antibody of the invention is capable of competing in binding to GPC3 with the second antibody.

In a preferred embodiment, the antibody of the invention is capable of binding to glypican 3 and has a high CDC activity against a cell expressing glypican 3 and/or has a high ADCC activity against a cell expressing glypican 3.

In another aspect, the invention provides a polynucleotide coding for a heavy chain variable region or a light chain variable region of the antibody of the invention.

Preferably, the polynucleotide of the invention has the sequence set forth in SEQ ID NOs: 11-21, 33-43, 55-59, 65-70 and 77-83.

In still another aspect, the invention provides a cell-growth inhibitor and an anticancer agent comprising as an active ingredient the antibody of the invention. Preferably, the anticancer agent of the invention is used for treatment of hepatoma.

In further aspect, the invention provides a peptide comprising the sequence of the amino acid residues 524-563 of glypican 3, the sequence of the amino acid residues 537-563 of glypican 3, the sequence of the amino acid residues 544-553 of glypican 3 or the amino acid sequence of the amino acid residues 546-551 of glypican 3.

BRIEF DESCRIPTION OF THE DRAWINGS

FIG. 2 is a table showing the results of epitope classification by a competitive ELISA. The degrees of competitive inhibition against the binding of the biotinylated anti-GPC3 antibody are indicated by percentage. The epitopes were classified into 5 groups, a to e, according to the competitive inhibition pattern.

FIG. 11 shows the results of evaluating the CDC activity of the mouse-human chimeric antibody GC33 to a CHO cell that expresses GPC3.

FIG. 13 shows GPC3-derived sequences contained in GST-fusion proteins (GC-4, 5, 6, 7, 8, 9, 11, 12, 13 and 14) prepared for analyzing the epitope of GC33.

FIG. 16 shows an antibody panel which summarizes isotypes and the results of an ELISA, BIAcore, FACS, an epitope analysis and an immunoprecipitation test for clones derived from a mouse immunized with a soluble form of GPC3.

FIG. 17 shows an antibody panel in which isotypes and the results of an ELISA, FACS and an epitope analysis for clones derived from a mouse immunized with GC-3 are summarized.

DETAILED DESCRIPTION OF THE INVENTION

Antibody

Figure 1:
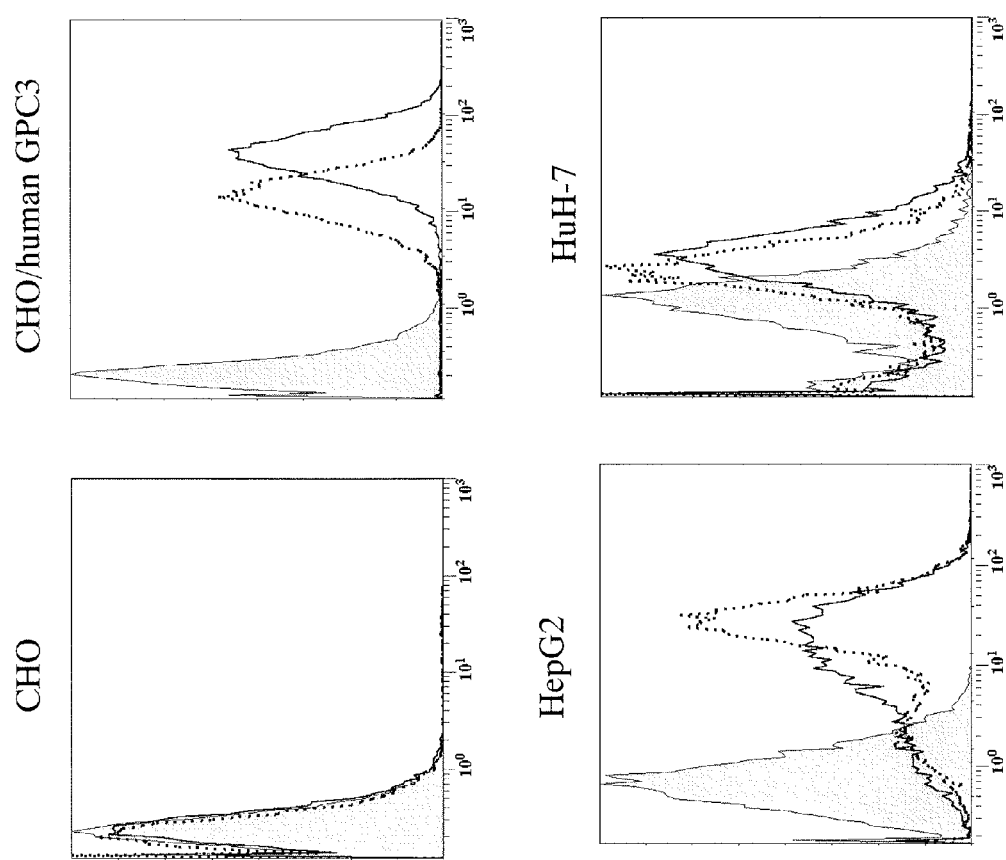
FIG. 1 shows the binding activity of the anti-GPC3 antibody to a CHO cell, a CHO cell expressing full-length GPC3, HepG2 and HuH-7, which was evaluated by flow cytometry. M1E7 (solid line) and M11F1 (dashed line) were used at a concentration of 5 µg/mL, respectively.

The present invention provides antibodies described in the following (I) to (XI).
(I) An antibody containing heavy chain variable regions having CDRs 1, 2 and 3 consisting of the amino acid sequences set forth in SEQ ID NOs: in any of the following (1) to (12):
(1) SEQ ID NOs: 123, 124 and 125 (GC33),
(2) SEQ ID NOs: 109, 110 and 111 (M11F1),
(3) SEQ ID NOs: 106, 107 and 108 (M3B8),
(4) SEQ ID NOs: 132, 133 and 134 (GC199),
(5) SEQ ID NOs: 106, 135 and 136 (GC202),
(6) SEQ ID NOs: 126, 127 and 128 (GC179),
(7) SEQ ID NOs: 129, 130 and 131 (GC194), (8) SEQ ID NOs: 103, 104 and 105 (M13B3),
(9) SEQ ID NOs: 118, 121 and 122 (L9G11),
(10) SEQ ID NOs: 115, 116 and 117 (M6B1),
(11) SEQ ID NOs: 112, 113 and 114 (M5B9), and
(12) SEQ ID NOs: 118, 119 and 120 (M10D2).

Among the antibodies described in (1) to (12), preferred are the antibodies described in (1) to (8), more preferred are the antibodies described in (1) to (5), and particularly preferred is the antibody described in (1). The antibodies described in (1) to (8) recognize the C-terminal peptide of glypican 3 (a peptide comprising the 374th amino acid to the 580th amino acid of glypican 3); and are useful as a therapeutic antibody. In addition, the antibodies described in (9) to (12) recognize the N-terminal peptide of glypican 3 (a peptide comprising from the 1st amino acid to the 373rd amino acid of glypican 3); and are useful as a diagnostic antibody.

(II) An antibody containing light chain variable regions having CDRs 1, 2 and 3 consisting of the amino acid sequences set forth in SEQ ID NOs: in any of the following (1) to (13):
(1) SEQ ID NOs: 143, 144 and 158 (GC33),
(2) SEQ ID NOs: 143, 144 and 145 (M11F1),
(3) SEQ ID NOs: 140, 141 and 142 (M3B8),
(4) SEQ ID NOs: 167, 168 and 169 (GC199),
(5) SEQ ID NOs: 170, 144 and 171 (GC202),
(6) SEQ ID NOs: 159, 160 and 161 (GC179),
(7) SEQ ID NOs: 162, 147 and 163 (GC194 (1)),
(8) SEQ ID NOs: 164, 165 and 166 (GC194 (2)),
(9) SEQ ID NOs: 137, 138 and 139 (M13B3),
(10) SEQ ID NOs: 155, 156 and 157 (L9G11),
(11) SEQ ID NOs: 149, 150 and 151 (M6B1),
(12) SEQ ID NOs: 146, 147 and 148 (M5B9), and
(13) SEQ ID NOs: 152, 153 and 154 (M10D2).

Among the antibodies described in (1) to (13), preferred are the antibodies described in (1) to (8), more preferred are the antibodies described in (1) to (5), and particularly preferred is the antibody described in (1). The antibodies described in (1) to (8) recognize the C-terminal peptide of glypican 3 (a peptide comprising from the 374th amino acid to the 580th amino acid of glypican 3); and are useful as a therapeutic antibody. In addition, the antibodies described in (9) to (13) recognize the N-terminal peptide of glypican 3 (a peptide comprising from the 1st amino acid to the 373rd amino acid of glypican 3); and are useful as a diagnostic antibody.

(III) An antibody selected from the group consisting of the antibodies described in the following (1) to (13):
(1) an antibody containing heavy chain variable regions having CDRs 1, 2 and 3 consisting of the amino acid sequences set forth in SEQ ID NOs: 123, 124 and 125, and light chain variable regions having CDRs 1, 2 and 3 consisting of the amino acid sequences set forth in SEQ ID NOs: 143, 144 and 158 (GC33),
(2) an antibody containing heavy chain variable regions having CDRs 1, 2 and 3 consisting of the amino acid sequences set forth in SEQ ID NOs: 109, 110 and 111, and light chain variable regions having CDRs 1, 2 and 3 consisting of the amino acid sequences set forth in SEQ ID NOs: 143, 144 and 145 (M11F1),
(3) an antibody containing heavy chain variable regions having CDRs 1, 2 and 3 consisting of the amino acid sequences set forth in SEQ ID NOs: 106, 107 and 108, and light chain variable regions having CDRs 1, 2 and 3 consisting of the amino acid sequences set forth in SEQ ID NOs: 140, 141 and 142 (M3B8),
(4) an antibody containing heavy chain variable regions having CDRs 1, 2 and 3 consisting of the amino acid sequences set forth in SEQ ID NOs: 132, 133 and 134, and light chain variable regions having CDRs 1, 2 and 3 consisting of the amino acid sequences set forth in SEQ ID NOs: 167, 168 and 169 (GC199),
(5) an antibody containing heavy chain variable regions having CDRs 1, 2 and 3 consisting of the amino acid sequences set forth in SEQ ID NOs: 106, 135 and 136, and light chain variable regions having CDRs 1, 2 and 3 consisting of the amino acid sequences set forth in SEQ ID NOs: 170, 144 and 171 (GC202),
(6) an antibody containing heavy chain variable regions having CDRs 1, 2 and 3 consisting of the amino acid sequences set forth in SEQ ID NOs: 126, 127 and 128, and light chain variable regions having CDRs 1, 2 and 3 consisting of the amino acid sequences set forth in SEQ ID NOs: 159, 160 and 161 (GC179),
(7) an antibody containing heavy chain variable regions having CDRs 1, 2 and 3 consisting of the amino acid sequences set forth in SEQ ID NOs: 129, 130 and 131, and light chain variable regions having CDRs 1, 2 and 3 consisting of the amino acid sequences set forth in SEQ ID NOs: 162, 147 and 163 (GC194 (1)),
(8) an antibody containing heavy chain variable regions having CDRs 1, 2 and 3 consisting of the amino acid sequences set forth in SEQ ID NOs: 129, 130 and 131, and light chain variable regions having CDRs 1, 2 and 3 consisting of the amino acid sequences set forth in SEQ ID NOs: 164, 165 and 166 (GC194 (2)),
(9) an antibody containing heavy chain variable regions having CDRs 1, 2 and 3 consisting of the amino acid sequences set forth in SEQ ID NOs: 103, 104 and 105, and light chain variable regions having CDRs 1, 2 and 3 consisting of the amino acid sequences set forth in SEQ ID NOs: 137, 138 and 139 (M13B3),
(10) an antibody containing heavy chain variable regions having CDRs 1, 2 and 3 consisting of the amino acid sequences set forth in SEQ ID NOs: 118, 121 and 122, and light chain variable regions having CDRs 1, 2 and 3 consisting of the amino acid sequences set forth in SEQ ID NOs: 155, 156 and 157 (L9G11),
(11) an antibody containing heavy chain variable regions having CDRs 1, 2 and 3 consisting of the amino acid sequences set forth in SEQ ID NOs: 115, 116 and 117, and light chain variable regions having CDRs 1, 2 and 3 consisting of the amino acid sequences set forth in SEQ ID NOs: 149, 150 and 151 (M6B1),
(12) an antibody containing heavy chain variable regions having CDRs 1, 2 and 3 consisting of the amino acid sequences set forth in SEQ ID NOs: 112, 113 and 114, and light chain variable regions having CDRs 1, 2 and 3 consisting of the amino acid sequences set forth in SEQ ID NOs: 146, 147 and 148 (M5B9),
(13) an antibody containing heavy chain variable regions having CDRs 1, 2 and 3 consisting of the amino acid sequences set forth in SEQ ID NOs: 118, 119 and 120, and light chain variable regions having CDRs 1, 2 and 3 consisting of the amino acid sequences set forth in SEQ ID NOs: 152, 153 and 154 (M10D2).

Among the antibodies described in (1) to (13), preferred are the antibodies described in (1) to (8), more preferred are the antibodies described in (1) to (5), and particularly preferred is the antibody described in (1). The antibodies described in (1) to (8) recognize the C-terminal peptide of glypican 3 (a peptide comprising from the 374th amino acid to the 580th amino acid of glypican 3); and are useful as a therapeutic antibody. In addition, the antibodies described in (9) to (13) recognize the N-terminal peptide of glypican 3 (a peptide comprising from the 1st amino acid to the 373rd amino acid of glypican 3); and are useful as a diagnostic antibody.

(IV) An antibody having a heavy chain variable region described in any of the following (1) to (7):
(1) a heavy chain variable region containing the amino acid sequence set forth in SEQ ID NO: 84 (GC33 VH ver.a),
(2) a heavy chain variable region containing the amino acid sequence set forth in SEQ ID NO: 85 (GC33 VH ver.c),
(3) a heavy chain variable region containing the amino acid sequence set forth in SEQ ID NO: 86 (GC33 VH ver.f),
(4) a heavy chain variable region containing the amino acid sequence set forth in SEQ ID NO: 87 (GC33 VH ver.h),
(5) a heavy chain variable region containing the amino acid sequence set forth in SEQ ID NO: 88 (GC33 VH ver.i),
(6) a heavy chain variable region containing the amino acid sequence set forth in SEQ ID NO: 89 (GC33 VH ver.j), and
(7) a heavy chain variable region containing the amino acid sequence set forth in SEQ ID NO: 90 (GC33 VH ver.k).

Among the antibodies described in (1) to (7), particularly preferred are the antibodies described in (2) to (7).

(V) An antibody having a light chain variable region containing the amino acid sequence set forth in SEQ ID NO: 92 (GC33 VL ver.a).

(VI) An antibody selected from the group consisting of the antibodies described in the following (1) to (7):
(1) an antibody having a heavy chain variable region containing the amino acid sequence set forth in SEQ ID NO: 84 (GC33 VH ver.a) and a light chain variable region containing the amino acid sequence set forth in SEQ ID NO: 92 (GC33 VL ver.a),
(2) an antibody having a heavy chain variable region containing the amino acid sequence set forth in SEQ ID NO: 85 (GC33 VH ver.c) and a light chain variable region containing the amino acid sequence set forth in SEQ ID NO: 92 (GC33 VL ver.a),
(3) an antibody having a heavy chain variable region containing the amino acid sequence set forth in SEQ ID NO: 86 (GC33 VH ver.f) and a light chain variable region containing the amino acid sequence set forth in SEQ ID NO: 92 (GC33 VL ver.a),
(4) an antibody having a heavy chain variable region containing the amino acid sequence set forth in SEQ ID NO: 87 (GC33 VH ver.h) and a light chain variable region containing the amino acid sequence set forth in SEQ ID NO: 92 (GC33 VL ver.a),
(5) an antibody having a heavy chain variable region containing the amino acid sequence set forth in SEQ ID NO: 88 (GC33 VH ver.i) and a light chain variable region containing the amino acid sequence set forth in SEQ ID NO: 92 (GC33 VL ver.a),
(6) an antibody having a heavy chain variable region containing the amino acid sequence set forth in SEQ ID NO: 89 (GC33 VH ver.j) and a light chain variable region containing the amino acid sequence set forth in SEQ ID NO: 92 (GC33 VL ver.a), and
(7) an antibody having a heavy chain variable region containing the amino acid sequence set forth in SEQ ID NO: 90 (GC33 VH ver.k) and a light chain variable region containing the amino acid sequence set forth in SEQ ID NO: 92 (GC33 VL ver.a).

Among the antibodies described in (1) to (7), particularly preferred are the antibodies described in (2) to (7).

(VII) An antibody described in any of the following (1) to (15):
(1) an antibody containing light chain variable regions having CDRs 1, 2 and 3 consisting of the amino acid sequences set forth in SEQ ID NOs: 174, 144 and 158,
(2) an antibody containing light chain variable regions having CDRs 1, 2 and 3 consisting of the amino acid sequences set forth in SEQ ID NOs: 175, 144 and 158,
(3) an antibody containing light chain variable regions having CDRs 1, 2 and 3 consisting of the amino acid sequences set forth in SEQ ID NOs: 176, 144 and 158,
(4) an antibody containing light chain variable regions having CDRs 1, 2 and 3 consisting of the amino acid sequences set forth in SEQ ID NOs: 177, 144 and 158,
(5) an antibody containing light chain variable regions having CDRs 1, 2 and 3 consisting of the amino acid sequences set forth in SEQ ID NOs: 178, 144 and 158,
(6) an antibody containing light chain variable regions having CDRs 1, 2 and 3 consisting of the amino acid sequences set forth in SEQ ID NOs: 179, 144 and 158,
(7) an antibody containing light chain variable regions having CDRs 1, 2 and 3 consisting of the amino acid sequences set forth in SEQ ID NOs: 180, 144 and 158,
(8) an antibody containing light chain variable regions having CDRs 1, 2 and 3 consisting of the amino acid sequences set forth in SEQ ID NOs: 181, 144 and 158,
(9) an antibody containing light chain variable regions having CDRs 1, 2 and 3 consisting of the amino acid sequences set forth in SEQ ID NOs: 182, 144 and 158,
(10) an antibody containing light chain variable regions having CDRs 1, 2 and 3 consisting of the amino acid sequences set forth in SEQ ID NOs: 183, 144 and 158,
(11) an antibody containing light chain variable regions having CDRs 1, 2 and 3 consisting of the amino acid sequences set forth in SEQ ID NOs: 184, 144 and 158,
(12) an antibody containing light chain variable regions having CDRs 1, 2 and 3 consisting of the amino acid sequences set forth in SEQ ID NOs: 185, 144 and 158,
(13) an antibody containing light chain variable regions having CDRs 1, 2 and 3 consisting of the amino acid sequences set forth in SEQ ID NOs: 186, 144 and 158,
(14) an antibody containing light chain variable regions having CDRs 1, 2 and 3 consisting of the amino acid sequences set forth in SEQ ID NOs: 187, 144 and 158, and
(15) an antibody containing light chain variable regions having CDRs 1, 2 and 3 consisting of the amino acid sequences set forth in SEQ ID NOs: 188, 144 and 158.

Among the antibodies described in (1) to (15), preferred is the antibody described in (15).

(VIII) An antibody described in any of the following (1) to (15):
(1) an antibody containing heavy chain variable regions having CDRs 1, 2 and 3 consisting of the amino acid sequences set forth in SEQ ID NOs: 123, 124 and 125 and light chain variable regions having CDRs 1, 2 and 3 consisting of the amino acid sequences set forth in SEQ ID NOs: 174, 144 and 158,
(2) an antibody containing heavy chain variable regions having CDRs 1, 2 and 3 consisting of the amino acid sequences set forth in SEQ ID NOs: 123, 124 and 125 and light chain variable regions having CDRs 1, 2 and 3 consisting of the amino acid sequences set forth in SEQ ID NOs: 175, 144 and 158,
(3) an antibody containing heavy chain variable regions having CDRs 1, 2 and 3 consisting of the amino acid sequences set forth in SEQ ID NOs: 123, 124 and 125 and light chain variable regions having CDRs 1, 2 and 3 consisting of the amino acid sequences set forth in SEQ ID NOs: 176, 144 and 158, (4) an antibody containing heavy chain variable regions having CDRs 1, 2 and 3 consisting of the amino acid sequences set forth in SEQ ID NOs: 123, 124 and 125 and light chain variable regions having CDRs 1, 2 and 3 consisting of the amino acid sequences set forth in SEQ ID NOs: 177, 144 and 158,
(5) an antibody containing heavy chain variable regions having CDRs 1, 2 and 3 consisting of the amino acid sequences set forth in SEQ ID NOs: 123, 124 and 125 and light chain variable regions having CDRs 1, 2 and 3 consisting of the amino acid sequences set forth in SEQ ID NOs: 178, 144 and 158,
(6) an antibody containing heavy chain variable regions having CDRs 1, 2 and 3 consisting of the amino acid sequences set forth in SEQ ID NOs: 123, 124 and 125 and light chain variable regions having CDRs 1, 2 and 3 consisting of the amino acid sequences set forth in SEQ ID NOs: 179, 144 and 158,
(7) an antibody containing heavy chain variable regions having CDRs 1, 2 and 3 consisting of the amino acid sequences set forth in SEQ ID NOs: 123, 124 and 125 and light chain variable regions having CDRs 1, 2 and 3 consisting of the amino acid sequences set forth in SEQ ID NOs: 180, 144 and 158,
(8) an antibody containing heavy chain variable regions having CDRs 1, 2 and 3 consisting of the amino acid sequences set forth in SEQ ID NOs: 123, 124 and 125 and light chain variable regions having CDRs 1, 2 and 3 consisting of the amino acid sequences set forth in SEQ ID NOs: 181, 144 and 158,
(9) an antibody containing heavy chain variable regions having CDRs 1, 2 and 3 consisting of the amino acid sequences set forth in SEQ ID NOs: 123, 124 and 125 and light chain variable regions having CDRs 1, 2 and 3 consisting of the amino acid sequences set forth in SEQ ID NOs: 182, 144 and 158,
(10) an antibody containing heavy chain variable regions having CDRs 1, 2 and 3 consisting of the amino acid sequences set forth in SEQ ID NOs: 123, 124 and 125 and light chain variable regions having CDRs 1, 2 and 3 consisting of the amino acid sequences set forth in SEQ ID NOs: 183, 144 and 158,
(11) an antibody containing heavy chain variable regions having CDRs 1, 2 and 3 consisting of the amino acid sequences set forth in SEQ ID NOs: 123, 124 and 125 and light chain variable regions having CDRs 1, 2 and 3 consisting of the amino acid sequences set forth in SEQ ID NOs: 184, 144 and 158,
(12) an antibody containing heavy chain variable regions having CDRs 1, 2 and 3 consisting of the amino acid sequences set forth in SEQ ID NOs: 123, 124 and 125 and light chain variable regions having CDRs 1, 2 and 3 consisting of the amino acid sequences set forth in SEQ ID NOs: 185, 144 and 158,
(13) an antibody containing heavy chain variable regions having CDRs 1, 2 and 3 consisting of the amino acid sequences set forth in SEQ ID NOs: 123, 124 and 125 and light chain variable regions having CDRs 1, 2 and 3 consisting of the amino acid sequences set forth in SEQ ID NOs: 186, 144 and 158,
(14) an antibody containing heavy chain variable regions having CDRs 1, 2 and 3 consisting of the amino acid sequences set forth in SEQ ID NOs: 123, 124 and 125 and light chain variable regions having CDRs 1, 2 and 3 consisting of the amino acid sequences set forth in SEQ ID NOs: 187, 144 and 158, and
(15) an antibody containing heavy chain variable regions having CDRs 1, 2 and 3 consisting of the amino acid sequences set forth in SEQ ID NOs: 123, 124 and 125 and light chain variable regions having CDRs 1, 2 and 3 consisting of the amino acid sequences set forth in SEQ ID NOs: 188, 144 and 158.
Among the antibodies described in (1) to (15), preferred is the antibody described in (15).
(IX) An antibody described in any of the following (1) to (15):
(1) an antibody having a light chain variable region containing the amino acid sequence set forth in SEQ ID NO: 191,
(2) an antibody having a light chain variable region containing the amino acid sequence set forth in SEQ ID NO: 192,
(3) an antibody having a light chain variable region containing the amino acid sequence set forth in SEQ ID NO: 193,
(4) an antibody having a light chain variable region containing the amino acid sequence set forth in SEQ ID NO: 194,
(5) an antibody having a light chain variable region containing the amino acid sequence set forth in SEQ ID NO: 195,
(6) an antibody having a light chain variable region containing the amino acid sequence set forth in SEQ ID NO: 196,
(7) an antibody having a light chain variable region containing the amino acid sequence set forth in SEQ ID NO: 197,
(8) an antibody having a light chain variable region containing the amino acid sequence set forth in SEQ ID NO: 198,
(9) an antibody having a light chain variable region containing the amino acid sequence set forth in SEQ ID NO: 199,
(10) an antibody having a light chain variable region containing the amino acid sequence set forth in SEQ ID NO: 200,
(11) an antibody having a light chain variable region containing the amino acid sequence set forth in SEQ ID NO: 201,
(12) an antibody having a light chain variable region containing the amino acid sequence set forth in SEQ ID NO: 202,
(13) an antibody having a light chain variable region containing the amino acid sequence set forth in SEQ ID NO: 203,
(14) an antibody having a light chain variable region containing the amino acid sequence set forth in SEQ ID NO: 204, and
(15) an antibody having a light chain variable region containing the amino acid sequence set forth in SEQ ID NO: 205.
Among the antibodies described in (1) to (15), preferred is the antibody described in (15).
(X) An antibody having a light chain variable region selected from the group consisting of the light chain variable regions described in the following (1) to (15):
(1) a light chain variable region containing the amino acid sequence set forth in SEQ ID NO: 191,
(2) a light chain variable region containing the amino acid sequence set forth in SEQ ID NO: 192,
(3) a light chain variable region containing the amino acid sequence set forth in SEQ ID NO: 193,
(4) a light chain variable region containing the amino acid sequence set forth in SEQ ID NO: 194,
(5) a light chain variable region containing the amino acid sequence set forth in SEQ ID NO: 195,
(6) a light chain variable region containing the amino acid sequence set forth in SEQ ID NO: 196,
(7) a light chain variable region containing the amino acid sequence set forth in SEQ ID NO: 197,
(8) a light chain variable region containing the amino acid sequence set forth in SEQ ID NO: 198,
(9) a light chain variable region containing the amino acid sequence set forth in SEQ ID NO: 199,
(10) a light chain variable region containing the amino acid sequence set forth in SEQ ID NO: 200,
(11) a light chain variable region containing the amino acid sequence set forth in SEQ ID NO: 201,

(12) a light chain variable region containing the amino acid sequence set forth in SEQ ID NO: 202,
(13) a light chain variable region containing the amino acid sequence set forth in SEQ ID NO: 203,
(14) a light chain variable region containing the amino acid sequence set forth in SEQ ID NO: 204, and
(15) a light chain variable region containing the amino acid sequence set forth in SEQ ID NO: 205, and a heavy chain variable region selected from the group consisting of the heavy chain variable regions described in the following (1) to (7):
(1) a heavy chain variable region containing the amino acid sequence set forth in SEQ ID NO: 84,
(2) a heavy chain variable region containing the amino acid sequence set forth in SEQ ID NO: 85,
(3) a heavy chain variable region containing the amino acid sequence set forth in SEQ ID NO: 86,
(4) a heavy chain variable region containing the amino acid sequence set forth in SEQ ID NO: 87,
(5) a heavy chain variable region containing the amino acid sequence set forth in SEQ ID NO: 88,
(6) a heavy chain variable region containing the amino acid sequence set forth in SEQ ID NO: 89, and Among the antibodies described above, preferred is the antibody having a light chain variable region containing the amino acid sequence set forth in SEQ ID NO: 205 and a heavy chain variable region containing the amino acid sequence set forth in SEQ ID NO: 90.
(XI) An antibody, in which one or more amino acids have been replaced, deleted, added and/or inserted in the amino acid sequence described in any one of the above-mentioned (I) to
(X), and which has an activity equivalent to that of the antibody described in any of (I) to (X).

In the present invention, the activity equivalent to that of the antibody described in any of (I) to (X) means that the binding activity to a human glypican 3 antibody or the cytotoxicity activity on a cell that expresses human glypican 3 (e.g., HepG2 or a recombinant CHO cells expressing human glypican 3, etc.) is equivalent.

Humanized Antibody

One preferred embodiment of the antibody according to the present invention is a humanized antibody that binds to glypican 3. The humanized antibody can be prepared by using a known method.

The humanized antibody is also referred to as a reshaped human antibody, which is made by transplanting the complementarity determining region (CDR) of an antibody of a non-human mammal, for example a mouse antibody, into the CDR of a human antibody. The general recombinant DNA technology for preparation of such antibodies is also known (see European Patent Application EP 125023 and International Patent Application WO 96/02576).

Specifically, for example, in the case where a CDR is derived from a mouse antibody, a DNA sequence which has been designed to link the CDRs of the mouse antibody with the framework region (FR) of a human antibody is synthesized by the PCR method using several oligonucleotides as primers, which have been prepared so as to have portions overlapping with one another at both ends of the CDR and the FR (see the method described in International Patent Application WO 98/13388).

As for the framework region of a human antibody to be linked with the CDR, the one which allows a complementarity determining region to form a favorable antigen-binding site is selected. If necessary, an amino acid in the framework region of a variable region of the antibody may be replaced so that the complementarity determining region of a reshaped human antibody may form an appropriate antigen-binding site (Sato, K. et al., Cancer Res. (1993) 53, 851-856).

The C region of a human antibody may be used as the C region of a chimeric antibody or a humanized antibody, for example, Cγ1, Cγ2, Cγ3, and Cγ4 may be used in the H chain, and Cκ and Cλ may be used in the L chain. The C region of a human antibody may also be modified in order to improve the stability of the antibody or the production thereof. The human antibody to be used in the humanization may be any isotype of human antibody, for example, IgG, IgM, IgA, IgE and IgD, preferably, IgG, more preferably IgG1 or IgG3, and particularly preferably IgG1. the present invention IgG1 is effective when an antibody is used as an anticancer agent in terms of having a high cytotoxicity activity (Chemical immunology, 65: 88 (1997)).

In addition, after the humanized antibody is prepared, an amino acid in a variable region (e.g., FR) or a constant region may be replaced with another amino acid.

The origin of the CDR in a humanized antibody is not particularly limited, and the CDR may be derived from any animals. For example, it is possible to use a sequence derived from a mouse antibody, a rat antibody, a rabbit antibody, a camel antibody or the like. Preferred is a CDR sequence of a mouse antibody.

With regard to the humanization of an antibody, it is generally difficult to humanize it while maintaining the agonist activity of the original antibody. In the present invention, however, a humanized antibody having an agonist activity equivalent to that of the original mouse antibody was successful acquired. Since the antigenicity of the humanized antibody in the human body is reduced, it is useful in administering it into the human for a therapeutic purpose.

Preferred examples of the humanized anti-glypican 3 antibody in the present invention include, for example, an antibody having a heavy chain variable region set forth in SEQ ID NO: 84 (GC33 VH ver.a), SEQ ID NO: 85 (GC33 VH ver.c), SEQ ID NO: 86 (GC33 VH ver.f), SEQ ID NO: 87 (GC33 VH ver.h), SEQ ID NO: 88 (GC33 VH ver.i), SEQ ID NO: 89 (GC33 VH ver.j) or SEQ ID NO: 90 (GC33 VH ver.k) or an antibody having a light chain variable region set forth in SEQ ID NO: 92 (GC33 VL ver.a). Particularly preferred examples thereof include an antibody having a heavy chain variable region set forth in SEQ ID NO: 84 (GC33 VH ver.a), SEQ ID NO: 85 (GC33 VH ver.c), SEQ ID NO: 86 (GC33 VH ver.f), SEQ ID NO: 87 (GC33 VH ver.h), SEQ ID NO: 88 (GC33 VH ver.i), SEQ ID NO: 89 (GC33 VH ver.j) or SEQ ID NO: 90 (GC33 VH ver.k) and a light chain variable region set forth in SEQ ID NO: 92 (GC33 VL ver.a).

In addition, a preferred example of the humanized anti-glypican 3 antibody includes an antibody having a heavy chain variable region containing the amino acid sequence set forth in SEQ ID NO: 90 and a light chain variable region containing the amino acid sequence set forth in SEQ ID NO: 205.

A preferred embodiment of the antibody according to the present invention is an antibody that binds to the epitope to which the antibody set forth in any of the following (1) to (8) binds:
(1) an antibody containing a heavy chain variable region having the amino acid sequence set forth in SEQ ID NO: 62 and a light chain variable region having the amino acid sequence set forth in SEQ ID NO: 73 (GC33),
(2) an antibody containing a heavy chain variable region having the amino acid sequence set forth in SEQ ID NO: 26 and a light chain variable region the amino acid sequence set forth in SEQ ID NO: 48 (M11F1), (3) an antibody containing a heavy chain variable region having the amino acid sequence set forth in SEQ ID NO: 25 and a light chain variable region the amino acid sequence set forth in SEQ ID NO: 47 (M3B8),
(4) an antibody containing a heavy chain variable region having the amino acid sequence set forth in SEQ ID NO: 60 and a light chain variable region the amino acid sequence set forth in SEQ ID NO: 71 (GC199),
(5) an antibody containing a heavy chain variable region having the amino acid sequence set forth in SEQ ID NO: 61 and a light chain variable region the amino acid sequence set forth in SEQ ID NO: 72 (GC202),
(6) an antibody containing a heavy chain variable region having the amino acid sequence set forth in SEQ ID NO: 63 and a light chain variable region the amino acid sequence set forth in SEQ ID NO: 74 (GC179),
(7) an antibody containing a heavy chain variable region having the amino acid sequence set forth in SEQ ID NO: 64 and a light chain variable region the amino acid sequence set forth in SEQ ID NO: 75 (GC194 (1)), and
(8) an antibody containing a heavy chain variable region having the amino acid sequence set forth in SEQ ID NO: 64 and a light chain variable region the amino acid sequence set forth in SEQ ID NO: 76 (GC194 (2)). More preferred is an antibody that binds to the epitope to which the antibody described in any of (1) to (5) binds, and particularly preferred is an antibody that binds to the epitope to which the antibody described in (1) binds.

The antibody that binds to the epitope to which any of the above-mentioned antibodies bind is useful because it has a particularly high cytotoxicity.

The antibody described in any of (1) to (7) binds to a region from the 524th amino acid to the 580th amino acid of human glypican 3. In particular, it binds to a region from the 524th amino acid to the 563rd amino acid. The antibody described in any of (1) to (5) binds to a region from the 537th amino acid to the 563rd amino acid of human glypican 3. The antibody described in (1) binds to a region from the 544th amino acid to the 553rd amino acid of human glypican 3. In particular, it binds to a region from the 546th amino acid to the 551st amino acid.

The antibodies recognizing the above-mentioned epitopes have a high cytotoxicity, therefore they are useful in the treatment of a disease such as cancer. In particular, the antibody which binds to a region from the 546th amino acid to the 551st amino acid is useful as it has a particularly high cytotoxicity.

Accordingly, the present invention includes the antibodies which binds to an epitope in a region from the 524th amino acid to the 580th amino acid of human glypican 3, preferably a region from the 524th amino acid to the 563rd amino acid, more preferably a region from the 537th amino acid to the 563rd amino acid, further more preferably a region from the 544th amino acid to the 553rd amino acid, particularly preferably a region from the 546th amino acid to the 551st amino acid.

Another preferred embodiment according to the present invention is an antibody that recognizes a region from the 524th amino acid to the 563rd amino acid of human glypican 3 and does not recognize a region from the 537th amino acid to the 563rd amino acid.

A further preferred embodiment according to the present invention is an antibody that recognizes a region from the 537th amino acid to the 563rd amino acid of human glypican 3 and does not recognize a region from the 550th amino acid to the 563rd amino acid.

The analysis of an epitope recognized by an antibody can be carried out by a method known to those skilled in the art, for example, by Western blotting described in Examples below.

The antibody that recognizes the above-mentioned regions as an epitope can be obtained by a method known to those skilled in the art. For example, it can be obtained by preparing a peptide containing an amino acid sequence of a target region based on an amino acid sequence of human glypican 3 and preparing an antibody with the use of the peptide as an immunogene, or by preparing an antibody by a usual method and determining an epitope that the obtained antibody recognizes, and then selecting an antibody that recognizes the target epitope.

A preferred example of the anti-glypican 3 antibody of the present invention is an antibody having a high ADCC activity or an antibody having a high CDC activity to a cell that expresses glypican 3.

The phrase "a high ADCC activity" or "a high CDC activity" as used herein means that the antibody of the invention has a higher ADCC activity or a higher CDC activity than that of a known anti-glypican 3 antibody. Known glypican 3 antibodies include, for example, M3C11 and M1E07 described in International Patent Application WO 2004/22739.

The ADCC activity or the CDC activity can be measured by a method known to those skilled in the art. For example, it can be measured by the chromium release test. Specific conditions of the chromium release test for measuring the ADCC activity are not particularly limited, however, for example, it can be measured using the conditions described in the Examples below.

Examples of the cells that express glypican 3 include, for example, a hepatoma cell line such as HepG2, a CHO cell line having a gene encoding glypican 3 incorporated therein and the like. To measure the ADCC activity, it is preferred to use a HepG2 cell line, and to measure the CDC activity, it is preferred to use a recombinant CHO cell line that expresses GPC3. The recombinant CHO cell line that expresses GPC3 may be prepared by any method, however, it can be prepared by, for example, the method described in the Examples below.

In the case where the anti-glypican 3 antibody is used as an anticancer agent, it is preferred that it has an ADCC activity at the same level as that of an antibody containing a heavy chain variable region having the amino acid sequence set forth in SEQ ID NO: 62 and a light chain variable region having the amino acid sequence set forth in SEQ ID NO:73 (GC33). In the case where the anti-glypican 3 antibody is used as an anticancer agent, it is preferred that it has a CDC activity at the same level as that of an antibody containing a heavy chain variable region having the amino acid sequence set forth in SEQ ID NO: 62 and a light chain variable region having the amino acid sequence set forth in SEQ ID NO: 73 (GC33).

Further, the present invention includes an antibody having a high binding activity to glypican 3.

In the present invention, the binding activity of the antibody to glypican 3 can be measured by using a method known to those skilled in the art. For example, it can be measured by utilizing the surface plasmon resonance with BIAcore. Specifically, a glypican 3 protein is immobilized on a sensor chip to react with an antibody, and the interaction between the antibody and glypican 3 can be calculated as a reaction rate constant from the measurement value. In addition, with regard to the evaluation of the binding activity, an enzyme linked immunosorbent assay (ELISA), an enzyme immunoassay (EIA), a radioimmunoassay (RIA) or a fluorescent antibody technique can be used. For example, in the case where an enzyme immunoassay is used, a sample containing an antibody to be tested, for example, a culture supernatant of a cell producing an antibody to be tested or a purified antibody is added to a plate which has been coated with an antigen to which the antibody to be tested binds. Then, a secondary antibody labeled with an enzyme such as alkaline phosphatase is added, and the plated is incubated and washed. Then, an enzyme substrate such as p-nitrophenyl phosphate is added and the absorbance is measured, whereby an antigen binding activity can be evaluated. The upper limit of the binding activity is not particularly limited. However, for example, the upper limit can be defined within the range which is technically possible by those skilled in the art. It will be appreciated that the range which is technically possible will be expanded by the advancement of technology.

Further, in the present invention, an amino acid to be deamidated or an amino acid adjacent to an amino acid to be deamidated may be replaced with another amino acid for the purpose of, for example, suppressing deamidation to increase the stability of the antibody. The amino acid to be deamidated includes, asparagine and glutamine, preferably asparagine. An amino acid adjacent to asparagine is not particularly limited and may be any amino acid. It is known that an asparagine-glycine sequence is particularly susceptible to deamidation, thus, glycine is preferred as the amino acid adjacent to asparagine. An amino acid used for replacement is not particularly limited and may be any amino acid other than asparagine and glutamine. Preferred is an amino acid other than valine and proline. Therefore, in the present invention, in the case where the antibody is deamidated, it is preferred to replace the amino acid with an amino acid other than asparagine, glutamine, valine and proline. Suppression of deamidation by amino acid replacement can be carried out with reference to, for example, International Patent Application WO 03/057881. In the case where amino acid replacement is carried out for the purpose of suppression of deamidation, it is preferred that the antigen binding activity before replacement is maintained.

Another embodiment of stabilization of the antibody includes replacement of glutamic acid with another amino acid. In addition, in the present invention, it was found that, in the case where the 6th amino acid of the heavy chain of an antibody is glutamic acid, the antibody can be significantly stabilized by replacing the glutamic acid with glutamine. Accordingly, the present invention also relates to a method of stabilizing an antibody by replacing the glutamic acid at the 6th position of the heavy chain of the antibody with glutamine. The amino acid numbering of the antibody is known to those skilled in the art (e.g., Kabat, E. A. et al., "Sequences of Proteins of Immunological Interest", US Dept. Health and Human Services 1983).

The antibody of the invention may be a conjugated antibody in which the antibody is conjugated with various molecules, such as polyethyleneglycol (PEG), radioactive materials and toxin. Such a conjugated antibody may be prepared by chemically modifying the antibody obtained as above. Methods for modifying antibodies have already been established in the art. The antibody of the invention encompasses such a conjugated antibody.

The antibody of the invention may also be a bispecific antibody (see, for example, Journal of Immunology, 1994, 152, 5368-5374). The bispecific antibody may recognize glypican 3 and another antigen, or may recognize different epitopes on a GPC3 molecule.

Further, the antibody of the invention may carry a certain protein fused to the N- or C-terminus of the antibody (Clinical Cancer Research, 2004, 10, 1274-1281). The protein to be fused to the antibody may be conveniently selected by those skilled in the art.

In addition, the antibody of the invention includes an antibody with an enhanced cytotoxicity. Examples of the antibody with an enhanced cytotoxicity include an antibody lacking fucose, an antibody having bisecting N-acetyl glucosamine (GlcNAc) attached to its sugar chain, and an antibody having altered binding activity for Fcγ receptor obtained by substituting one or more amino acids in the Fc region. Such antibodies with an enhanced cytotoxicity can be prepared by a method known in the art.

Method of Preparing Antibody

The antibody that binds to glypican 3 can be prepared by a method known to those skilled in the art. For example, a monoclonal antibody-producing hybridoma can be prepared as follows basically using a known technique. That is, the hybridoma can be prepared by immunizing a mammal in accordance with a usual immunization method using a glypican 3 protein or a cell that expresses glypican 3 as a sensitizing antigen. The thus obtained immunocyte is fused with a known parent cell by a usual cell fusion method, and then selecting a monoclonal antibody-producing cell by a usual screening method.

Specifically, a monoclonal antibody can be prepared as follows. First, a glypican 3 protein is obtained based on the glypican 3 gene/amino acid sequence shown in SEQ ID NOs: 3 and 4, which is used as a sensitizing antigen to obtain an antibody. More specifically, the gene sequence encoding glypican 3 is inserted into a known expression vector system, and an appropriate host cell is transformed with the vector, and then a target human glypican 3 protein is purified by a known method from the host cell or the culture supernatant.

Subsequently, this purified glypican 3 protein is used as a sensitizing antigen. Alternatively, a partial peptide of glypican 3 can be used as a sensitizing antigen. In this case, the partial peptide can also be obtained by chemical synthesis according to the amino acid sequence of human glypican 3.

The epitope on a glypican 3 molecule which is recognized by the anti-glypican 3 antibody of the present invention is not limited to a particular epitope. The anti-glypican 3 antibody may recognize any epitope, as long as the epitope is present on a glypican 3 molecule. Accordingly, any fragment can also be used as an antigen for producing the anti-glypican 3 antibody of the present invention, as long as it contains an epitope that is present on a glypican 3 molecule.

A mammal to be immunized with a sensitizing antigen is not particularly limited, but it is preferably selected in view of compatibility with a parent cell to be used for cell fusion. For example, rodents such as mice, rats and hamsters, rabbits or monkeys are generally used.

Immunization of an animal with a sensitizing antigen is carried out in accordance with a known method. For example, immunization is carried out by a general method in which a mammal is injected intraperitoneally or subcutaneously with a sensitizing antigen. Specifically, a sensitizing antigen is diluted with or suspended in an appropriate amount of PBS (Phosphate-Buffered Saline), physiological saline or the like, an appropriate amount of a standard adjuvant such as a Freund's complete adjuvant is mixed with the product if necessary, and then the solution is emulsified and is administered to a mammal several times every 4 to 21 days. In addition, an appropriate carrier can also be used upon immunization with a sensitizing antigen.

A mammal is immunized as described above, and then an increased level of a target antibody in the serum is confirmed.

Subsequently, immunocytes are collected from the mammal, and then subjected to cell fusion. A particularly preferred immunocyte is a splenocyte.

As a parent partner cell to be fused with the above-mentioned immunocyte, a mammalian myeloma cell is used. Examples of a cell line of the myeloma cell that is preferably used herein include various known cell lines such as P3 (P3x63Ag8.653) (J. Immnol. (1979) 123, 1548-1550), P3x63 Ag8U.1 (Current Topics in Microbiology and Immunology (1978) 81, 1-7), NS-1 (Kohler. G. and Milstein, C. Eur. J. Immunol. (1976) 6, 511-519), MPC-11 (Margulies. D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), S194 (Trowbridge, I. S. J. Exp. Med. (1978) 148, 313-323) and R210 (Galfre, G. et al., Nature (1979) 277, 131-133).

Cell fusion of the above-mentioned immunocytes with myeloma cells can be basically carried out in accordance with a known method, for example, the method of Kohler and Milstein et al. (Kohler. G. and Milstein, C., Methods Enzymol. (1981) 73, 3-46).

More specifically, the above-mentioned cell fusion is carried out in a normal nutrition culture solution in the presence of, for example, a cell-fusion accelerator. As the cell-fusion accelerator, for example, polyethylene glycol (PEG), a hemagglutinating virus of Japan (HVJ) is used. If desired, an adjuvant such as dimethylsulfoxide can be added to further enhance the fusion efficiency.

The ratio of immunocytes to myeloma cells may be appropriately selected. For example, it is preferred that the number of immunocytes is 1 to 10 times greater than that of myeloma cells. The culture solution to be used for the above-mentioned cell fusion include, for example, a RPMI1640 culture solution or a MEM culture solution which is suitable for the growth of the above-mentioned myeloma cell line, or another normal culture solution which is used for this type of cell culture. Moreover, a serum supplement such as fetal calf serum (FCS) can be used in combination therewith.

Cell fusion is carried out as follows. Predetermined amounts of the above-mentioned immunocytes and myeloma cells are mixed well in the above-mentioned culture solution, a PEG (e.g., with an average molecular weight of approximately 1000 to 6000) solution (a general concentration of 30 to 60% (w/v)), which had been pre-heated at approximately 37° C., is added, and then the solution is mixed, whereby a target fusion cell (hybridoma) is formed. Subsequently, an appropriate culture solution is added successively, and then a step of removing the supernatant by centrifugation is repeated to remove a reagent for cell fusion or the like that is unfavorable for the growth of the hybridoma.

The thus obtained hybridoma is selected by culturing the hybridoma in a standard selective culture solution such as a HAT culture solution (a culture solution containing hypoxanthine, aminopterin and thymidine). Cultivation in the above-mentioned HAT culture solution is continued for a time period sufficient for the cells (unfused cells) other than the target hybridoma to die (normally, several days to several weeks). Subsequently, a standard limiting dilution method is conducted to screen for and monoclone of hybridoma that produces a target antibody.

In addition to the method of immunizing a non-human animal with an antigen to obtain hybridoma, a desired human antibody having a binding activity to glypican 3 can also be obtained by sensitizing a human lymphocyte with glypican 3 in vitro, and allowing the sensitized lymphocyte to fuse with a human-derived myeloma cell having a permanent division potential (see JP-B-1-59878). In another method, glypican 3 antigen is administered to a transgenic animal having all the repertories of human antibody genes to obtain anti-glypican 3 antibody-producing cells, which are then immortalized, and a human antibody for glypican 3 may be obtained from the immortalized anti-glypican 3 antibody-producing cells (see International Patent Applications WO 94/25585, WO 93/12227, WO 92/03918 and WO 94/02602).

The thus prepared hybridoma that produce a monoclonal antibody can be passage-cultured in a standard culture solution, or can be stored for a long period in liquid nitrogen.

One example of a method employed to obtain a monoclonal antibody from the hybridoma involves culturing the hybridoma and obtaining a monoclonal antibody from the culture supernatant in accordance with a standard method. Another method involves administering the hybridoma to a mammal that is compatible with the hybridoma to allow it to proliferate, and obtaining a monoclonal antibody from the ascites. The former method is suitable to obtain an antibody of high purity, while the latter method is suitable for the mass production of antibodies.

It is also possible to prepare a recombinant antibody by cloning the antibody gene from the hybridoma, incorporating the gene into an appropriate vector, introducing the vector into a host, and then allowing the host to produce the recombinant antibody by a genetic engineering technique (e.g., see Vandamme, A. M. et al., Eur. J. Biochem. (1990) 192, 767-775, 1990).

Specifically, mRNA encoding the variable (V) region of an anti-glypican 3 antibody is isolated from a hybridoma producing the anti-glypican 3 antibody. mRNA is isolated by a known method such as a guanidine ultracentrifugal method (Chirgwin, J. M. et al., Biochemistry (1979) 18, 5294-5299) or an AGPC method (Chomczynski, P. et al., Anal. Biochem. (1987) 162, 156-159), and total RNA is prepared, and then target mRNA is prepared using an mRNA Purification Kit (Pharmacia) or the like. In addition, mRNA can also be directly prepared using a QuickPrep mRNA Purification Kit (Pharmacia).

The cDNA of the antibody V region is synthesized using a reverse transcriptase from the thus obtained mRNA. cDNA may be synthesized using an AMV Reverse Transcriptase First-strand cDNA Synthesis Kit (SEIKAGAKU CORPORATION) or the like. In addition, for example, a 5'-Ampli FINDER RACE Kit (Clontech), the 5'-RACE method using PCR (Frohman, M. A. et al., Proc. Natl. Acad. Sci. USA (1988) 85, 8998-9002, Belyavsky, A. et al., Nucleic Acids Res. (1989) 17, 2919-2932) can be employed for synthesizing and amplifying cDNA.

A target DNA fragment is purified from the thus obtained PCR product, and then ligated to a vector DNA. A recombinant vector is prepared from the product, and then the vector is introduced into *E. coli* or the like, and a colony is selected, thereby preparing a desired recombinant vector. The nucleotide sequence of the target DNA is then determined by a known method such as a dideoxynucleotide chain termination method.

After DNA encoding the V region of the target anti-glypican 3 antibody is obtained, this DNA is incorporated into an expression vector containing DNA encoding the constant region (C region) of the target antibody.

To produce the anti-glypican 3 antibody used in the present invention, the antibody gene is incorporated into an expression vector so that the gene is expressed under the regulation of the gene expression control region including, for example, an enhancer and a promoter. Next, a host cell is transformed with the expression vector, thereby allowing the host to express the antibody.

An antibody gene can be expressed by incorporating a polynucleotide encoding the H chain or a polynucleotide encoding the L chain separately into an expression vector, and then simultaneously transforming a host cell with the vectors, or by incorporating polynucleotides encoding the H chain and the L chain into a single expression vector, and then transforming a host cell with the vector (see International Patent Application WO 94/11523).

Polynucleotide

In another aspect, the present invention provides a polynucleotide encoding a heavy chain variable region or a light chain variable region of the antibody of the present invention. Preferably, the polynucleotide of the present invention has a nucleotide sequence described in any of SEQ ID NOs: 11-21, 33-43, 55-59, 65-70 and 77-83. In addition, a polynucleotide that is hybridized to the above-mentioned polynucleotide under stringent conditions and encodes an antibody having an activity equivalent to that of the antibody of the present invention is also within the scope of the present invention.

The polynucleotide of the present invention is not particularly limited as long as it encodes the antibody of the present invention. It is a polymer composed of a plurality of nucleotides, such as deoxyribonucleic acids (DNA) or ribonucleic acids (RNA). It may contain a base other than a naturally occurring base. The polynucleotide of the present invention can be used for producing an antibody by a genetic engineering technique. In addition, the polynucleotide of the present invention can be used as a probe to screen for an antibody having a function equivalent to that of the antibody of the present invention. That is, a polynucleotide encoding the antibody of the present invention or a partial fragment thereof may be used as a probe to obtain DNA that is hybridized to the polynucleotide under stringent conditions and encodes an antibody having an activity equivalent to that of the antibody of the present invention by techniques such as a hybridization technique, a gene amplification technique (e.g., PCR). Such DNA is also included in the polynucleotide of the present invention.

The hybridization technique (Sambrook, J. et al., Molecular Cloning 2nd ed., 9.47-9.58, Cold Spring Harbor Lab. Press, 1989) is well known to those skilled in the art. Examples of the hybridization conditions include, for example, low stringent conditions. The low stringent conditions are, for example, the conditions of 42° C., 0.1×SSC and 0.1% SDS, preferably the conditions of 50° C., 0.1×SSC and 0.1% SDS when washing is performed after hybridization. More preferred examples of the hybridization conditions include, for example, high stringent conditions. The high stringent conditions are, for example, the conditions of 65° C., 5×SSC and 0.1% SDS. Under these conditions, it can be expected that a polynucleotide having a higher homology can be efficiently obtained under higher temperature. Incidentally, there are plural factors that affect the stringency of hybridization, such as temperature and the concentration of salt, and those skilled in the art can achieve a similar stringency by appropriately selecting these factors.

An antibody functionally equivalent to the antibody of the present invention encoded by a polynucleotide obtained by such a hybridization technique and a gene amplification technique usually has a high homology with the antibody in terms of the amino acid sequence. The antibody of the present invention also includes an antibody that is functionally equivalent to the antibody of the present invention and has a high homology with the amino acid sequence of the antibody. A high homology means generally at least 50% or higher identity, preferably 75% or higher identity, more preferably 85% or higher identity, and further more preferably 95% or higher identity at the amino acid level. To determine the homology of polypeptides, the algorithm described in the literature (Wilbur, W. J. and Lipman, D. J., Proc. Natl. Acad. Sci. USA (1983) 80, 726-730) may be employed.

The present invention also provides a vector containing the polynucleotide of the present invention. Such a vector can be used for preparing the antibody of the present invention. As for the vector of the present invention, in the case where E. coli is used as a host, for example, it is not particularly limited as long as it has "ori" for use in amplification in E. coli to produce and amplify the vector in a large amount in E. coli (e.g., JM109, DH5α, HB101 or XL1Blue), and has a marker gene for selecting a transformed E. coli (e.g., a drug resistance gene that can be identified by a drug such as ampicillin, tetracycline, kanamycin or chloramphenicol). Examples of the vector include M13-series vectors, pUC-series vectors, pBR322, pBluescript, pCR-Script and the like. In addition, pGEM-T, pDIRECT, and pT7 can also be used for subcloning and extracting cDNA as well as the vectors described above.

As the vector of the present invention, an expression vector is particularly useful. For example, an expression vector to be expressed in E. coli should have the above characteristics to be amplified in E. coli. In addition, in the case where E. coli, such as JM109, DH5α, HB101, or XL1-Blue is used as a host cell, it is indispensable that the vector should have a promoter, for example, lacZ promoter (Ward et al., Nature (1989) 341, 544-546; FASEB J. (1992) 6, 2422-2427), araB promoter (Better et al., Science (1988) 240, 1041-1043) T7 promoter or the like, that can efficiently express the desired product in E. coli. Examples of such a vector include pGEX-5X-1 (Pharmacia), "QIAexpress system" (Qiagen), pEGFP, pET (in this case, the host is preferably BL21 which expresses T7 RNA polymerase) and the like, as well as the vectors described above.

In addition, the vector may also contain a signal sequence for polypeptide secretion. As for the signal sequence for protein secretion, in the case where a polypeptide is produced in the periplasm of E. coli, the pelB signal sequence (Lei S. P. et al., J. Bacteriol (1987) 169, 4379) can be used. Introduction of the vector into a host cell can be carried out by using, for example, the calcium chloride method and the electroporation method.

In addition to E. coli, for example, expression vectors derived from mammals (e.g., pcDNA3 (Invitrogen) and pEGF-BOS (Nucleic Acids Res. (1990) 18(17), p 5322), pEF and pCDM8), expression vectors derived from insect cells (e.g., "Bac-to-BAC baculovirus expression system" (GIBCO BRL) and pBacPAK8), expression vectors derived from plants (e.g., pMH1 and pMH2), expression vectors derived from animal viruses (e.g., pHSV, pMV and pAdexLcw), expression vectors derived from retroviruses (e.g., pZIPneo), expression vectors derived from yeast (e.g., "Pichia Expression Kit" (Invitrogen), pNV11 and SP-Q01), and expression vectors derived from *Bacillus subtilis* (e.g., pPL608 and pKTH50) can be used as the vector of the present invention.

For the purpose of expressing the vector in an animal cell such as a CHO cell, a COS cell, an NIH3T3 cell or the like, it is indispensable for the vector to have a promoter required for expression in a cell such as SV40 promoter (Mulligan et al., Nature (1979) 277, 108), MMTV-LTR promoter, EF1α promoter (Mizushima et al., Nucleic Acids Res. (1990) 18, 5322), CMV promoter or the like, and more preferably to have a marker gene (such as a drug resistance gene that can be identified by a drug such as neomycin or G418) for selecting transformation into the cell. Examples of the vector having such characteristics include, for example, pMAM, pDR2, pBK-RSV, pBK-CMV, pOPRSV and pOP13.

Further, for the purpose of stably expressing a gene and, at the same time, amplifying the gene copy numbers in the cell, a vector (e.g., pCHOI, etc.) having the DHFR gene is introduced into the CHO cell deficient in the nucleic acid synthetic pathway to complement the deficiency and is amplified with methotrexate (MTX). In addition, for the purpose of transient expression of a gene, transformation is effected with a vector (such as pcD) having the origin of replication for SV40 using a COS cell having on the chromosome a gene that expresses the SV40 T antigen. As the origin of replication, the one derived from a polyoma virus, an adenovirus, a bovine papilloma virus (BPV) and the like can also be used. Further, for the amplification of gene copy numbers in the host cell system, the expression vector can include, as a selectable marker, the aminoglycoside transferase (APH) gene, the thymidine kinase (TK) gene, *E. coli* xanthine guaninephosphoribosyl transferase (Ecogpt) gene, the dihydrofolate reductase (dhfr) gene and the like.

To prepare the antibody of the present invention, the vector is introduced into a host cell. The host cell into which the vector is introduced is not particularly limited, but includes, for example, *E. coli* or any of various animal cells. For example, the host cell can be used as a production system for the production or expression of the antibody of the present invention. As for the production system of polypeptide preparation, there are an in vitro production system and an in vivo production system. In vitro production system include a production system which employs eukaryotic cells and a production system which employs prokaryotic cells.

In the case where the eukaryotic cell is used, for example, an animal cell, a plant cell or a fungal cell can be used. Known animal cells include a mammalian cell such as a CHO cell (J. Exp. Med. (1995) 108, 945), a COS cell, a 3T3 cell, a myeloma cell, a baby hamster kidney (BHK) cell, a HeLa cell and a Vero cell, an amphibian cell such as a *Xenopus oocyte* (Valle, et al., Nature (1981) 291, 358-340), or an insect cell such as Sf9, Sf21, and Tn5. In the present invention, CHO-DG44, CHO-DXB11, a COS7 cell, a BHK cell are preferably used. Among the animal cells, for the purpose of performing a large amount of expression, a CHO cell is particularly preferred. Introduction of the vector into the host cell can be carried out by, for example, the calcium phosphate method, the DEAE-dextran method, the cationic ribozome DOTAP (Boehringer Mannheim), the electroporation method, the lipofection method or the like.

As for the plant cell, for example, a cell derived from *Nicotiana tabacum* is known as a protein production system, which may be subjected to call us culture. Examples of the fungal cells include yeast such as the genus *Saccharomyces*, more specifically *Saccharomyces cerevistae* and *Saccharomyces pombe*, and filamentous fungi such as the genus *Aspergillus*, more specifically *Aspergillus niger*.

In the case where the prokaryotic cell is used, production system using a bacterial cell may be employed. Examples of the bacterial cells include *Escherichia coli* (*E. coli*) such as JM109, DH5α and HB101, and *Bacillus subtilis*.
Preparation of Recombinant Antibody The antibody of the present invention can be prepared by culturing the above-mentioned host cells. The antibody can be obtained by culturing in vitro a cell transformed with a desired polynucleotide. Cultivation can be carried out in accordance with a known method. Culture media for animal cells include, for example, DMEM, MEM, RPMI 1640, and IMDM. A serum supplement such as FBS or fetal calf serum (FCS) may be used in combination, or serum-free medium can be used. The pH during the cultivation is preferably about 6 to 8. Cultivation is usually carried out at about 30 to 40° C. for about 15 to 200 hours with, as needed, medium change, aeration, and agitation.

On the other hand, systems for producing a polypeptide in vivo include, for example, a production system which employs an animal and a production system which employs a plant. The target polynucleotide is introduced into such an animal or a plant, and the polypeptide is produced in the body of the animal or the plant and recovered. The term "host cell" as used herein encompasses such an animal and a plant.

When the animal is used, production systems employing a mammal or an insect are available. As the mammal, goats, pigs, sheep, mice and cattle canbe used (Vicki Glaser, SPECTRUM Biotechnology Applications, 1993). A transgenic animal can also be used as a mammal.

For example, the target polynucleotide is prepared as a fusion gene with a gene encoding a polypeptide which is inherently produced in the milk such as goat β casein. Then, the DNA fragment containing this fusion gene is injected into a goat embryo, and the embryo is transplanted into a female goat. The target antibody can be obtained from the milk produced by the transgenic goat borne to the goat which received the embryo or the offspring thereof. To increase the amount of milk containing the antibody produced by the transgenic goat, hormone may be given to the transgenic goat as needed. (Ebert, K. M. et al., Bio/Technology (1994) 12, 699-702).

In addition, as an insect, for example, a silkworm can be used. In the case where a silkworm is used, a silkworm is infected with a baculovirus into which the polynucleotide encoding the target antibody has been inserted. The target antibody can be obtained from the body fluid of the silkworm (Susumu, M. et al., Nature (1985) 315, 592-594).

In the case where a plant is used, for example, tobacco can be used. In the case where tobacco is used, a polynucleotide encoding the target antibody is inserted into an expression vector for a plant, for example pMON 530, and then the vector is introduced into a bacterium such as *Agrobacterium tumefaciens*. Then, tobacco such as *Nicotiana tabacum* is infected with the bacterium, whereby the target antibody can be obtained from the leaves of the tobacco (Julian, K.-C. Ma et al., Eur. J. Immunol. (1994) 24, 131-138).

The thus obtained antibody can be isolated from the inside or the outside (culture medium, etc.) of the host cell and then can be purified to a substantially pure and uniform antibody. Separation and purification of the antibody may be carried out by a separation and a purification method usually used in purification of polypeptides. For example, polypeptides can be separated and purified by any methods including chromatography columns, filtration, ultrafiltration, salting-out, solvent precipitation, solvent extraction, distillation, immunoprecipitation, SDS-polyacrylamide gel electrophoresis, isoelectric focusing, dialysis, recrystallization, and a combination thereof.

Examples of the chromatography include, for example, affinity chromatography, ion exchange chromatography, hydrophobic chromatography, gel-filtration, reverse phase chromatography, adsorption chromatography (Strategies for Protein Purification and Characterization: A Laboratory Course Manual. Ed Daniel R. Marshak et al., Cold Spring Harbor Laboratory Press, 1996). These chromatographies can be carried out using a liquid phase chromatography such as HPLC and FPLC. Examples of a column to be used for affinity chromatography include a protein A column or a protein G column. One example of the protein A column is Hyper D, POROS, Sepharose F. F. (Pharmacia).

Further, before or after purification of the antibody, the antibody can be modified or peptides can be partially removed as needed by allowing a suitable protein-modifying enzyme to act on. The protein-modifying enzyme for this purpose include, for example, trypsin, chymotrypsin, lysyl endopeptidase, protein kinase, glucosidase.

Diagnostic Method

In another aspect, the present invention provides a method of diagnosing a disease such as cancer by detecting GPC3 protein in a test sample with the use of the antibody of the present invention.

The detection used herein includes quantitative detection and non-quantitative detection. The non-quantitative detection include, for example, determination of merely whether or not GPC3 protein is present, determination of whether or not a specific amount or more of GPC3 protein is present, determination for comparison of the amount of GPC3 protein with that of another sample (e.g., a control sample) The quantitative detection includes determination of the concentration of GPC3 protein, determination of the amount of GPC3 protein.

The test sample is not particularly limited as long as it is a sample that may possible contain GPC3 protein, however, preferred is a sample collected from the body of a living organism such as a mammal, and more preferred is a sample collected from human. Specific examples of the test sample may include, for example, blood, interstitial fluid, plasma, extravascular fluid, cerebral fluid, joint fluid, pleural fluid, serum, lymph fluid, saliva, preferably blood, serum and plasma. In addition, a sample obtained from the test sample such as culture solution of cells collected from the body of the living organism is also included in the test sample of the present invention.

The cancer to be diagnosed is not particularly limited, and specific examples may include liver cancer, pancreatic cancer, lung cancer, colon cancer, mammary cancer, prostate cancer, leukemia and lymphoma, preferably liver cancer. GPC3 to be detected is not particularly limited, and may be either full-length GPC3 or a fragment thereof. In the case where a fragment of GPC3 is detected, it may be either the N-terminal fragment or the C-terminal fragment, however, the N-terminal fragment is preferred. In addition, the GPC3 protein may also be a heparan sulfate-added GPC3 or a GPC3 core protein.

The method of detecting GPC3 protein contained in a test sample is not particularly limited, however, detection is preferably performed by an immunological method with the use of an anti-GPC3 antibody. Examples of the immunological method include, for example, a radioimmunoassay, an enzyme immunoassay, a fluorescence immunoassay, a luminescence immunoassay, immunoprecipitation, a turbidimetric immunoassay. Preferred is an enzyme immunoassay, and particularly preferred is an enzyme-linked immunosorbent assay (ELISA) (e.g., a sandwich ELISA). The above-mentioned immunological method such as an ELISA can be carried out by a method known to those skilled in the art.

A general detection method with the use of an anti-GPC3 antibody comprises immobilizing an anti-GPC3 antibody on a support, adding a test sample thereto, incubating the support to allow the anti-GPC3 antibody and GPC3 protein to bind to each other, washing the support, and detecting the GPC3 protein binding to the support via the anti-GPC3 antibody to detect GPC3 protein in a test sample.

The binding between the anti-GPC3 antibody and the GPC3 protein is generally carried out in a buffer. Buffers used in the invention include, for example, a phosphate buffer, a Tris buffer. Incubation is carried out under the conditions generally employed, for example, at 4° C. to room temperature for 1 hour to 24 hours. The washing after incubation can be carried out by any method as long as it does not inhibit the binding between the GPC3 protein and the anti-GPC3 antibody, using for example a buffer containing a surfactant such as Tween 20.

In the method of detecting GPC3 protein of the present invention, a control sample may be provided in addition to a test sample to be tested for GPC3 protein. The control samples include a negative control sample that does not contain GPC3 protein and a positive control sample that contains GPC3 protein. In this case, it is possible to detect GPC3 protein in the test sample by comparing the result obtained with the negative control sample that does not contain GPC3 protein with the result obtained with the positive control sample that contains GPC3 protein. It is also possible to quantitatively detect GPC3 protein contained in the test sample by obtaining the detection results of the control samples and the test sample as numerical values, and comparing these numerical values.

One preferred embodiment of detecting GPC3 protein binding to the support via an anti-GPC3 antibody is a method using an anti-GPC3 antibody labeled with a detectable label. For example, GPC3 protein may be detected by contacting the test sample with an anti-GPC3 antibody immobilized on the support, washing the support, and then detecting GPC3 with the use of the labeled antibody that specifically binds to GPC3 protein.

The labeling of an anti-GPC3 antibody can be carried out by a generally known method. Examples of the detectable label known to those skilled in the art include a fluorescent dye, an enzyme, a coenzyme, a chemiluminescent substance or a radioactive substance. Specific examples may include radioisotopes ($^{32}P$, $^{14}C$, $^{125}I$, $^{3}H$, $^{131}I$ and the like), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin and the like. In the case where biotin is used as a detectable label, it is preferred that a biotin-labeled antibody is added, and then avidin conjugated to an enzyme such as alkaline phosphatase is further added.

Specifically, a solution containing an anti-GPC3 antibody is added to a support such as a plate to allow the anti-GPC3 antibody to be immobilized. After washing, the plate is blocked with, for example, BSA in order to prevent the non-specific binding of a protein. The plate is washed again, and then the test sample is added to the plate. After being incubated, the plate is washed, and then the labeled anti-GPC3 antibody is added. After being incubated appropriately, the plate is washed, and then the labeled anti-GPC3 antibody remaining on the plate is detected. The detection of the protein can be carried out by a method known to those skilled in the art. For example, in the case where the antibody is labeled with a radioactive substance, the protein may be detected by liquid scintillation or the RIA method. In the case where the antibody is labeled with an enzyme, the protein may be detected by adding a substrate and detecting an enzymatic change of the substrate such as color development with an absorbance reader. In the case where the antibody is labeled with a fluorescent substance, the protein may be detected with the use of a fluorometer.

A particularly preferred embodiment of the method of detecting GPC3 protein of the present invention is a method using an anti-GPC3 antibody labeled with biotin and avidin. Specifically, a solution containing an anti-GPC3 antibody is added to a support such as a plate to allow the anti-GPC3 antibody to be immobilized thereon. After washing, the plate is blocked with, for example, BSA in order to prevent the nonspecific binding of a protein, The plate is washed again, and then the test sample is added to the plate. After being incubated, the plate is washed, and then the biotin-labeled anti-GPC3 antibody is added. After being incubated appropriately, the plate is washed, and then avidin conjugated to an enzyme such as alkaline phosphatase or peroxidase is added. After being incubated, the plate is washed, and then a substrate of the enzyme conjugated to avidin is added. Then, GPC3 protein is detected by means of the enzymatic change of the substrate as an indicator.

Another embodiment of the method of detecting GPC3 protein of the present invention is a method using a primary antibody that specifically binds to GPC3 protein and a secondary antibody that specifically binds to the primary antibody. For example, the test sample is brought into contact with an anti-GPC3 antibody immobilized on the support, the support is incubated and washed, and the bound GPC3 protein after washing is detected with a primary anti-GPC3 antibody and a secondary antibody that specifically binds to the primary antibody. In this case, the secondary antibody is preferably labeled with a detectable label.

Specifically, a solution containing an anti-GPC3 antibody is added to a support such as a plate to allow the anti-GPC3 antibody to be immobilized thereon. After washing, the plate is blocked with, for example, BSA in order to prevent the nonspecific binding of a protein. The plate is washed again, and then the test sample is added to the plate. After being incubated, the plate is washed, and then a primary anti-GPC3 antibody is added. After being incubated appropriately, the plate is washed, and then a secondary antibody that specifically binds to the primary antibody is added. After being incubated appropriately, the plate is washed, and then the secondary antibody remaining on the plate is detected. The detection of the secondary antibody can be carried out by the above-mentioned method.

Pharmaceutical Composition

In another aspect, the present invention provides a pharmaceutical composition containing the antibody of the present invention. The pharmaceutical composition containing the antibody of the present invention is useful in the treatment and/or prevention of a disease associated with cell proliferation such as cancer, and particularly it is useful in the treatment and/or prevention of liver cancer. In the case where the antibody of the present invention is used as a pharmaceutical composition, the antibody can be formulated into a dosage form by a method known to those skilled in the art. For example, the pharmaceutical composition can be used parenterally in the form of an injection of a sterile solution or a suspension with water or another pharmaceutically acceptable solution. For example, the antibody can be formulated into a dosage form by appropriately mixing it with a pharmaceutically acceptable carrier or solvent, such as sterile water, physiological saline, a plant-oil, an emulsifier, a suspension, a surfactant, a stabilizer, a flavor, an excipient, a vehicle, a preservative, a binder to prepare a unit dosage form required for generally accepted Drug Implementation. The amount of active ingredients in these preparations is selected to allow for administration of a suitable dosage within the indicated range.

A sterile composition for injection can be formulated by using a vehicle such as distilled water for injection in accordance with the general Drug Implementation.

Examples of the aqueous solution for injection include, for example, physiological saline, glucose, and other isotonic liquids including adjuvants, such as D-sorbitol, D-mannnose, D-mannitol and sodium chloride. They can be used in combination with a suitable solubilizer, such as an alcohol, specifically ethanol, a polyalcohol such as propylene glycol and polyethylene glycol, and a non-ionic surfactant such as Polysorbate 80™ and HCO-50.

Sesame oil or soybean oil can be used as a oleaginous liquid and may be used in combination with benzyl benzoate or benzyl alcohol as a solubilizer. It may be formulated with a buffer such as a phosphate buffer or a sodium acetate buffer, a pain-killer such as procaine hydrochloride, a stabilizer such as benzyl alcohol or phenol, or an antioxidant. The prepared injection is generally filled into a suitable ampule.

The method of administration is preferably parenteral, and specific examples thereof include injection, transnasal administration, transpulmonary administration, transdermal administration and the like. The injection formulation may be administered systemically or topically by intravenous injection, intramuscular injection, intraperitoneal injection, subcutaneous injection or the like.

The method of administration can be appropriately selected according to the age and the symptoms of a patient. For example, one dose of the pharmaceutical composition containing the antibody or the polynucleotide encoding the antibody can be selected from the range of 0.0001 mg to 1,000 mg per kg of body weight. Alternatively, for example, the dose can be selected from the range of 0.001 mg to 100,000 mg/body per patient, although it is not always limited to these numerical values. The dose and the method of administration vary according to the body weight, the age and the symptoms of a patient, and are appropriately selected by those skilled in the art.

All patents and references cited in this specification are incorporated by reference. All the contents disclosed in the specifications and drawings of Japanese Patent Application No. 2004-203637, on which the application claims priority, are incorporated herein by reference.

EXAMPLE

The present invention will be described in more detail with reference to Examples below. However, the present invention is not limited to these Examples.

Example 1 cDNA Cloning of Human Glypican 3 (GPC3)

A full-length cDNA encoding human GPC3 was amplified by PCR reaction with an Advantage 2 kit (CLONTECH) using 1st stranded cDNA prepared by a usual method from a colon cancer cell line, Caco2, as a template. More specifically, 50 µL of a reaction mixture containing 2 µL of cDNA derived from Caco2, 1 µL of a sense primer (GATATC-ATG-GCCGGGACCGTGCGCACCGCGT: SEQ ID NO: 1), 1 µL of an antisense primer (GCTAGC-TCAGTGCACCAGGAA-GAAGAAGCAC: SEQ ID NO: 2), 5 µL of Advantage 2 10× PCR buffer, 8 µL of dNTP mix (1.25 mM) and 1.0 µL of Advantage polymerase Mix was subjected to 35 cycles consisting of 94° C. for 1 minute, 63° C. for 30 seconds and 68° C. for 3 minutes. The amplified product from the PCR reaction was inserted into a TA vector, PGEM-T Easy, using pGEM-T Easy Vector System I (Promega). The sequence was confirmed by using an ABI 3100 DNA sequencer. In this way, a cDNA encoding full-length human GPC3 was isolated. The sequence shown in SEQ ID NO: 3 indicates the nucleotide sequence of human GPC3 gene and the sequence shown in SEQ ID NO: 4 indicates the amino acid sequence of human GPC3 protein.

Example 2

Preparation of Soluble Form of GPC3

As immunoprotein for the generation of an anti-GPC3 antibody, a soluble form of GPC protein was prepared, in which a hydrophobic region at the C-terminal side (564-580 amino acids) was deleted.

By using the full-length human GPC3 cDNA as a template, a PCR reaction was carried out using an antisense primer (ATA GAA TTC CAC CAT GGC CGG GAC CGT GCG C: SEQ ID NO: 5) and a sense primer, to which an EcoRI recognition sequence and a Kozak sequence were added, (ATA GGA TCC CTT CAG CGG GGA ATG AAC GTT C: SEQ ID NO: 6). The obtained PCR fragment (1711 bp) was cloned into pCXND2-Flag. The pCXND2-Flag was designed to express a Flag-tagged protein by inserting the region for DHFR gene expression of pCHOI (Hirata et al., FEBS letter 1994; 356; 244-248) into the HindIII site of pCXN2 (Niwa et al., Gene 1991; 108; 193-199) and adding a Flag tag sequence to the downstream of the multicloning site. The constructed expression plasmid DNA was introduced into a CHO cell line, DXB11, and a CHO cell line highly expressing the soluble form of GPC3 was obtained by selection with 500 μg/mL Geneticin. The large-scale cultivation of the CHO cell line highly expressing the soluble form of GPC3 was carried out using a 1700-cm² roller bottle, and the culture supernatant was recovered for the antibody purification. The culture supernatant was applied to a DEAE sepharose Fast Flow column (Amersham) and, after washing, the antibody was eluted with a buffer containing 500 mM NaCl, and affinity purified using Anti-Flag M2 agarose affinity gel (SIGMA). The elution was carried out with 200 μg/mL FLAG peptide. After the eluate was concentrated with Centriprep-10 (Millipore), FLAG peptide was removed by gel filtration using Superdex 200 HR 10/30 (Amersham). Lastly, the filtrate was concentrated using a DEAE sepharose Fast Flow column and eluted with PBS (containing 500 mM NaCl) without Tween 20 to effect buffer exchange.

Example 3

Preparation of Soluble Form of GPC3 Core Protein

GPC3 is modified by heparan sulfate to become a macromolecule. To eliminate an antibody against heparan sulfate in a screening for an anti-GPC3 antibody, a soluble form of GPC3 core protein that had a point mutation in the heparan sulfate-binding site was prepared and used in the screening.

Using the above-mentioned soluble form of GPC3 (1-563) as a template, a cDNA in which Ser residues at the 495th and 509th positions were replaced with Ala was prepared by the assembly PCR method, in which primers were designed to add His tag to the C-terminus. The obtained cDNA was cloned into pCXND3 vector. The pCXND3 was constructed by inserting the DHFR gene expressing region of pCHOI in the HindIII site of pCXN2. The constructed expression plasmid DNA was introduced into DXB11 cell line and a CHO cell line highly expressing a soluble form of GPC3 core protein was obtained by selection with 500 μg/mL Geneticin.

The large-scale cultivation was carried out using a 1700-cm² roller bottle and the culture supernatant was recovered for antibody purification. The culture supernatant was applied to a Q sepharose Fast Flow column (Amersham). After washing, the antibody was eluted with a phosphate buffer containing 500 mM NaCl, and affinity purified using a Chelating sepharose Fast Flow column (Amersham). The antibody was eluted with a gradient of 10 to 150 mM imidazole. Lastly, the eluate was concentrated using a Q sepharose Fast Flow column and, eluted with a phosphate buffer containing 500 mM NaCl.

SDS polyacrylamide gel electrophoresis under reducing conditions showed three bands of 70 kDa, 40 kDa and 30 kDa. The result of amino acid sequencing using an ABI492 protein sequencer (Applied Biosystems) indicated that the 30 kDa band corresponded to the amino acid sequence of the 359th and its downstream or the 375th and its downstream of GPC3, suggesting that GPC3 was cleaved between Arg358 and Ser359 or between Lys374 and Val375, hence, it was separated into 40 kDa of the N-terminal fragment and 30 kDa of the C-terminal fragment.

Example 4

Preparation of CHO Cell Line Expressing Full-Length Human GPC3

To obtain a cell line for evaluating a binding activity using flow cytometry, a CHO cell line expressing full-length GPC3 was established.

Ten microgram of a full-length human GPC3 gene expression vector and 60 μL of SuperFect (QIAGEN) were mixed. After a complex was formed, gene introduction was carried out by adding it to a CHO cell line, DXB11. After a 24-hour cultivation in a $CO_2$ incubator, selection was started using αMEM (GIBCO BRL) containing Geneticin at a final concentration of 0.5 mg/mL and 10% FBS. The resulting Geneticin-resistant colonies were collected and cell cloning was carried out by the limiting dilution method. Each cell clone was solubilized and the expression of full-length human GPC3 was confirmed by Western blotting using an anti-GPC3 antibody. In this way, a stably expressing cell line was obtained.

Example 5

Evaluation of Binding Activity by ELISA

The soluble form of GPC3 core protein was diluted to 1 μg/mL with a coating buffer (0.1 mol/L $NaHCO_3$ (pH 9.6), 0.02% (w/v) $NaN_3$) and added to an immunoplate and left at 4° C. overnight to coat the plate. After the plate was blocked with a dilution buffer (50 mmol/L Tris-HCl (pH 8.1), 1 mmol/L $MgCl_2$, 150 mmol/L NaCl, 0.05% (v/v) Tween 20, 0.02% (w/v) $NaN_3$, 1% (w/v) BSA), an anti-GPC3 antibody was added and left at room temperature for 1 hour. After washing with a rinse buffer (0.05% (v/v) Tween20, PBS), an anti-mouse IgG antibody (ZYMED) labeled with alkaline phosphatase was added and left at room temperature for 1 hour. After washing with the rinse buffer, SIGMA 104 (SIGMA) diluted to 1 mg/mL with a substrate buffer (50 mmol/L $NaHCO_3$ (pH 9.8), 10 mmol/L $MgCl_2$) was added and left at room temperature for 1 hour for color development. Then the absorbance (at 405 nm, reference wavelength of 655 nm) was measured using a Benchmark Plus (BIO-RAD).

Example 6

Immunization with Soluble Form of GPC3 and Selection of Hybridoma

Since human GPC3 and mouse GPC3 show a high homology of 94% at the amino acid level, it was considered difficult to obtain an anti-GPC3 antibody if a normal mouse was immunized. Therefore, an autoimmune disease mouse, MRL/MpjUmmCrj-lpr/lpr mouse, (hereinafter referred to as MRL/lpr mouse, purchased from Charles River Japan, Inc.) was used as an immunized animal. Immunization was started at the age of 7 weeks or 8 weeks. For the first immunization, a soluble form of GPC3 was prepared at 100 μg/head and emulsified using Freund's complete adjuvant (FCA, Becton Dickinson) and subcutaneously administered. Two weeks later, a soluble form of GPC3 was prepared at 50 μg/head and emulsified using Freund's incomplete adjuvant (FIA, Becton Dickinson) and subcutaneously administered. After that, an additional immunization was carried out every other week for 5 times in total. To two of the immunized mice, a soluble form of GPC3 was diluted with PBS to 50 μg/head, and then administered intravenously via the tail as the final immunization. On the forth day after the final immunization, the spleen was excised to obtain a spleen cell, which was mixed with a mouse myeloma cell, P3-X63Ag8U1 (P3U1, purchased from ATCC), at a ratio of 2:1. Cell fusion was carried out by gradually adding PEG 1500 (Roche Diagnostic). RPMI 1640 medium (GIBCO BRL) was carefully added to dilute PEG 1500, and after PEG 1500 was removed by centrifugation, the cells were suspended in RPMI 1640 medium containing 10% FBS and inoculated into a 96-well culture plate at 100 μL/well. On the next day, RPMI 1640 medium containing 10% FBS, 1× HAT media supplement (SIGMA) and 0.5× BM-Condimed H1 Hybridoma cloning supplement (Roche Diagnostic) (hereinafter referred to as HAT medium) was added at 100 μL/well. After 2, 3 and 5 days, half of the culture solution was replaced with the HAT medium. After 7 days, screening was carried out using the culture supernatant. The screening was carried out by an ELISA using an immunoplate coated with the soluble form of GPC3 core protein. A positive clone was monocloned by the limiting dilution method. As a result, 11 clones of antibodies (M3C11, M13B3, M1E7, M3B8, M11F1, L9G11, M19B11, M6B1, M18D4, M5B9 and M10D2) that have a strong binding activity against GPC3 were obtained.

Example 7

Isotype Determination and Purification of Anti-GPC3 Antibody

Isotype was determined by an antigen-dependent ELISA using an Immunopure Monoclonal Antibody Isotyping Kit I (PIERCE). The purification of antibodies was carried out as follows. The culture supernatant of hybridoma cultured with the HAT medium supplemented with FBS (Ultra low IgG) (GIBCO BRL) was adsorbed to Hi Trap ProteinG HP (Amersham), and washed with a binding buffer (20 mM sodium phosphate (pH 7.0)). The antibody was eluted with an elution buffer (0.1 M glycine-HCl (pH 2.7)). The eluate was immediately neutralized with a neutralization buffer (1 M Tris-HCl (pH 9.0)), and dialyzed against PBS for day and night for buffer exchange.

Example 8

Evaluation of Binding Activity by ELISA

In order to conveniently evaluate the binding activity of the anti-GPC3 antibody thus obtained, concentration-dependent binding of the antibody was detected against an immunoplate containing the soluble form of GPC3 core protein immobilized thereon. A 3-fold dilution series (12 dilutions in total) of the purified antibody at a concentration of 10 μg/mL was added, and an anti-mouse IgG antibody was added as the secondary antibody. Color development was carried out using SIGMA 104. Since the degree of color development varies depending on the color development time, data measured precisely after 1 hour was analyzed. Every antibody showed a concentration-dependent color development. The correlation between the concentration of antibody and the degree of color development was plotted and an approximate curve was obtained by using an analyzing software, GraphPad Prism. Its EC50 value was determined as the index of the binding activity. EC50 values for all clones are shown in FIG. 16.

Example 9

Evaluation of Binding Activity by Flow Cytometry

Cells were dissociated with 1 mM EDTA pH 8.0 (GIBCO)/PBS and suspended in FACS buffer (1% FBS/PBS) at $1 \times 10^6$ cells/mL. The suspension was dispensed to a Multiscreen-HV Filter Plate (Millopre) at 100 μL/well and the supernatant was removed by centrifugation. An anti-GPC3 antibody diluted to an appropriate concentration was added and reacted on ice for 30 minutes. The cells were washed once with FACS buffer and an FITC-labeled anti-mouse IgG antibody was added and reacted on ice for 30 minutes. After the reaction, the cells were centrifuged at 500 rpm for 1 minute, and the supernatant was removed. The cells were suspended in 400 μL of FACS buffer and subjected to flow cytometry. EPICS ELITE ESP (Beckman Coulter) was used as a flow cytometer. A gate was set on the living cell population with the histogram of forward scatter and side scatter. As shown in FIG. 1, an anti-GPC3 antibody (M3C11, M11F1) bound strongly to the CHO cell expressing GPC3 and did not bind to the parent CHO cell, indicating that the antibody specifically binds to GPC3 presented on the cell membrane. In addition, the antibody showed the binding activity to a hepatoma cell line, HepG2 (purchased from ATCC) and HuH-7 (purchased from Health Science Research Resources Bank), suggesting that the antibody may specifically recognize hepatoma. The binding activity of the clones derived from the mouse immunized with a soluble form of GPC3 measured by flow cytometry is shown in FIG. 16, where the X-mode values of histogram at the concentration of antibody of 5 μg/mL are indicated.

Example 10

Epitope Classification by Competitive ELISA

The obtained antibodies were classified according to the epitopes by a competitive ELISA. The antibodies were biotinylated using a Biotin Labeling Kit (Roche). The soluble form of GPC3 core protein was diluted to 1 μg/mL with the coating buffer and added to a plate at 100 μL/well and stored at 4° C. overnight to coat the plate. On the next day, 200 μL of the substrate buffer was added for blocking. The plate was left at 4° C. overnight or longer and an anti-GPC3 antibody was added to the plate at 100 μL/well and reacted at room temperature for 1 hour. After that, without washing of the plate, 10 μL of 10 μg/mL biotin-labeled anti-GPC3 antibody was added and further reacted for 1 hour. The plate was washed with 300 μL/well of the rinse buffer for 3 times. AP-streptavidin conjugate (ZYMED) was diluted to 1000-fold with the dilution buffer and added at 100 μL/well and reacted at room temperature for 1 hour. The plate was washed with 300 μL/well of the rinse buffer for 5 times. SIGMA 104 was diluted to 1 mg/mL with the substrate buffer and added at 100

μL/well. After incubating for 1 hour at room temperature, the absorbance (at 405 nm, reference wavelength of 655 nm) was measured.

The results of the competitive ELISA are shown in FIG. 2. As for the antibody that competitively inhibited the binding of the biotinylated antibody by 50% or more, it was considered that its epitopes are located close together in the three-dimensional conformation. As a result of classification according to the competitive inhibition pattern of color development against the binding of the 8 types of biotinylated antibodies, the 11 clones derived from the mouse immunized with a soluble form of GPC3 were classified into 5 groups (a, b, c, d and e) (FIG. 16).

Example 11

Epitope Classification by Western Blotting

The soluble form of GPC3 core protein was applied to a 10% SDS-PAGE mini (TEFCO) and electrophoresed under reducing conditions. It was transferred to Immobilon-P (Millipore) using Trans-Blot SD Semi-Dry Electrophoretic Transfer Cell (BIO-RAD). After the membrane was briefly washed with TBS-T (0.05% Tween 20, TBS), it was shaken in TBS-T containing 5% skim milk for 1 hour. The membrane was shaken in TBS-T for about 10 minutes, then each anti-GPC3 antibody diluted with TBS-T containing 1% skim milk was added and the membrane was shaken for 1 hour. The membrane was washed with TBS-T and shaken in a solution of HRP-anti-mouse IgG antibody (Amersham) diluted with TBS-T containing 1% skim milk for 1 hour, and then washed with TBS-T. Color development was carried out using ECL-Plus (Amersham) and detected using Hyperfilm ECL (Amersham).

Figure 3:
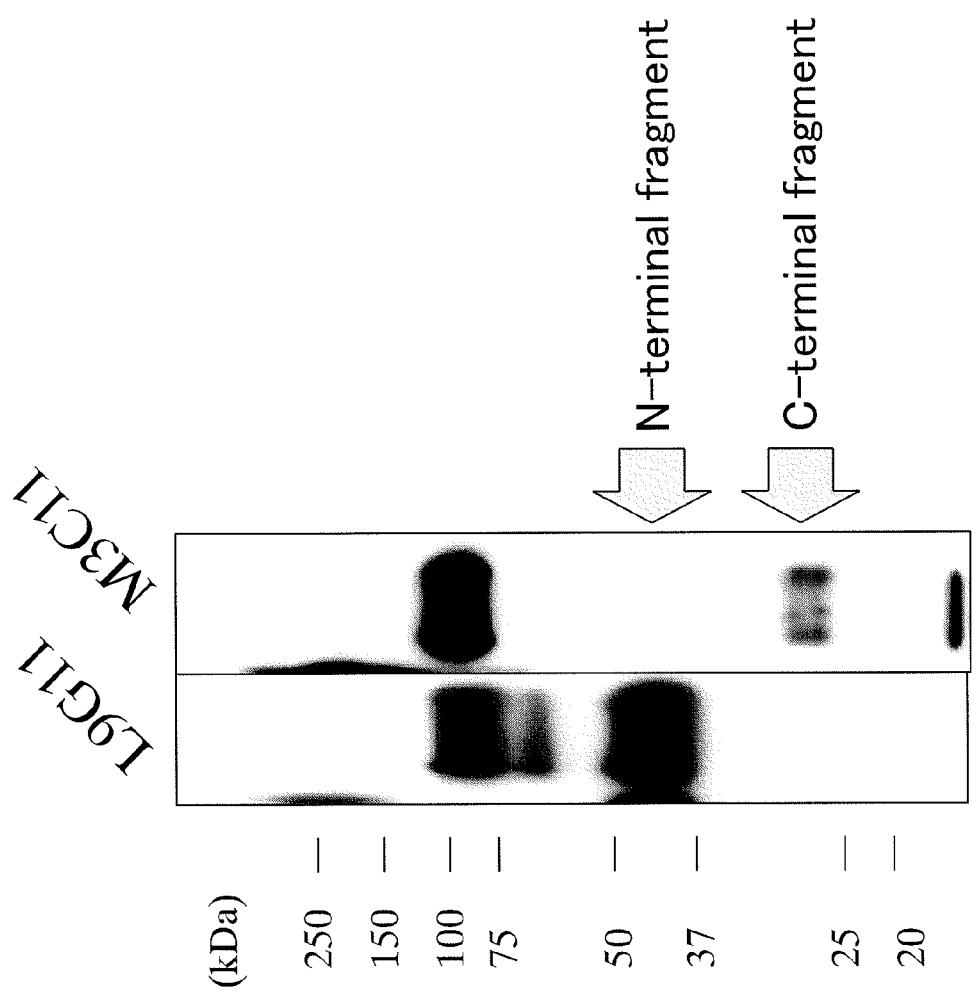
FIG. 3 shows the results of evaluating by Western blotting whether an anti-GPC3 antibody binds to the N-terminal fragment of 40 kDa of the soluble form of GPC3 core protein or to the C-terminal fragment of 30 kDa thereof. It was found that L9G11 binds to the N-terminal fragment and M3C11 binds to the C-terminal fragment.

As shown in FIG. 3, L9G11 was determined to be an antibody binding to the N-terminal side because it bound to the band of about 40 kDa. M3C11 was determined to be an antibody binding to the C-terminal side because it bound to the band of about 30 kDa. All the antibodies belonging to c, d or e group based on the competitive ELISA bound to the N-terminal side, and all those belonging to a or b groups bound to the C-terminal side (FIG. 16). L9G11 had higher detection sensitivity in Western blotting than the other antibodies that bind to the N-terminal side, suggesting that this antibody is a useful for detecting the N-terminal fragment by Western blotting.

Example 12

Detection of Secreted Form of GPC3

Since it was found that GPC3 is cleaved at the 358th amino acid residue or the 374th amino acid residue, the inventors hypothesized that a secreted form of GPC3 is secreted into the blood of a patient with liver cancer. Therefore, a GPC3 sandwich ELISA system was constructed in order to detect a secretory form of GPC3.

Figure 4:
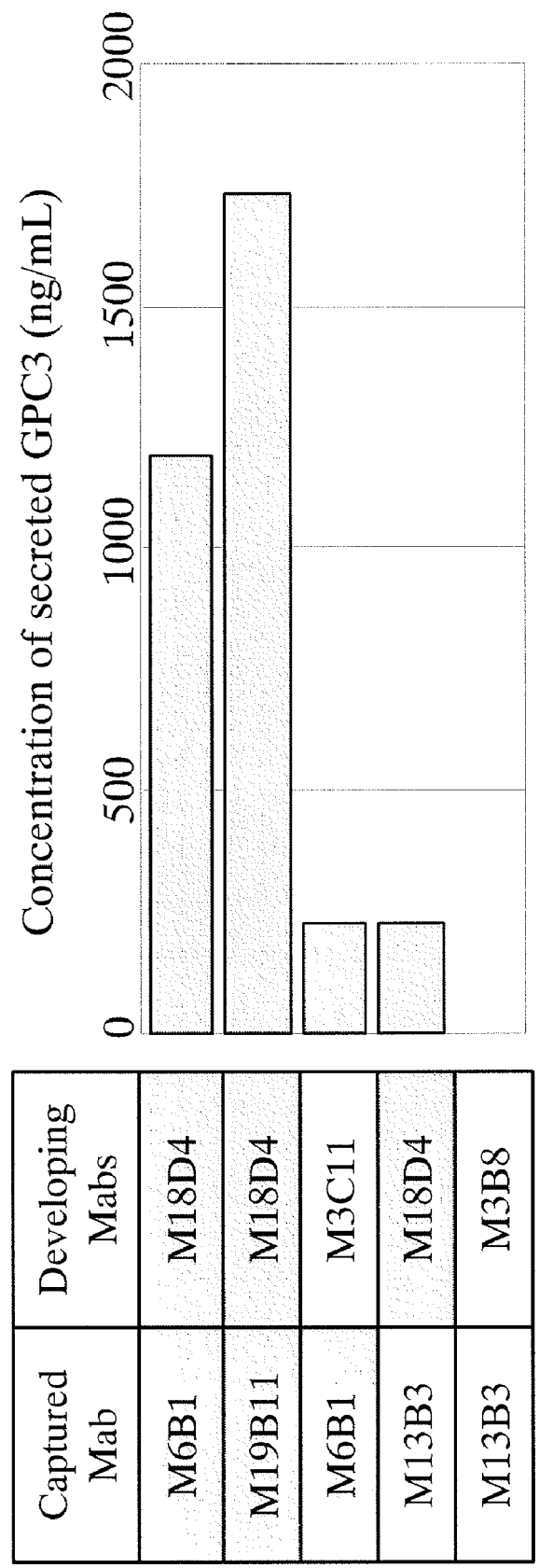
FIG. 4 shows the results of detecting a secreted form of GPC3 is present in the culture supernatant of HepG2 by a sandwich ELISA. It was strongly detected with the combination of antibodies that bind to the N-terminal fragment such as M6B1, M18D4 or M19B11, and it was not strongly detected with an antibody that binds to the C-terminal fragment such as M3C11, M13B3 or M3B8.

An immunoplate was coated with an anti-GPC3 antibody at 10 μg/mL and blocked by the substrate buffer. After the immunoplate was stored for several hours at room temperature or overnight at 4° C., the culture supernatant of HepG2 was added and incubated for 1 hour at room temperature. The immunoplate was washed with 300 μL/well of the rinse buffer for 3 times, and a biotin-labeled anti-GPC3 antibody diluted to 10 μg/mL was added and incubated for 1 hour at room temperature. The immunoplate was washed with 300 μL/well of the rinse buffer for 3 times, and AP-streptavidin was added and incubated for 1 hour at room temperature. The immunoplate was washed with 300 μL/well of the rinse buffer for 5 times. Color development was carried out using AMPAK (DAKO) in accordance with the attached protocol and the absorbance was measured using a microplate reader. The antibodies binding to the N-terminal side (M6B1, M19B11 and M18D4) and those binding to the C-terminal side (M3C11, M13B3 and M3B8) were combined to construct five sandwich ELISA systems. Each of these combinations showed an equivalent sensitivity in the standard curve using the secreted form of GPC3. These systems were evaluated using the culture supernatant of HepG2. The secreted form of GPC3 was detected at a high concentration of about 1 μg/mL with a combination of the antibodies binding to the N-terminal side (FIG. 4). The concentration detected with a combination of the antibodies binding to the C-terminal side was low, suggesting that the N-terminal fragment was dominantly present in the secreted form of GPC3.

Figure 5:
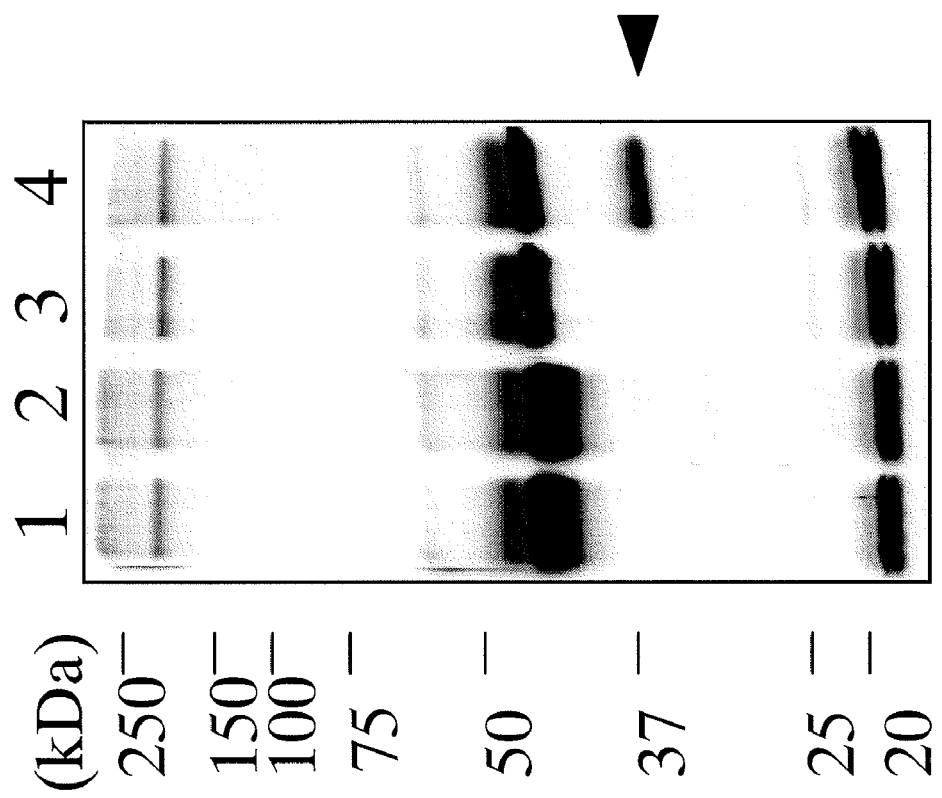
FIG. 5 shows the results of immunoprecipitation of the culture supernatant of HepG2 with the use of an anti-GPC3 antibody and detection of a secreted form of GPC3. The medium as a control (lanes 1 and 3) and the culture supernatant of HepG2 (lanes 2 and 4) were immunoprecipitated using M1E7 (lanes 1 and 2) and M10D2 (lanes 3 and 4). Secretory GPC3 was detected by M10D2 that binds to the N-terminal fragment.

Subsequently, the culture supernatant of HepG2 was immunoprecipitated using an anti-GPC3 antibody to detect the secreted form of GPC3. In the case where M10D2 that binds to the N-terminal fragment was used, the secreted form of GPC3 of 40 kDa was detected (FIG. 5). On the other hand, in the case where M1E7 that binds to the C-terminal fragment was used, the secreted form of GPC3 was not detected. The immunoprecipitation test was carried out for all the obtained GPC3 antibodies. Every antibody binding to the N-terminal fragment strongly detected the secreted form of GPC3, while the secreted form of GPC3 was not detected or was weakly detected with the use of the antibodies binding to the C-terminal fragment (FIG. 16). The antibody that can detect the secreted form of GPC3 by immunoprecipitation is expected to be useful as an antibody for diagnosing hepatoma. In addition, the antibody that can hardly detect the secreted form of GPC3 is expected to be useful in the development of a therapeutic antibody having an ADCC activity and a CDC activity, because such an antibody may migrate to the hepatoma lesion without being trapped in the secreted form of GPC3 present in the blood.

Example 13

Cloning of Variable Region of Anti-GPC3 Antibody

A variable region of the anti-GPC3 antibody was amplified by the RT-PCR method using the total RNA extracted from an anti-GPC3 antibody-producing hybridoma. The total RNA was extracted from 1×10$^7$ cells of the hybridoma with the use of RNeasy Plant Mini Kits (QIAGEN). By using 1 μg of the total RNA, the 5'-terminal gene fragment was amplified with the use of a SMART RACE cDNA Amplification Kit (CLONTECH) and any of the following synthetic oligonucleotides:
a synthetic oligonucleotide MHC-IgG1 complementary to the sequence of a mouse IgG1 constant region:
GGG CCA GTG GAT AGACAG ATG (SEQ ID NO: 7);
a synthetic oligonucleotide MHC-IgG2a complementary to the sequence of a mouse IgG2a constant region:
CAG GGG CCA GTG GAT AGA CCG ATG (SEQ ID NO: 8);
a synthetic oligonucleotide MHC-IgG2b complementary to the sequence of a mouse IgG2b constant region:
CAG GGG CCA GTG GAT AGA CTG ATG (SEQ ID NO: 9); and
a synthetic oligonucleotide kappa complementary to the sequence of a mouse kappa chain constant region:
GCT CAC TGG ATG GTG GGA AGA TG (SEQ ID NO: 10).

A reverse transcription reaction was carried out at 42° C. for 1 hour and 30 minutes. The PCR mixture (50 µL) contained 5 µL of 10× Advantage 2 PCR buffer, 5 µL of 10× Universal Primer A Mix, 0.2 mM dNTPs (DATP, dGTP, dCTP and dTTP), 1 µL of Advantage 2 Polymerase Mix (all from CLONTECH), 2.5 µL of the reverse transcription reaction product and 10 pmol of the synthetic oligonucleotide MHC-IgG1, MHC-IgG2a, MHC-IgG2b or kappa. PCR was carried out with 5 cycles consisting of 94° C. for 30 seconds, 94° C. for 5 seconds and 72° C. for 3 minutes, 5 cycles consisting of 94° C. for 5 seconds, 70° C. for 10 seconds and 72° C. for 3 minutes, and 25 cycles consisting of 94° C. for 5 seconds, 68° C. for 10 seconds and 72° C. for 3 minutes. Lastly, the reaction product was heated at 72° C. for 7 minutes. Each PCR product was purified from the agarose gel using a QIAquick Gel Extraction Kit (QIAGEN), cloned into pGEM-T Easy vector (Promega), and the nucleotide sequence was determined.

The nucleotide sequences of the H chain variable regions of M3C11, M13B3, M1E7, M3B8, M11F1, M19B11, M6B1, M18D4, M5B9, M10D2 and L9G11 are shown in SEQ ID NOs: 11, 12, 13, 14, 15, 16, 17, 18, 19, 20 and 21, respectively, the amino acid sequences thereof are shown in SEQ ID NOs: 22, 23, 24, 25, 26, 27, 28, 29, 30, 31 and 32, respectively. The nucleotide sequences of the L chain variable regions thereof are shown in SEQ ID NOs: 33, 34, 35, 36, 37, 38, 39, 40, 41, 42 and 43, respectively, and the amino acid sequences thereof are shown in SEQ ID NOs: 44, 45, 46, 47, 48, 49, 50, 51, 52, 53 and 54, respectively.

Example 14

Epitope Classification Using GST-Fusion Protein

Figure 6:
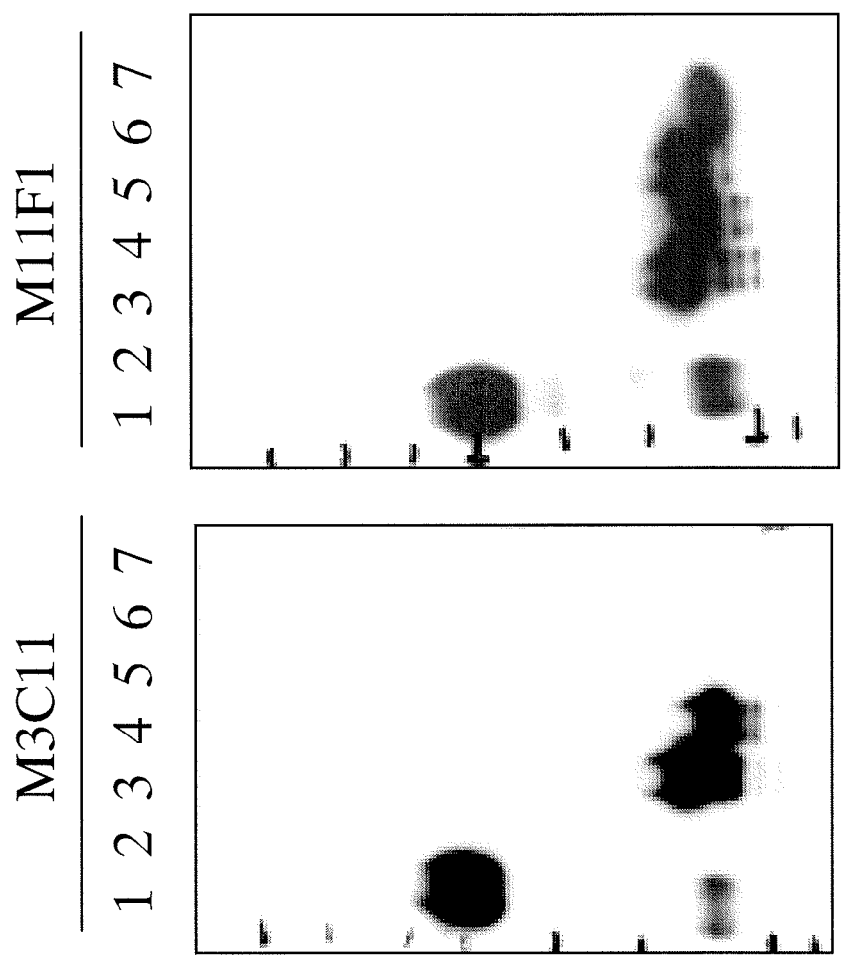
FIG. 6 shows the results of analyzing the epitope of the antibodies that bind to the C-terminal fragment of GPC3 by Western blotting with the use of a fusion protein of the C-terminal peptide of GPC3 and GST. The soluble form of GPC3 core protein (lane 1), GST (lane 2), GC-1 (lane 3), GC-2 (lane 4), GC-3 (lane 5), GC-4 (lane 6) and GC-5 (lane 7) were subjected to SDS electrophoresis under reducing conditions, and detected by Western blotting using M3C11 and M11F1.

To carry out a detail analysis of the epitopes for the antibodies binding to the C-terminal fragment, fusion proteins of successively shortened C-terminal peptides of GPC3 with GST, namely GC-1 (from Ser495 to Lys563), GC-2 (from Gly510 to Lys563), GC-3 (from Ala524 to Lys563), GC-4 (from Gly537 to Lys563) and GC-5 (from Ser550 to Lys563) were prepared. The C-terminal region of GPC3 was cloned into pGEX-4T-3 (Amersham) to construct a plasmid DNA in which the C-terminal region of GPC3 is ligated to the C-terminal side of GST. The plasmid DNA was introduced into DH5α, whereby a transformant was obtained. Then, IPTG was added at 1 mM to a culture of the transformant in the logarithmic growth phase to induce the expression of a GST-fusion protein. The bacterial cells were collected after 2 hours cultivation. The cells were homogenized by sonication, and centrifuged at 35,000 rpm for 30 minutes with XL-80 ultracentrifuge (Beckman, 70.1 Ti rotor). Then, the culture supernatant was recovered and purified with GST Purification Modules (Amersham). The thus purified GST-fusion proteins were separated by SDS-PAGE under reducing conditions, and Western blotting was carried out with the anti-GPC3 antibodies (FIG. 6). M3C11 and M1E7 detected GC-1 and GC-2, while they did not detect GC-3, GC-4 and GC-5, indicating that the epitopes of these antibodies are contained in the region of GC-2, and that the region of GC-3 is not sufficient. M3B8 and M11F1 detected GC-1 GC-2, GC-3 and GC-4, while they did not detect GC-5, indicating that the epitopes of these antibodies are contained in the region of GC-4, and that the region of GC-5 is not sufficient. The minimum region of the GST-fusion protein to which each antibody can bind is listed in the column headed "Western blotting" of FIG. 16.

Example 15

Preparation of Anti-GPC3 Mouse-Human Chimeric Antibody

The sequences of the H chain and the L chain variable regions of the anti-GPC3 antibodies were ligated to the sequences of a human IgG1 and a kappa chain constant regions. PCR was carried out by using a synthetic oligonucleotide, which is complementary to the 5'-terminal nucleotide sequence of the H chain variable region of each antibody and has a Kozak sequence, and a synthetic oligonucleotide, which is complementary to the 3'-terminal nucleotide sequence and has a NheI site. The obtained PCR product was cloned into pB-CH vector in which a human IgG1 constant region was inserted into pBluescript KS(+) vector (Toyobo). The mouse H chain variable region and the human H chain (γ1 chain) constant region are ligated via the NheI site. The prepared H chain gene fragment was cloned into an expression vector, pCXND3. On the other hand, PCR was carried out by using a synthetic oligonucleotide, which is complementary to the 5'-terminal nucleotide sequence of the L chain variable region of each antibody and has a Kozak sequence, and a synthetic oligonucleotide, which is complementary to the 3'-terminal nucleotide sequence and has a BsiWI site. The obtained PCR product was cloned into pB-CL vector in which the human kappa chain constant region was inserted into pBluescript KS(+) vector (Toyobo). The human L chain variable region and the constant region are ligated via the BsiWI site. The prepared L chain gene fragment was cloned into an expression vector, pUCAG. This pUCAG vector was obtained by cloning a 2.6 kbp fragment obtained by digesting pCXN (Niwa et al., Gene 1991; 108: 193-200) with a restriction enzyme BamHI into the BamHI site of pUC19 vector (Toyobo).

To prepare an expression vector for an anti-GPC3 mouse-human chimeric antibody, a gene fragment was obtained by digesting the pUCAG vector containing the L chain gene fragment with a restriction enzyme HindIII (Takara Shuzo), and cloned into the HindIII site of the pCXND3 containing the H chain gene. This plasmid will express a neomycin-resistance gene, DHFR gene and an anti-GPC3 mouse-human chimeric antibody in an animal cell.

A CHO cell line (DG44 cell line) stably expressing the antibody was prepared as follows. The gene was introduced into the cells by the electroporation method using Gene Pulser II (Bio-Rad). A mixture obtained by mixing 25 µg of the expression vector for each anti-GPC3 mouse-human chimeric antibody and 0.75 mL of a solution of CHO cells suspended in PBS (1×10$^7$ cell/mL) was cooled on ice for 10 minutes, and transferred to a cuvette. Then, a pulse was applied at 1.5 kV and a capacitance of 25 µFD. After a 10-minute recovery period at room temperature, the electroporated cells were suspended in 40 mL of CHO-S-SFM II medium (Invitrogen) containing 1× HT supplement (Invitrogen). The suspension was diluted to 50-fold with the same medium, and dispensed to a 96-well culture plate at 100 µL/well. After a 24-hour culture in a $CO_2$ incubator (5% $CO_2$), Geneticin (Invitrogen) was added at 0.5 mg/mL and the cells were cultured for 2 weeks. The culture supernatant was taken from the well having a Geneticin resistant transformed cell colony and the amount of IgG was measured by the concentration determination method described below. A high-producing cell line was successively expanded to obtain a cell line that stably expresses an anti-GPC3 mouse-human chimeric antibody. The cell line was cultured at a large-scale and the culture supernatant was collected. The purification of each anti-GPC3 mouse-human chimeric antibody was carried out using Hi Trap ProteinG HP (Amersham).

Example 16

Measurement of Complement-Dependent Cytotoxicity Activity (CDC Activity)

16.1 Preparation of Human Albumin Veronal Buffer (HAVB)

In milli-Q water, 12.75 g of NaCl (highest grade, Wako Pure Chemicals), 0.5625 g of Na-Barbital (highest grade, Wako Pure Chemicals) and 0.8625 g of Barbital (highest grade, Wako Pure Chemicals) were dissolved to a final volume of 200 mL and autoclaved at 121° C. for 20 minutes. Then, 100 mL of autoclaved hot milli-Q water was added. The pH was 7.43 (recommended pH: 7.5). The solution was used as a 5× veronal buffer. In 50 mL of milli-Q water, 0.2205 g of $CaCl_2.2H_2O$ (highest grade, Junsei Chemical) was dissolved to a final concentration of 0.03 mol/L, which was used as a $CaCl_2$ solution. In 50 mL of milli-Q water, 1.0165 g of $MgCl_2.6H_2O$ (highest grade, Junsei Chemical) was dissolved to a final concentration of 0.1 mol/L, which was used as a $MgCl_2$ solution. In milli-Q water, 100 mL of the 5× veronal buffer, 4 mL of human serum albumin (25% Buminate (registered trademark), the concentration of human serum albumin: 250 mg/mL, Baxter Healthcare), 2.5 mL of the $CaCl_2$ solution, 2.5 mL of the $MgCl_2$ solution, 0.1 g of KCl (highest grade, Junsei Chemical) 0.5 g of glucose (D(+)-glucose, anhydrous glucose, highest grade, Wako Pure Chemicals) were dissolved to a final volume of 500 mL, which was used as HAVB. After filter sterilization, the HAVB was stored at a preset temperature of 5° C.

16.2 Preparation of Target Cell

The CHO cell expressing full-length human GPC3 prepared in Example 4 was cultured in α-MEM medium containing nucleic acid (+) (GIBCO) supplemented with 10% FBS and 0.5 mg/mL Geneticin (GIBCO). The cells were dissociated from the dish using a cell dissociation buffer (Invitrogen Corp), dispensed to each well of a 96-well flat-bottomed plate (Falcon) at $1×10^4$ cells/well, and cultured for 3 days. After the cultivation, 5.55 MBq of chromium-51 was added, and the cells were cultured in a 5% carbon dioxide gas incubator at 37° C. for 1 hour. These cells were washed with HAVB twice, and 50 μL of HAVB was added and used as a target cell.

16.3 Chromium Release Test (CDC Activity)

Each chimeric antibody was diluted with HAVB to make a 40 μg/mL antibody solution. To the target cell, 50 μL of each antibody solution was added, and left on ice for 15 minutes. Subsequently, to each well, 100 μL of the human serum from the peripheral blood of a healthy volunteer, which had been diluted with HAVB, was added to a final concentration of 25% (the final concentration of antibody: 10 μg/mL), and left in a 5% carbon dioxide gas incubator at 37° C. for 90 minutes. After the plate was centrifuged, 100 μL of the supernatant was collected from each well, the radioactivity was measured using a gamma counter. The specific chromium release rate was obtained by the following formula.

Specific chromium release rate(%)=$(A-C)×100/(B-C)$

"A" represents the radioactivity (cpm) in each well, "B" represents the mean value of the radioactivities (cpm) in the wells in which 100 μL of 2% NP-40 aqueous solution (Nonidet P-40, Code No. 252-23, Nacalai Tesque) and 50 μL of HAVB were added to the target cell, and "C" represents the mean value of the radioactivities (cpm) in the wells in which 150 μL of HAVB was added to the target cell. The test was carried out in triplicate and the mean value and the standard deviation were calculated for CDC activity (%).

Figure 7:
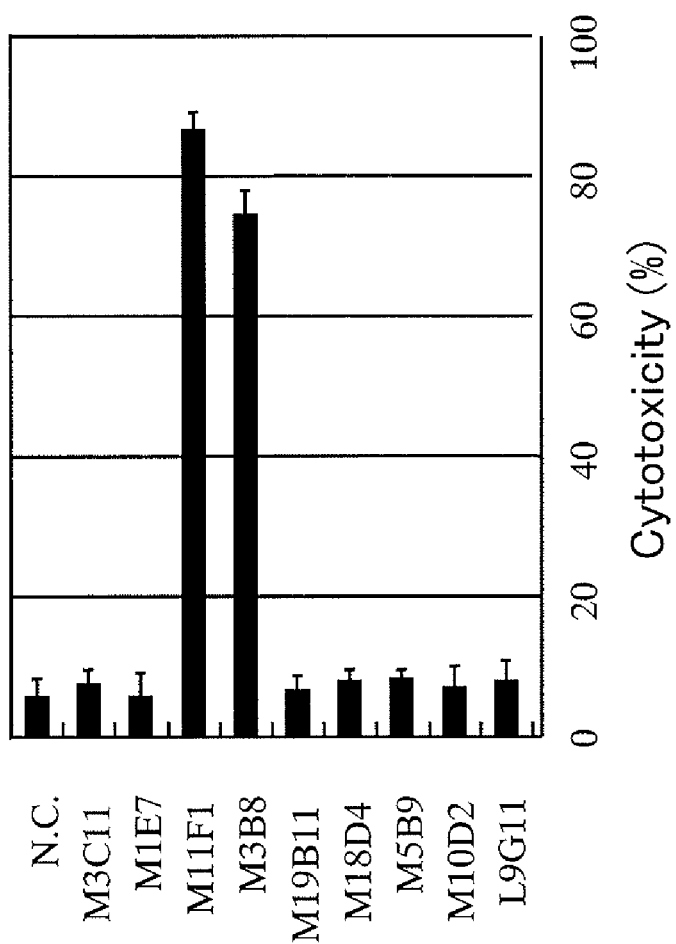
FIG. 7 shows the results of evaluating the CDC activity of the anti-GPC3 mouse-human chimeric antibody to a CHO cell that expresses GPC3.

The results are shown in FIG. 7. Among 9 types of the anti-GPC3 chimeric antibodies, M3B8 and M11F1, which are an antibody recognizing the C-terminal side, showed a strong CDC activity against the CHO cell expressing GPC3, however, the CDC activity was not observed in the other antibodies. M3B8 and M11F1 belong to the group called "b" based on the competitive ELISA, and an important epitope for showing a strong CDC activity could be found.

Example 17

Measurement of ADCC Activity Using PBMC Derived from Human Peripheral Blood 17.1 Preparation of Human PBMC Solution The heparinized peripheral blood obtained from a healthy volunteer was diluted to 2-fold with PBS(−), and overlayered on Ficoll-Paque™ PLUS (Amersham). After centrifugation at 500×g for 30 minutes at 20° C., the middle layer, which is the mononuclear leukocyte fraction, was collected. The cells were washed 3 times, suspended in 10% FBS/RPMI and used as a human PBMC solution.

17.2 Preparation of target Cell

The HepG2 cells cultured in 10% FBS/RPMI 1640 medium were dissociated from the dish using Trypsin-EDTA (Invitrogen), dispensed to each well of a 96-well U-bottomed plate (Falcon) at $1×10^4$ cells/well, and cultured for 2 days. The CHO cell expressing full-length human GPC3 prepared in Example 4 was cultured in α-MEM nucleic acids (+) medium (GIBCO) supplemented with 10% FBS and 0.5 mg/mL Geneticin (GIBCO). The cells were dissociated from the dish using a cell dissociation buffer (Invitrogen Corp), dispensed to each well of a 96-well flat-bottomed plate (Falcon) at $1×10^4$ cells/well, and cultured for 3 days. Chromium-51 (5.55 MBq) was added to each cell and the cells were cultured in a 5% carbon dioxide gas incubator at 37° C. for 1 hour. These cells were washed with the medium once, and 50 μL of 10% FBS/RPMI 1640 medium was added and used as a target cell.

17.3 Chromium Release Test (ADCC Activity)

To the target cell, 50 μL of an antibody solution prepared at different concentrations was added, and reacted on ice for 15 minutes. Subsequently, 100 μL of the human PBMC solution was added at $5×10^5$ cells/well, and cells were cultured in a 5% carbon dioxide gas incubator at 37° C. for 4 hours. After the cultivation, the plate was centrifuged, and the radioactivity in 100 μL of the culture supernatant was measured using a gamma counter. The specific chromium release rate was obtained by the following formula.

specific chromium release rate(%)=$(A-C)×100/(B-C)$

Figure 8:
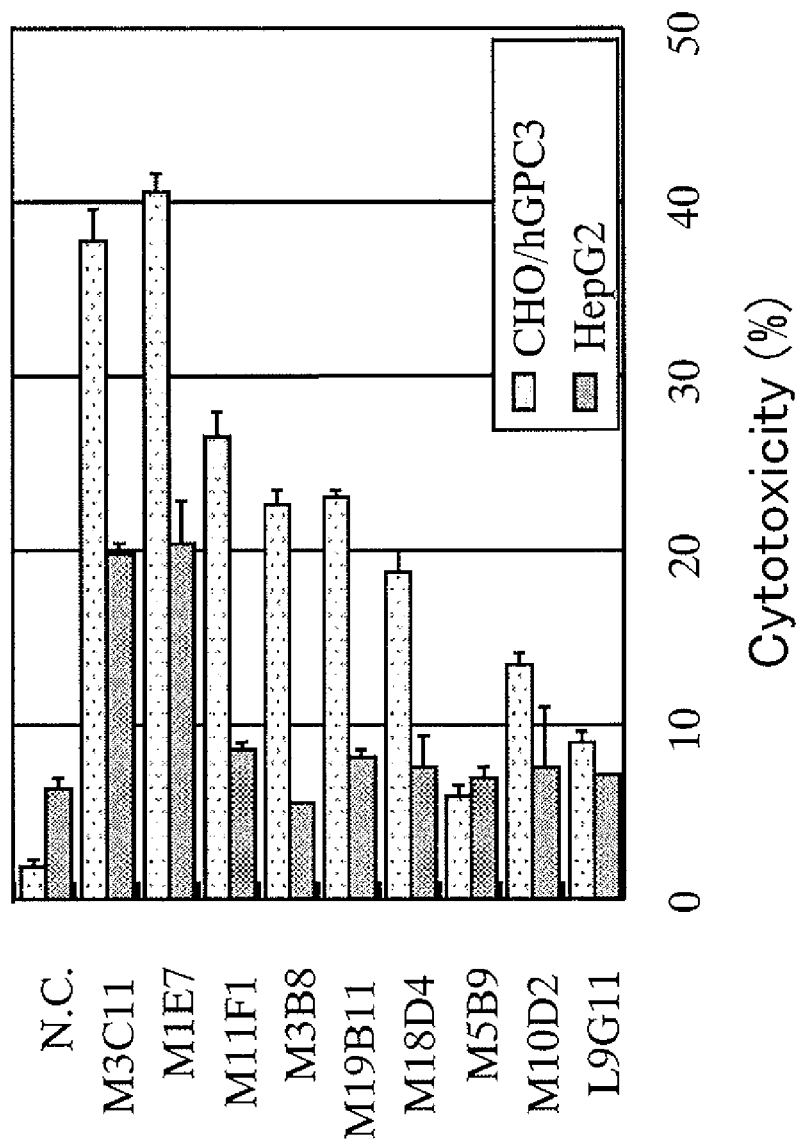
FIG. 8 shows the results of evaluating the ADCC activity of the anti-GPC3 mouse-human chimeric antibody to a CHO cell that expresses GPC3 and HepG2.

"A" represents the mean value of the radioactivities (cpm) in each well, "B" represents the mean value of the radioactivities (cpm) in the wells in which 100 μL of 2% NP-40 aqueous solution (Nonidet P-40, Code No. 252-23, Nacalai Tesque) and 50 μL of 10% FBS/RPMI medium were added to the target cell, and "C" represents the mean value of the radioactivities (cpm) in the wells in which 150 μL of 10% FBS/RPMI medium was added to the target cell. The test was carried out in triplicate and the mean value and the standard deviation were calculated for ADCC activity (%). The results are shown in FIG. 8. Among 9 types of the anti-GPC3 chimeric antibodies, the antibodies recognizing the C-terminal side had a tendency of showing a strong ADCC activity.

Example 18

Immunization with GC-3 and Selection of Hybridoma

Among the obtained anti-GPC3 antibodies, only M11F1 and M3B8 showed a strong CDC activity, indicating that the CDC activity is epitope dependent. To obtain an antibody having both ADCC activity and CDC activity, a GST-fusion protein containing the epitope for M11F1 and M3B8, referred to as GC-3, was used for immunization. A large mount of GC-3 was purified by the above-mentioned method. The buffer was changed to PBS by gel filtration using Superdex 75 (Amersham). The obtained product was used as immunoprotein. using three Balb/c mice (purchased from Charles River Japan, Inc.) and three MRL/lpr mice were immunized with GC-3 in accordance with the above-mentioned method. For the first immunization, GC-3 was prepared at 100 µg/head and emulsified using FCA, which was subcutaneously administered. Two weeks later, GC-3 was prepared at 50 µg/head and emulsified using FIA, which was subcutaneously administered. After the fifth immunization, the final immunization (50 µg/head) was carried out for all mice by intravenously administering the immunoprotein via the tail. After cell fusion, hybridoma were screened by an ELISA using an immunoplate coated with the soluble form of GPC3 core protein. A positive clone was monocloned by the limiting dilution method. As a result, 5 clones of antibodies (GC199, GC202, GC33, GC179 and GC194) that have a strong binding activity against GPC3 were obtained.

The antibody was purified from the culture supernatant of the hybridoma using Hi Trap proteinG HP, and analyzed in accordance with the above-mentioned method. The EC50 value was calculated by an ELISA using an immunoplate coated with the soluble form of GPC3 core protein, and the X-mode value of histogram at 5 µg/mL was measured by flow cytometry (FIG. 17). According to the epitope classification by a competitive ELISA, the antibodies were classified into the group b (GC199, GC202 and GC33) and a new epitope group f (GC179 and GC194) The epitope classification using the GST-fusion proteins indicated that GC199, GC202 and GC33 detected GC-1, GC-2, GC-3 and GC-4, but did not detect GC-5, suggesting that the epitopes for these antibodies are contained in the region of GC-4 in the same manner as the epitopes for M11F1 and M3B8, and that the region of GC-5 is not sufficient. On the other hand, GC179 and GC194 detected GC-1, GC-2 and GC-3, but did not detect GC-4 and GC-5, suggesting that the epitopes for these antibodies are contained in the region of GC-3, and that the region of GC-4 is not sufficient. The minimum region of the GST-fusion protein to which each antibody can bind is listed in the column headed "Western blotting" of FIG. 17.

The H chain and the L chain variable regions of GC199, GC202, GC33, GC179 and GC194 were cloned in accordance with the above-mentioned method, and their sequences were determined. As for the L chain of GC194, 2 types of sequences were cloned. The nucleotide sequences of the H chain variable regions of GC199, GC202, GC33, GC179 and GC194 are shown in SEQ ID NOs: 55, 56, 57, 58 and 59, respectively, and the amino acid sequences thereof are shown in SEQ ID NOs: 60, 61, 62, 63 and 64, respectively. The nucleotide sequences of the L chain variable regions of GC199, GC202, GC33, GC179, GC194(1) and GC194(2) are shown in SEQ ID NOs: 65, 66, 67, 68, 69 and 70 respectively, and the amino acid sequences thereof are shown in SEQ ID NOs: 71, 72, 73, 74, 75 and 76, respectively.

Further, these amino acid sequences were examined for homology by comparing with the database of the amino acid sequences of known antibodies, whereby their CDR regions were determined as follows.

| Antibody | CDR | Amino Acid Sequence | SEQ ID NO |
|---|---|---|---|
| M13B3 (H) | CDR1 | NYAMS | 103 |
|  | CDR2 | AINNNGDDTYYLDTVKD | 104 |
|  | CDR3 | QGGAY | 105 |
| M3B8 (H) | CDR1 | TYGMGVG | 106 |
|  | CDR2 | NIWWYDAKYYNSDLKS | 107 |
|  | CDR3 | MGLAWFAY | 108 |
| M11F1 (H) | CDR1 | IYGMGVG | 109 |
|  | CDR2 | NIWWNDDKYYNSALKS | 110 |
|  | CDR3 | IGYFYFDY | 111 |
| M5B9 (H) | CDR1 | GYWMH | 112 |
|  | CDR2 | AIYPGNSDTYNYQKFKG | 113 |
|  | CDR3 | SGDLTGGLAY | 114 |
| M6B1 (H) | CDR1 | SYAMS | 115 |
|  | CDR2 | AINSNGGTTYYPDTMKD | 116 |
|  | CDR3 | HNGGYENYGWFAY | 117 |
| M10D2 (H) | CDR1 | SYWMH | 118 |
|  | CDR2 | EIDPSDSYTYYNQKFRG | 119 |
|  | CDR3 | SNLGDGHYRFPAFPY | 120 |
| L9G11 (H) | CDR1 | SYWMH | 118 |
|  | CDR2 | TIDPSDSETHYNLQFKD | 121 |
|  | CDR3 | GAFYSSYSYWAWFAY | 122 |
| GC33 (H) | CDR1 | DYEMH | 123 |
|  | CDR2 | ALDPKTGDTAYSQKFKG | 124 |
|  | CDR3 | FYSYTY | 125 |
| GC179 (H) | CDR1 | INAMN | 126 |
|  | CDR2 | RIRSESNNYATYYGDSVKD | 127 |
|  | CDR3 | EVTTSFAY | 128 |
| GC194 (H) | CDR1 | ASAMN | 129 |
|  | CDR2 | RIRSKSNNYAIYYADSVKD | 130 |
|  | CDR3 | DPGYYGNPWFAY | 131 |
| GC199 (H) | CDR1 | DYSMH | 132 |
|  | CDR2 | WINTETGEPTYADDFKG | 133 |
|  | CDR3 | LY | 134 |
| GC202 (H) | CDR1 | TYGMGVG | 106 |
|  | CDR2 | NIWWHDDKYYNSALKS | 135 |
|  | CDR3 | IAPRYNKYEGFFAF | 136 |
| M13B3 (L) | CDR1 | KSSQSLLDSDGKTYLN | 137 |
|  | CDR2 | LVSKLDS | 138 |
|  | CDR3 | WQGTHFPLT | 139 |
| M3B8 (L) | CDR1 | KASQDINNYLS | 140 |
|  | CDR2 | RANRLVD | 141 |
|  | CDR3 | LQCDEFPPWT | 142 |
| M11F1 (L) | CDR1 | RSSQSLVHSNGNTYLH | 143 |
|  | CDR2 | KVSNRFS | 144 |
|  | CDR3 | SQSTHVPWT | 145 |
| M5B9 (L) | CDR1 | RSSKSLLHSNGITYLY | 146 |
|  | CDR2 | QMSNLAS | 147 |
|  | CDR3 | AQNLELPYT | 148 |
| M6B1 (L) | CDR1 | KASQDINKNII | 149 |
|  | CDR2 | YTSTLQP | 150 |
|  | CDR3 | LQYDNLPRT | 151 |
| M10D2 (L) | CDR1 | RASHSISNFLH | 152 |
|  | CDR2 | YASQSIS | 153 |
|  | CDR3 | QQSNIWSLT | 154 |
| L9G11 (L) | CDR1 | RASESVEYYGTSLMQ | 155 |
|  | CDR2 | GASNVES | 156 |
|  | CDR3 | QQSRKVPYT | 157 |
| GC33 (L) | CDR1 | RSSQSLVHSNGNTYLH | 143 |
|  | CDR2 | KVSNRFS | 144 |
|  | CDR3 | SQNTHVPPT | 158 |
| GC179 (L) | CDR1 | KSSKSLLHSNGNTYLN | 159 |
|  | CDR2 | WMSNLAS | 160 |
|  | CDR3 | MQHIEYPFT | 161 |
| GC194 (L) 1 | CDR1 | RSSKSLLHSYDITYLY | 162 |
|  | CDR2 | QMSNLAS | 147 |
|  | CDR3 | AQNLELPPT | 163 |

-continued

| Antibody | CDR | Amino Acid Sequence | SEQ ID NO |
|---|---|---|---|
| GC194 (L) 2 | CDR1 | SASSSVSYMY | 164 |
|  | CDR2 | DTSNLAS | 165 |
|  | CDR3 | QQWSSYPLT | 166 |
| GC199 (L) | CDR1 | KSSQSLLHSDGKTFLN | 167 |
|  | CDR2 | LVSRLDS | 168 |
|  | CDR3 | CQGTHFPRT | 169 |
| GC202 (L) | CDR1 | RSSQSIVHSNGNTYLE | 170 |
|  | CDR2 | KVSNRFS | 144 |
|  | CDR3 | FQGSHVPWT | 171 |

Example 19

Measurement of ADCC Activity Using Mouse Bone Marrow Derived Effector Cell 19.1 Preparation of Mouse Bone Marrow Derived Effector Cell Solution Bone marrow cells were collected from the femur of an SCID mouse (CLEA Japan, Inc., male, 10 weeks old), and suspended in 10% FBS/RPMI 1640 medium at $5 \times 10^5$ cells/mL. Mouse GM-CSF (PeproTech) and human IL-2 (PeproTech) were added at 10 ng/mL and 50 ng/mL, respectively, and the cells were cultured in a 5% carbon dioxide gas incubator at 37° C. for 5 days. After the cultivation, the cells were scraped off with a scraper and washed with the medium once. Then, the cells were suspended in 10% FBS/RPMI 1640 medium at $5 \times 10^6$ cells/mL, and used as a mouse bone marrow derived effector cell solution.

19.2 Preparation of Target Cell

A human hepatoma cell line, HuH-7, was maintained and subcultured with DMEM medium (SIGMA) containing 10% FBS (ThermoTrace). The cells were dissociated from the dish using Cell Dissociation Buffer (Invitrogen), dispensed to each well of a 96-well U-bottomed plate (Falcon) at $1 \times 10^4$ cells/well, and cultured for 1 day. After the cultivation, 5.55 MBq of chromium-51 was added, and the cells were cultured in a 5% carbon dioxide gas incubator at 37° C. for 1 hour. These cells were washed with the medium once, and 50 µL of 10% FBS/RPMI 1640 medium was added and used as a target cell.

19.3 Chromium Release Test (ADCC Activity)

To the target cell, 50 µL of an antibody solution prepared at different concentrations was added, and reacted on ice for 15 minutes. Subsequently, 100 µL of the mouse bone marrow derived effector cell solution ($5 \times 10^5$ cells/well) was added, and cells were cultured in a 5% carbon dioxide gas incubator at 37° C. for 4 hours. After the cultivation, the plate was centrifuged, and the radioactivity in 100 µL of the culture supernatant was measured using a gamma counter. The specific chromium release rate was obtained by the following formula.

$$\text{Specific chromium release rate}(\%) = (A-C) \times 100/(B-C)$$

"A" represents the mean value of the radioactivities (cpm) in each well, "B" represents the mean value of the radioactivities (cpm) in the wells in which 100 µL of 2% NP-40 aqueous solution (Nonidet P-40, Code No. 252-23, Nacalai Tesque) and 50 µL of 10% FBS/RPMI medium were added to the target cell, and "C" represents the mean value of the radioactivities (cpm) in the wells in which 150 µL of 10% FBS/RPMI medium was added to the target cell. The test was carried out in triplicate and the mean value and the standard deviation were calculated for ADCC activity (%).

Figure 9:
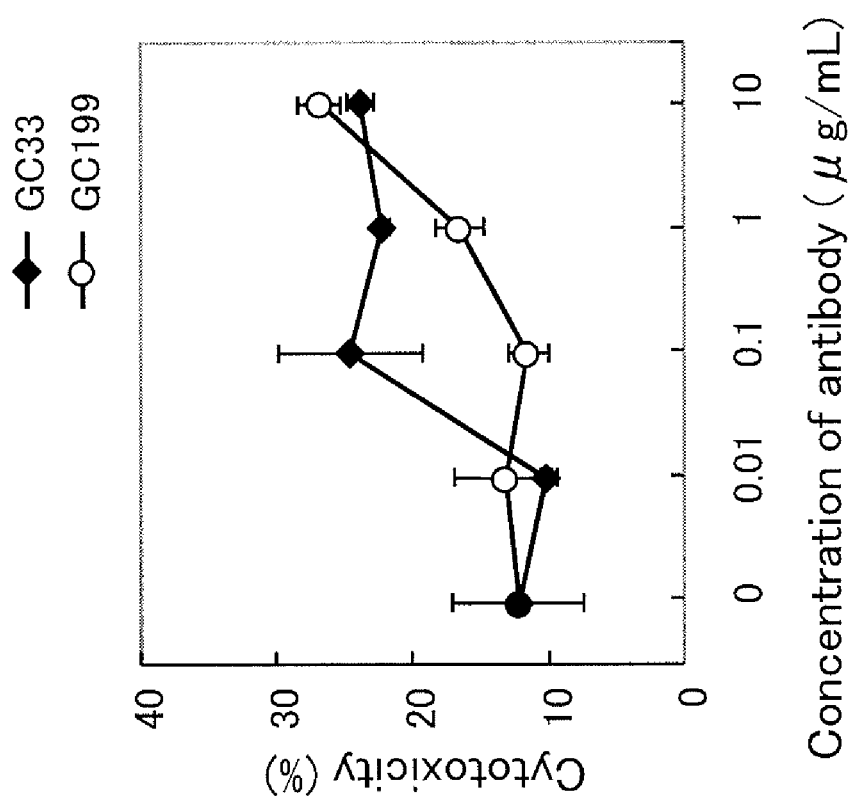
FIG. 9 shows the results of evaluating the ADCC activity of GC33 to a human hepatoma cell line, HuH-7, using a mouse bone marrow-derived effector cell.

The results are shown in FIG. 9. It was revealed that GC33 antibody shows an ADCC activity when the concentration of antibody is 0.1 µg/mL or higher, and shows stronger activity than GC199 antibody.

Example 20

Antitumor Activity of GC33 Antibody to Mouse Model Transplanted with Human Hepatoma 20.1 Preparation of Mouse Model Transplanted With Human Hepatoma A human hepatoma cell line, HuH-7, was prepared at $5 \times 10^7$ cells/mL in a solution containing DMEM medium and MATRIGEL (BD Bioscience) at a ratio of 1:1. On the previous day, 100 µL of an anti-asialo GM1 antibody solution (Wako Pure Chemicals, one vial was dissolved with 1 mL of distilled water for injection then added 4 mL of physiologic saline) was intraperitoneally administered to a SCID mouse (male, 5 weeks old, CLEA Japan, Inc.). The mouse was transplanted with 100 µL of the above-mentioned cell suspension ($5 \times 10^6$ cells/mouse) subcutaneously in the abdominal area.

20.2 Preparation and Administration of Antibody

Starting from the day 20 after the cell transplantation, an antibody solution prepared on the day of administration at 0.5 mg/mL (group of administration of 5 mg/kg) and at 0.1 mg/mL (group of administration of 1 mg/kg) with PBS(−) was administered to the mouse model transplanted with a human hepatoma cells at 10 mL/kg via the tail vein once a week for 3 weeks. As a negative control, PBS(−) (vehicle) was administered at 10 mL/kg via the tail vein once a week for 3 weeks in a similar manner. Both groups consisted of 6 mice each.

20.3 Evaluation of Antitumor Effect

The antitumor effect of GC33 antibody on the mouse model transplanted with human hepatoma cells was evaluated with the change in tumor volume with time and tumor weight at 1 week after the final administration. The tumor volume was calculated by the following formula.

$$\text{Tumor volume} = (\text{major axis}) \times (\text{minor axis}) \times (\text{minor axis})/2$$

Figure 10:
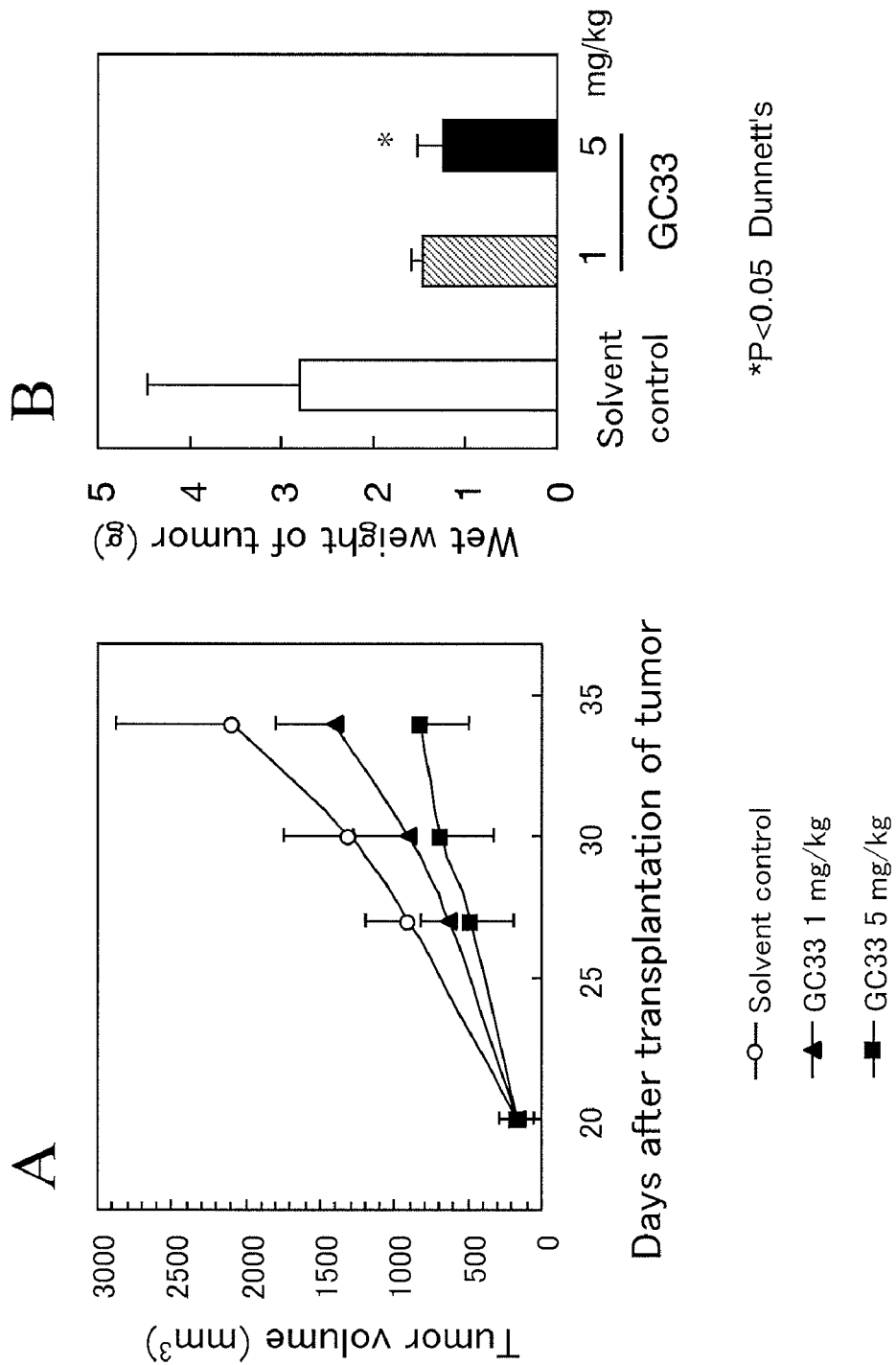
FIG. 10 shows the results of evaluating the antitumor activity of GC33 antibody to a mouse model transplanted with human hepatoma.

As shown in FIG. 10, a significant inhibition of tumor growth was observed in the GC33 antibody group compared with the vehicle group.

Consequently, GC33 was shown to have an antitumor effect on the mouse model transplanted with a human hepatoma cells.

Example 21

Preparation of GC33 Mouse-Human Chimeric Antibody

The H chain and the L chain of GC33 were amplified by PCR using a synthetic oligonucleotide, which is complementary to the 5'-terminal nucleotide sequences and has a Kozak sequence and a HindIII site, and a synthetic oligonucleotide, which is complementary to the 3'-terminal nucleotide sequences and has a BamHI site. After digestion with HindIII and BamHI, the obtained PCR product was cloned into an expression vector, HEFgγ1, in which a human IgG1 constant region was inserted, and an expression vector, HEFgκ, in which a human kappa chain constant region was inserted (Sato et al., Mol Immunol. 1994; 371-381). The vectors were introduced into a CHO cell (DG44 cell line) in accordance with the above-mentioned method, and a stably expressing cell line was established. The antibody was purified from the culture supernatant using Hi Trap ProteinG HP (Amersham). The concentration of IgG in the culture supernatant was measured by a human IgG sandwich ELISA using goat anti-human IgG (BIOSOURCE) and goat anti-human IgG alkaline phosphatase conjugate (BIOSOURCE), and the concentration was determined by the comparison with a commercially available human IgG (Cappel).

Example 22

Figure 12:
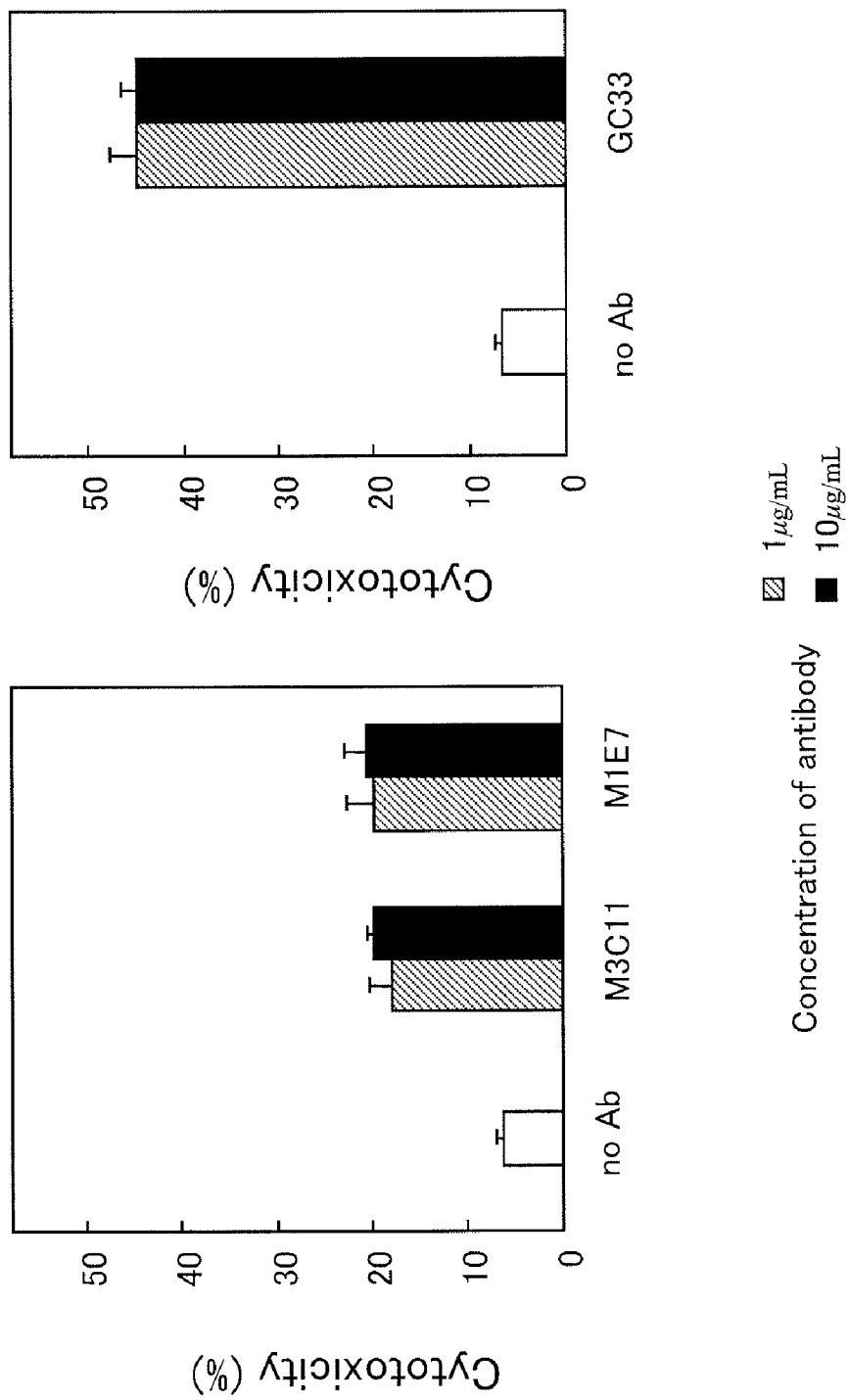
FIG. 12 shows the results of evaluating the ADCC activity of the mouse-human chimeric antibody GC33 to HepG2.

Measurement of CDC Activity and ADCC Activity Using GC33 Mouse-Human Chimeric Antibody In accordance with the methods described in Examples 16 and 17, the CDC activities and ADCC activities of GC33, M3C11 and M1E7 mouse-human chimeric antibodies were measured. As for the target cell, the CHO cell expressing full-length GPC3 was used for measuring the CDC activity and HepG2 was used for measuring the ADCC activity. The results are shown in FIG. 11 and FIG. 12, respectively. It was revealed that, in either test system, GC33 shows a strong CDC activity and ADCC activity compared with the other two antibodies.

Example 23

Epitope Analysis for GC33

Figure 14:
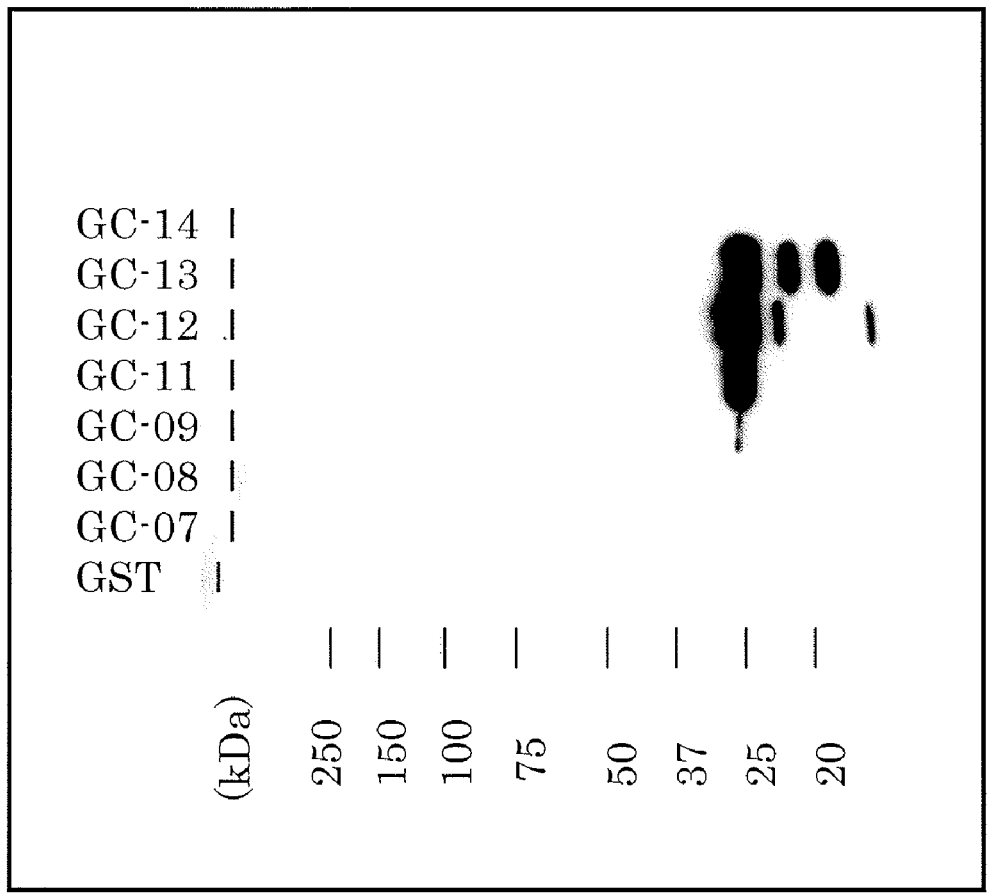
FIG. 14 shows the results of Western blotting with the use of GC33 after separating GST, GC-7, 8, 9, 11, 12, 13 and 14 by SDS-PAGE under reducing conditions.

To determine the epitope for GC33 in detail, fusion proteins of a further shorter C-terminal peptide of GPC3 and GST were prepared, and analyzed by Western blotting. The prepared GPC3-derived peptide sequences contained in the GST-fusion protein are shown in FIG. 13. Since GC33 can bind to GC-4 (aa 537-563), but cannot bind to GC-5 (aa 550-563), it was considered that the epitope is located in a region containing at least part of the aa 537-550 region. First, the peptides GC-6 (G N S Q Q A T P K D N E I S (SEQ ID NO: 93)), GC-7 (G N S Q Q A T P (SEQ ID NO: 94)), GC-8 (Q Q A T P K D N (SEQ ID NO: 95)) and GC-9 (T P K D N E I S (SEQ ID NO: 96)) were prepared. A forward oligo DNA and a reverse oligo DNA were prepared which were designed in such a manner that the cleavage site of EcoRI recognition sequence is attached to the 5' end and the cleavage site of SalI recognition sequence is attached to the 3' end, respectively. The synthesis of the oligo DNAs was done by Espec Oligo Service. The DNA was purified with C-18 cartridge, phosphorylated at the 5' end and used for the analysis. Twenty-five microliters of the forward oligo DNA (10 μM) and 25 μL of the reverse oligo DNA (10 μM) were mixed and reacted at 94° C. for 5 minutes, at 37° C. for 10 minutes, and at room temperature for 15 minutes, then left at 4° C. for 10 minutes to anneal the forward oligo DNA and the reverse oligo DNA. The concentration of the oligos was determined by the absorbance measurement at the molar ratio of the insert to the vector of 3:1. The oligos were cloned into EcoRI- and SalI-digested pGEX4T-3, and the nucleotide sequence was confirmed. A GST-fusion protein was prepared in accordance with the above-mentioned method, and purified using Gluthatione Sepharose 4B. The purified proteins were separated by SDS-PAGE under reducing conditions, and analyzed by Western blotting using GC33. As a result, the antibody GC33 could not detect any GST-fusion protein strongly, suggesting that a longer sequence at the C-terminal side is needed for the binding of GC33 (FIG. 14). Based on the above prediction, GC-11 (A T P K D N E I S T (SEQ ID NO: 97)), GC-12 (P K D N E I S T F H (SEQ ID NO: 98)), GC-13 (D N E I S T F H N L (SEQ ID NO: 99)) and GC-14 (E I S T F H N L G N (SEQ ID NO: 100)) were prepared and evaluated in the same manner. As a result, GC-11, GC-12 and GC-13 bound to GC33 more strongly, suggesting that the epitope for GC33 is located in the sequence from 544th to 553rd (P K D N E I S T F H) at the C-terminus of GPC3.

Example 24

Humanization of GC33

Antibody sequence data were obtained from publicly disclosed Kabat Database File Transfer Protocol server ftp.ebi-.ac.uk/pub/databases/kabat/) and from ImMunoGeneTics Database (IMGT). The H chain variable region and the L chain variable region were separately subjected to homology search. As a result, the H chain variable region was found to have a high homology with DN13 (Smithson et al., Mol Immunol. 1999; 36: 113-124), and the L chain variable region was found to have a high homology with homo sapiens IGK mRNA for immunoglobulin kappa light chain V11 region, partial cds, clone: K64 of the accession number of AB064105. The signal sequence of the accession number of S40357 that has a high homology with AB064105 was used as a signal sequence of the L chain. The complementarity determining region (hereinafter referred to as CDR) of GC33 were transplanted into the frame work regions (hereinafter referred to as FR) of these human antibodies to prepare a humanized antibody.

Figure 15:
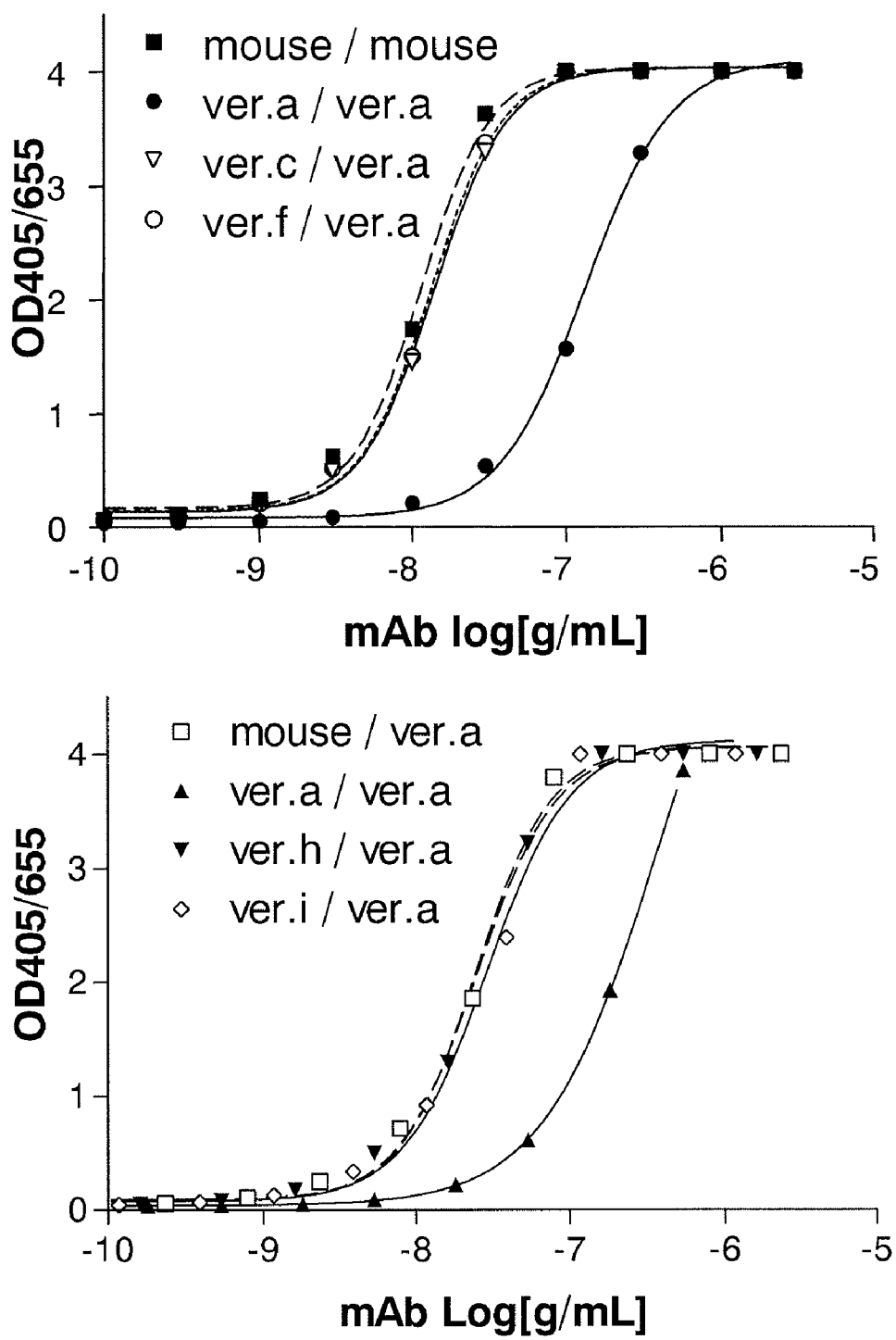
FIG. 15 shows the results of evaluating the binding activity of humanized GC33 to GPC3 by an ELISA.

Specifically, synthetic oligo DNAs of approximately 50 bases were designed in such a manner that approximately 20 bases of them were hybridized and these synthetic oligo DNAs were assembled together by the PCR method to prepare genes encoding each of the variable regions. They were digested at the HindIII site inserted in the end of the 5'-terminal synthetic oligo DNA and the BamHI site inserted in the end of the 3'-terminal synthetic oligo DNA. The fragments were cloned into an expression vector, HEFgγ1, in which a human IgG constant region was cloned, or an expression vector, HEFgκ1, in which a human kappa chain constant region was cloned (Sato et. al., Mol Immunol. 1994; 371-381). The H chain and the L chain of the humanized GC33 constructed as above were named ver.a, respectively. The binding activity of the humanized GC33, whose H chain and the L chain were both ver.a (ver.a/ver.a) was lower than that of an antibody with mouse GC33 variable regions (mouse/mouse). Antibodies were constructed in which the mouse GC33 sequence and the ver.a sequence were chimerically combined (mouse/ver.a, ver.a/mouse) with regard to the H chain and the L chain, and their binding activities were evaluated. As a result, a decrease in binding activity was observed in ver.a/mouse, indicating that the decrease in binding activity due to amino acid replacement was attributed to the H chain (FIG. 15). Then, modified H chains, ver.c, ver.f, ver.h, ver.i, ver.j, ver.k were prepared. All these humanized GC33 showed a binding activity equivalent to that of a chimeric antibody having the mouse GC33 variable region (FIG. 15). The nucleotide sequences of the humanized GC33 H chain variable regions, ver.a, ver.c, ver.f, ver.h, ver.i, ver.j, ver.k were shown in SEQ ID NOs: 77, 78, 79, 80, 81, 82 and 83, respectively, and the amino acid sequences thereof were shown in SEQ ID NOs: 84, 85, 86, 87, 88, 89 and 90, respectively. The nucleotide sequence and the amino acid sequence of a humanized GC33 L chain variable region, ver.a are shown in SEQ ID NOs: 91 and 92, respectively. In humanized GC33 H chain variable regions ver.i, ver.j and ver.k, the 6th glutamic acid residue is replaced with glutamine residue. The heat stability of these antibodies was significantly increased.

Example 25

Modification of Humanized GC33 L Chain

As for the deamidation of protein, the reaction rate constant of deamidation is known to be dependent on the primary sequence. It is also known that Asn-Gly is particularly susceptible to deamidation (Rocinson et. al., Proc. Natl. Acad. Sci. USA 2001; 98; 944-949). As for Asn33 in the CDR1 of a humanized GC33 L chain ver.a shown in SEQ ID NO: 91, the primary sequence is Asn-Gly, which is predicted to be very susceptible to deamidation.

Figure 18:
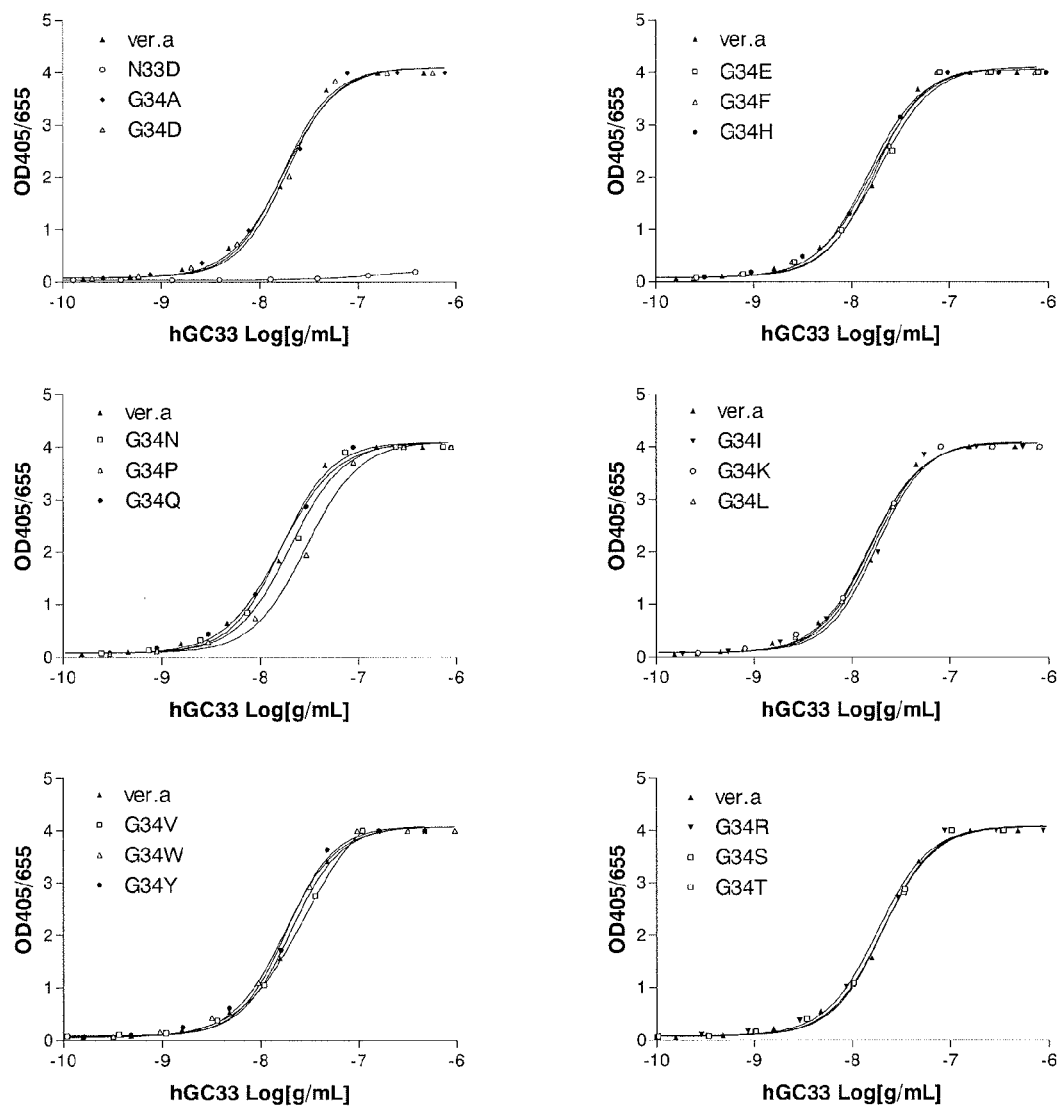
FIG. 18 shows the results of evaluating the binding activity of the modified antibodies to the soluble form of GPC3 core protein by an ELISA. Gly34 located at CDR1 in a humanized GC33 L chain variable region was replaced with any of 17 amino acids other than Cys and Met.

To evaluate the effect of deamidation of Asn33 on the binding activity, a modified antibody was prepared in which Asn33 was replaced with Asp. A point mutation was introduced using a Quick Change Site-Directed Mutagenesis Kit (Stratagene) was used. More specifically, 50 µL of a reaction mixture containing 125 ng of a sense primer (CTT GTA CAC AGT GAC GGA AAC ACC TAT: SEQ ID NO: 172), 125 ng of an antisense primer (ATA GGT GTT TCC GTC ACT GTG TAC AAG: SEQ ID NO: 173), 5 µL of 10× reaction buffer, 1 µL of dNTP mix, 10 ng of HEFgκ into which a humanized GC33 L chain ver.a had been cloned and 1 µL of Pfu Turbo DNA Polymerase was subjected to PCR of 12 cycles consisting of 95° C. for 30 seconds, 55° C. for 1 minute and 68° C. for 9 minutes. Subsequently, a restriction enzyme, DpnI, was added and digestion was carried out at 37° C. for 2 hours, and the digested product was introduced into XL1-Blue competent cell attached to the kit, whereby a transformant was obtained. The variable region was cleaved out from the clone in which each mutation was properly introduced, and cloned into HEFgκ again. It was introduced into a COS7 cell using Fugene 6 (Roche) together with HEFgγ1, in which a humanized GC33 H chain ver.k had been cloned. The antibody transiently expressed in the cell was recovered from the culture supernatant. The concentration of antibody was determined by a sandwich ELISA using the anti-human IgG antibody. The binding activity of the modified antibody was evaluated by an ELISA using an immunoplate coated with the soluble form of GPC3 core protein. As shown in FIG. 18, the binding activity was lost in the modified antibody (N33D) in which Asn33 had been replaced with Asp, suggesting that the effect of the deamidation of Asn33 on the binding activity was significant.

As a method of suppressing deamidation of Asn33, replacement of Gly34 with another amino acid has been reported (International Patent Application WO 03057881A1). In accordance with the above-mentioned method, G34 was replaced with any of 17 amino acids other than Cys and Met using a Quick Change Site-Directed Mutagenesis Kit to prepare a series of modified antibodies, namely, G34A, G34D, G34E, G34F, G34H, G34N, G34P, G34Q, G34I, G34K, G34L, G34V, G34W, G34Y, G34R, G34S and G34T. These antibodies were transiently expressed in COS7 cells, and the binding activity was evaluated using the culture supernatant. It was found that the binding activity is maintained even if G34 is replaced with another amino acid, except for Pro (G34P) and Val (G34V).

The amino acid sequences of the light chain CDR1 of the above-mentioned modified antibodies are shown in SEQ ID NO: 174 (G34A), SEQ ID NO: 175 (G34D), SEQ ID NO: 176 (G34E), SEQ ID NO: 177 (G34F), SEQ ID NO: 178 (G34H), SEQ ID NO: 179 (G34N), SEQ ID NO: 180 (G34T), SEQ ID NO: 181 (G34Q), SEQ ID NO: 182 (G34I), SEQ ID NO: 183 (G34K), SEQ ID NO: 184 (G34L), SEQ ID NO: 185 (G34S), SEQ ID NO: 186 (G34W), SEQ ID NO: 187 (G34Y), SEQ ID NO: 188 (G34R), SEQ ID NO: 189 (G34V) and SEQ ID NO: 190 (G34P), respectively. The amino acid sequences of the light chain variable regions of the above-mentioned modified antibodies are shown in SEQ ID NO: 191 (G34A), SEQ ID NO: 192 (G34D), SEQ ID NO: 193 (G34E), SEQ ID NO: 194 (G34F), SEQ ID NO: 195 (G34H), SEQ ID NO: 196 (G34N), SEQ ID NO: 197 (G34T) SEQ ID NO: 198 (G34Q), SEQ ID NO: 199 (G34I), SEQ ID NO: 200 (G34K), SEQ ID NO: 201 (G34L), SEQ ID NO: 202 (G34S), SEQ ID NO: 203 (G34W), SEQ ID NO: 204 (G34Y), SEQ ID NO: 205 (G34R), SEQ ID NO: 206 (G34V) and SEQ ID NO: 207 (G34P), respectively.

The antibody of the present invention can be used as a cell growth inhibitor, an anticancer agent or an agent for diagnosis of cancers.

Example 26

Preparation of Human Hepatoma Cell Line (SK-03) Expressing Full-Length Human GPC3

To obtain a cell line for evaluating a biological activity of the anti-GPC3 antibodies, a human hepatoma cell line expressing full-length GPC3 was established.

One microgram of a full-length human GPC3 gene expression vector treated with Pvu I was mixed with 2 µL of FuGENE (Roche) to allow for complex formation. The complex was added to SK-HEP-1 cells (purchased from ATCC) for gene introduction. After incubation in C02 incubator for 24 hours, GPC3 expressing cells were selected using Dulbecco's MEM (D-MEM, SIGMA) containing Geneticin at a final concentration of 1 mg/mL and 10% FBS. The resulting Geneticin-resistant colonies were collected and cell cloning was carried out by the limiting dilution method. The expression of human GPC3 of each cell clone was assayed by flow cytometory using the chimeric antibody GC33 and FITC-labeled goat anti-human IgG antibody (ICN). In this way, a stably expressing cell line SK-03 was obtained.

Example 27

Figure 19:
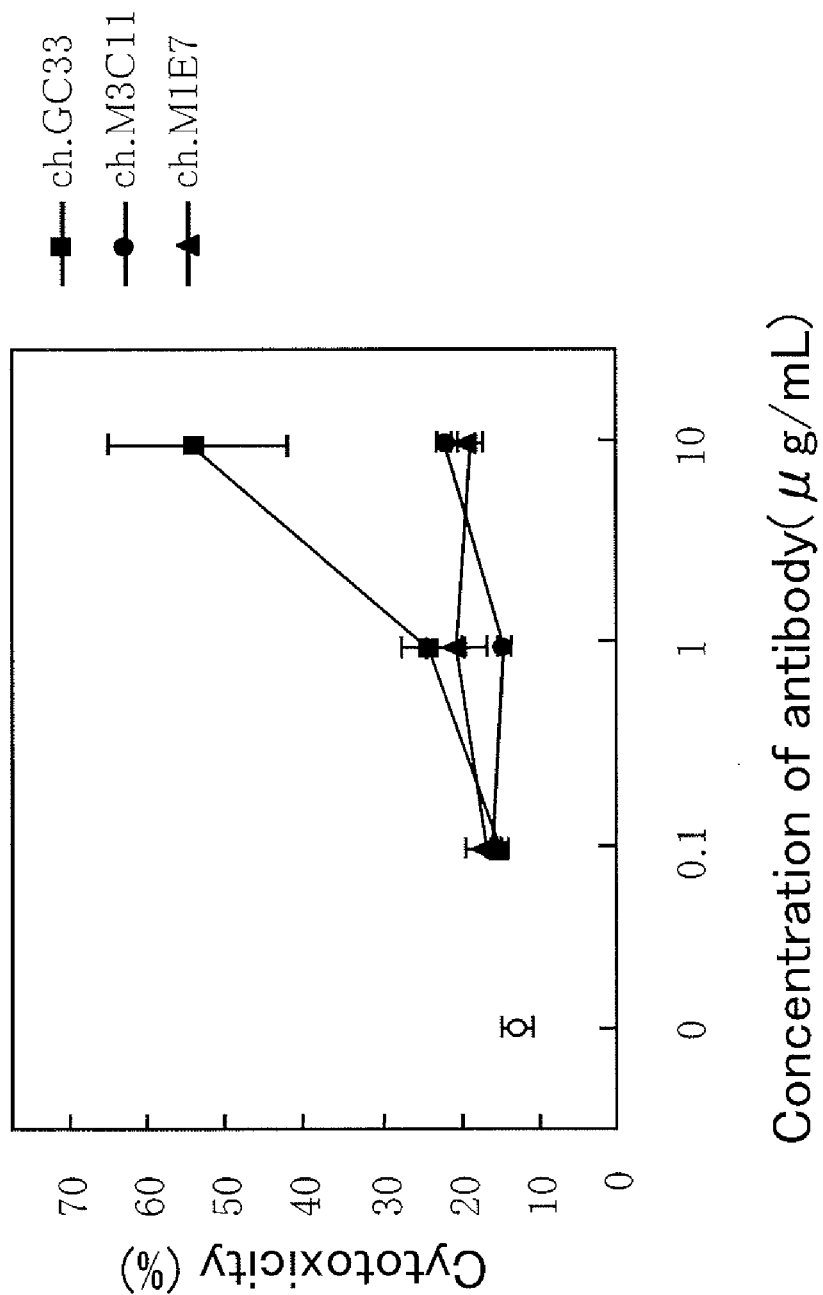
FIG. 19 shows the results of evaluating the CDC activity of the mouse-human chimeric antibodies GC33, M3C11, and M1E7 to a CHO cell that expresses full-length GPC3.
Figure 20:
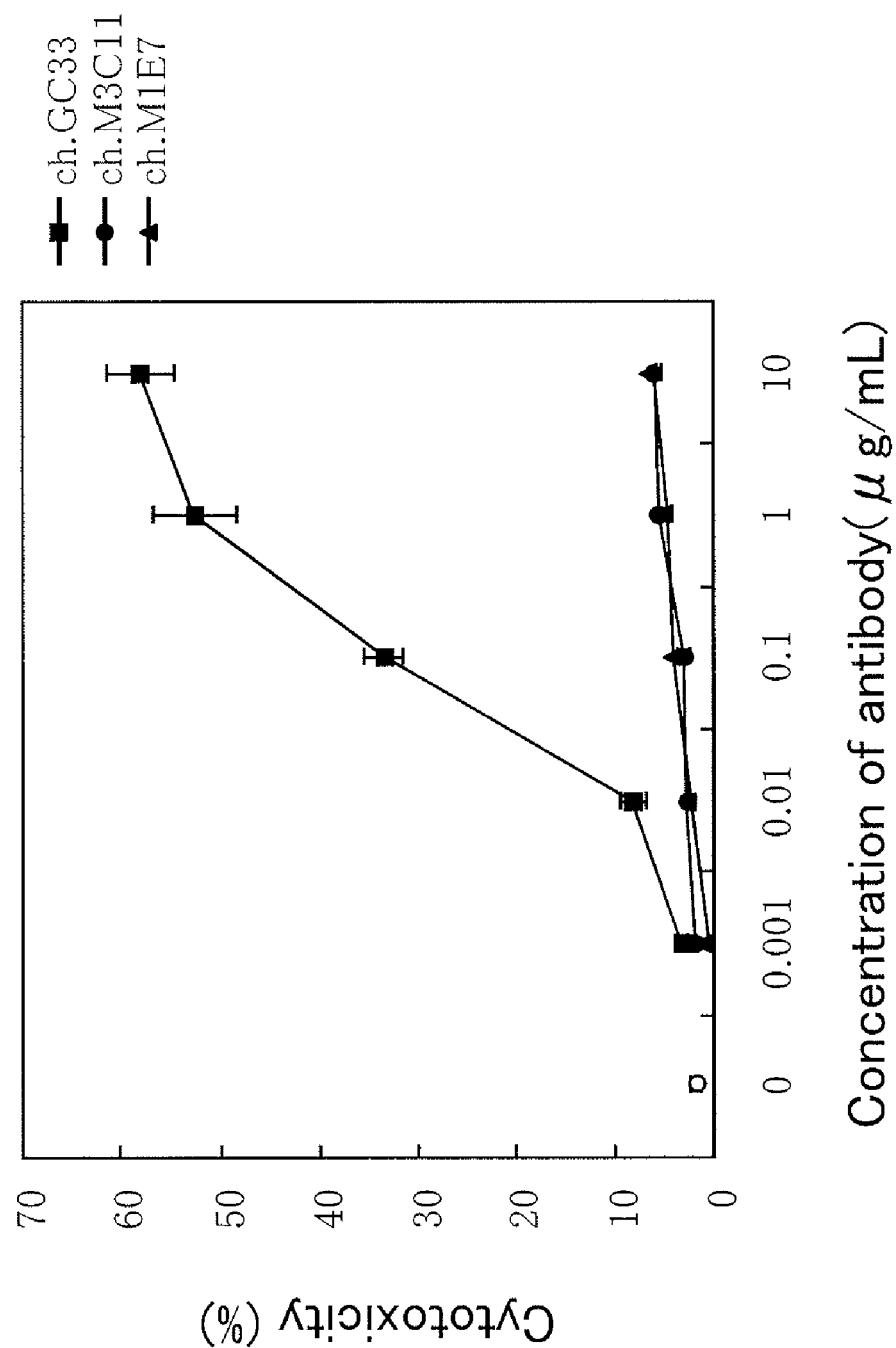
FIG. 20 shows the results of evaluating the ADCC activity of the mouse-human chimeric antibodies GC33, M3C11, and M1E7 to a human hepatoma cell line SK-03 that expresses full-length GPC3.

Comparison of CDC Activity and ADCC Activity of Mouse-Human Chimeric Antibodies In order to directly compare the CDC activity and ADCC activity of the mouse-human chimeric antibodies GC33, M3C11, and M1E7 described in Example 22, the CDC activity and ADCC activity of three antibodies were measured in the same test system according to the method described in Examples 16 and 17. As for the target cell, the CHO cell expressing full-length GPC3 was used for measuring the CDC activity and SK-03 was used for measuring the ADCC activity. The results are shown in FIG. 19 and FIG. 20, respectively. It was revealed that, in either test system, GC33 shows a stronger CDC activity and ADCC activity compared with the other two antibodies.

INDUSTRIAL APPLICABILITY

The antibody of the present invention can be used as a cell growth inhibitor, an anticancer agent and an agent for diagnosis of cancers.

The invention claimed is:

1. An isolated anti-glypican 3 antibody comprising a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 143, 144 and 158, respectively.

2. An isolated anti-glypican 3 antibody selected from the group consisting of the antibody of any one of (1)-(7):
   (1) an antibody comprising a heavy chain variable region comprising the amino acid sequence set forth in SEQ ID NO: 84 and a light chain variable region comprising the amino acid sequence set forth in SEQ ID NO: 92;
   (2) an antibody comprising a heavy chain variable region comprising the amino acid sequence set forth in SEQ ID NO: 85 and a light chain variable region comprising the amino acid sequence set forth in SEQ ID NO: 92;
   (3) an antibody comprising a heavy chain variable region comprising the amino acid sequence set forth in SEQ ID NO: 86 and a light chain variable region comprising the amino acid sequence set forth in SEQ ID NO: 92;
   (4) an antibody comprising a heavy chain variable region comprising the amino acid sequence set forth in SEQ ID NO: 87 and a light chain variable region comprising the amino acid sequence set forth in SEQ ID NO: 92;
   (5) an antibody comprising a heavy chain variable region comprising the amino acid sequence set forth in SEQ ID NO: 88 and a light chain variable region comprising the amino acid sequence set forth in SEQ ID NO: 92;
   (6) an antibody comprising a heavy chain variable region comprising the amino acid sequence set forth in SEQ ID NO: 89 and a light chain variable region comprising the amino acid sequence set forth in SEQ ID NO: 92; and
   (7) an antibody comprising a heavy chain variable region comprising the amino acid sequence set forth in SEQ ID NO: 90 and a light chain variable region comprising the amino acid sequence set forth in SEQ ID NO: 92.

3. The antibody as claimed in claim 1 or 2, which is a humanized antibody.

4. An isolated monoclonal antibody capable of binding to an epitope of glypican 3 to which a second antibody is capable of binding, wherein said second antibody comprises a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 143, 144 and 158, respectively.

5. A pharmaceutical composition comprising the antibody as claimed in claim 1.

6. A pharmaceutical composition comprising the antibody as claimed in claim 2.

7. An isolated anti-glypican 3 antibody comprising any one of (1)-(15) below:
  (1) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 174, 144 and 158, respectively;
  (2) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 175, 144 and 158, respectively;
  (3) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 176, 144 and 158, respectively;
  (4) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 177, 144 and 158, respectively;
  (5) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 178, 144 and 158, respectively;
  (6) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 179, 144 and 158, respectively;
  (7) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 180, 144 and 158, respectively;
  (8) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 181, 144 and 158, respectively;
  (9) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 182, 144 and 158, respectively;
  (10) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 183, 144 and 158, respectively;
  (11) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 184, 144 and 158, respectively;
  (12) a heavy chain variable region having CDRs 1, 2 and 3 comprising the amino acid sequence set forth in SEQ ID NO: 123, 124, and 125, respectively, and a light chain variable region having CDRs 1, 2 and 3 comprising the amino acid sequence set forth in SEQ ID NO: 185, 144, and 158, respectively;
  (13) a heavy chain variable region having CDRs 1, 2 and 3 comprising the amino acid sequence set forth in SEQ ID NO: 123, 124, and 125, respectively, and a light chain variable region having CDRs 1, 2 and 3 comprising the amino acid sequence set forth in SEQ ID NO: 186, 144 and 158, respectively;
  (14) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 187, 144 and 158, respectively; and
  (15) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 188, 144 and 158, respectively.

8. The antibody as claimed in claim 4 or 7, which is a human antibody.

9. A pharmaceutical composition comprising the antibody as claimed in claim 4.

10. A pharmaceutical composition comprising the antibody as claimed in claim 7.

11. A pharmaceutical composition comprising the antibody as claimed in claim 8.

12. A pharmaceutical composition comprising the antibody as claimed in claim 3.

13. The antibody of claim 2, wherein the antibody is:
  (1) an antibody comprising a heavy chain variable region comprising the amino acid sequence set forth in SEQ ID NO: 84 and a light chain variable region comprising the amino acid sequence set forth in SEQ ID NO: 92.

14. A pharmaceutical composition comprising the antibody as claimed in claim 13.

15. The antibody of claim 2, wherein the antibody is:
  (2) an antibody comprising a heavy chain variable region comprising the amino acid sequence set forth in SEQ ID NO: 85 and a light chain variable region comprising the amino acid sequence set forth in SEQ ID NO: 92.

16. A pharmaceutical composition comprising the antibody as claimed in claim 15.

17. The antibody of claim 2, wherein the antibody is:
  (3) an antibody comprising a heavy chain variable region comprising the amino acid sequence set forth in SEQ ID NO: 86 and a light chain variable region comprising the amino acid sequence set forth in SEQ ID NO: 92.

18. A pharmaceutical composition comprising the antibody as claimed in claim 17.

19. The antibody of claim 2, wherein the antibody is:
   (4) an antibody comprising a heavy chain variable region comprising the amino acid sequence set forth in SEQ ID NO: 87 and a light chain variable region comprising the amino acid sequence set forth in SEQ ID NO: 92.

20. A pharmaceutical composition comprising the antibody as claimed in claim 19.

21. The antibody of claim 2, wherein the antibody is:
   (5) an antibody comprising a heavy chain variable region comprising the amino acid sequence set forth in SEQ ID NO: 88 and a light chain variable region comprising the amino acid sequence set forth in SEQ ID NO: 92.

22. A pharmaceutical composition comprising the antibody as claimed in claim 21.

23. The antibody of claim 2, wherein the antibody is:
   (6) an antibody comprising a heavy chain variable region comprising the amino acid sequence set forth in SEQ ID NO: 89 and a light chain variable region comprising the amino acid sequence set forth in SEQ ID NO: 92.

24. A pharmaceutical composition comprising the antibody as claimed in claim 23.

25. The antibody of claim 2, wherein the antibody is:
   (7) an antibody comprising a heavy chain variable region comprising the amino acid sequence set forth in SEQ ID NO: 90 and a light chain variable region comprising the amino acid sequence set forth in SEQ ID NO: 92.

26. A pharmaceutical composition comprising the antibody as claimed in claim 25.

27. The antibody of claim 7, wherein the antibody comprises:
   (1) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 174, 144 and 158, respectively.

28. A pharmaceutical composition comprising the antibody as claimed in claim 27.

29. The antibody of claim 7, wherein the antibody comprises:
   (2) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 175, 144 and 158, respectively.

30. A pharmaceutical composition comprising the antibody as claimed in claim 29.

31. The antibody of claim 7, wherein the antibody comprises:
   (3) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 176, 144 and 158, respectively.

32. A pharmaceutical composition comprising the antibody as claimed in claim 31.

33. The antibody of claim 7, wherein the antibody comprises:
   (4) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 177, 144 and 158, respectively.

34. A pharmaceutical composition comprising the antibody as claimed in claim 33.

35. The antibody of claim 7, wherein the antibody comprises:
   (5) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 178, 144 and 158, respectively.

36. A pharmaceutical composition comprising the antibody as claimed in claim 35.

37. The antibody of claim 7, wherein the antibody comprises:
   (6) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 179, 144 and 158, respectively.

38. A pharmaceutical composition comprising the antibody as claimed in claim 37.

39. The antibody of claim 7, wherein the antibody comprises:
   (7) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 180, 144 and 158, respectively.

40. A pharmaceutical composition comprising the antibody as claimed in claim 39.

41. The antibody of claim 7, wherein the antibody comprises:
   (8) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 181, 144 and 158, respectively.

42. A pharmaceutical composition comprising the antibody as claimed in claim 41.

43. The antibody of claim 7, wherein the antibody comprises:
   (9) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 182, 144 and 158, respectively.

44. A pharmaceutical composition comprising the antibody as claimed in claim 43.

45. The antibody of claim 7, wherein the antibody comprises:
   (10) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 183, 144 and 158, respectively.

46. A pharmaceutical composition comprising the antibody as claimed in claim 45.

47. The antibody of claim 7, wherein the antibody comprises:
(11) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 184, 144 and 158, respectively.

48. A pharmaceutical composition comprising the antibody as claimed in claim 47.

49. The antibody of claim 7, wherein the antibody comprises:
(12) a heavy chain variable region having CDRs 1, 2 and 3 comprising the amino acid sequence set forth in SEQ ID NO: 123, 124, and 125, respectively, and a light chain variable region having CDRs 1, 2 and 3 comprising the amino acid sequence set forth in SEQ ID NO: 185, 144, and 158, respectively.

50. A pharmaceutical composition comprising the antibody as claimed in claim 49.

51. The antibody of claim 7, wherein the antibody comprises:
(13) a heavy chain variable region having CDRs 1, 2 and 3 comprising the amino acid sequence set forth in SEQ ID NO: 123, 124, and 125, respectively, and a light chain variable region having CDRs 1, 2 and 3 comprising the amino acid sequence set forth in SEQ ID NO: 186, 144 and 158, respectively.

52. A pharmaceutical composition comprising the antibody as claimed in claim 51.

53. The antibody of claim 7, wherein the antibody comprises:
(14) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 187, 144 and 158, respectively.

54. A pharmaceutical composition comprising the antibody as claimed in claim 53.

55. The antibody of claim 7, wherein the antibody comprises:
(15) a heavy chain variable region having CDRs 1, 2 and 3 comprising the amino acid sequence set forth in SEQ ID NO: 123, 124 and 125, respectively, and a light chain variable region having CDRs 1, 2 and 3 comprising the amino acid sequence set forth in SEQ ID NO: 188, 144 and 158, respectively.

56. A pharmaceutical composition comprising the antibody as claimed in claim 55.

* * * * *

UNITED STATES PATENT AND TRADEMARK OFFICE
CERTIFICATE OF CORRECTION

| | | |
|---|---|---|
| PATENT NO. | : 7,919,086 B2 | Page 1 of 1 |
| APPLICATION NO. | : 10/583795 | |
| DATED | : April 5, 2011 | |
| INVENTOR(S) | : Nakano et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 183 days.

Signed and Sealed this
Ninth Day of August, 2011

David J. Kappos
*Director of the United States Patent and Trademark Office*